US011000505B2

(12) United States Patent
Liu

(10) Patent No.: US 11,000,505 B2
(45) Date of Patent: *May 11, 2021

(54) SALVINORIN COMPOSITIONS AND USES THEREOF

(71) Applicant: The Trustees of the University of Pennsylvania, Philadelphia, PA (US)

(72) Inventor: Renyu Liu, Media, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 38 days.

This patent is subject to a terminal disclaimer.

(21) Appl. No.: 14/665,755

(22) Filed: Mar. 23, 2015

(65) Prior Publication Data

US 2015/0366840 A1    Dec. 24, 2015

Related U.S. Application Data

(63) Continuation-in-part of application No. 13/806,068, filed as application No. PCT/US2011/042427 on Jun. 29, 2011.

(60) Provisional application No. 61/968,667, filed on Mar. 21, 2014, provisional application No. 61/359,611, filed on Jun. 29, 2010.

(51) Int. Cl.
*A61K 31/366* (2006.01)
*A61K 9/00* (2006.01)
*A61K 47/40* (2006.01)

(52) U.S. Cl.
CPC .......... *A61K 31/366* (2013.01); *A61K 9/0019* (2013.01); *A61K 9/0043* (2013.01); *A61K 47/40* (2013.01)

(58) Field of Classification Search
CPC .................................. A61K 31/366
USPC ........................................ 514/455
See application file for complete search history.

(56) References Cited

U.S. PATENT DOCUMENTS

| | | |
|---|---|---|
| 2006/0052439 A1 | 3/2006 | Beguin et al. |
| 2007/0213394 A1 | 9/2007 | Beguin et al. |
| 2009/0203761 A1 | 8/2009 | Schubert et al. |
| 2010/0093872 A1 | 4/2010 | Blomberg et al. |
| 2012/0149564 A1 | 6/2012 | Tam et al. |
| 2013/0102659 A1 | 4/2013 | Liu et al. |

FOREIGN PATENT DOCUMENTS

| | | | |
|---|---|---|---|
| WO | WO 2005/089745 | | 9/2005 |
| WO | WO 2007/100775 | | 9/2007 |
| WO | WO2007100775 | * | 9/2007 |
| WO | WO 2008/119097 | | 9/2008 |

OTHER PUBLICATIONS

Inamasu et al. Subarachnoid haemorrhage as a cause of out of hospital cardiac arrest: A prospective computed tomography study. Resuscutation (2009), vol. 80, pp. 977-980.*
Bleske et al. Comparison of intravenous and intranasal administration of epinephrine during CPR in a canine model. Ann Emerg Med (1992), vol. 21, pp. 1125-1130.*
Mayfield Brain & Spine [online] Retrieved on Jul. 13, 2016 <url: https://www.mayfieldclinic.com>.*
Gillmore. Understanding the drugs used during cardiac arrest response Nursing Times (2006) vol. 102, pp. 24-30.*
Filion et al. Perioperative use of cardiac medical therapy among patients undergoing coronary artery bypass graft surgery: A systematic reviewAm Heart J (2007) vol. 154, pp. 407-414.*
Palmer et al. Symptomatic subarachnoid hemorrhage in the term newborn. J. Perinatol (1991), vol. 11, pp. 112-116.*
EMCDDA Salvia divinorum drug profile. [online] Retrieved on: Jul. 13, 2016 <url: http://www.emcdda.europa.eu/publications/drug-profiles/salvia>.*
Roquette [online] Hydroxypropyl Betacyclodextrin An Enabling Technology for Challenging Pharmaceutical Formulations (2009) pp. 1-4.*
Kasumoto et al. Recent Advance in Neurotraumology (1993), vol. pp. 240-243 (Year: 1993).*
Pluta et al. Brain Research. (1994), vol. 633, pp. 41-52. (Year: 1994).*
Manole et al. Curr Opin Pediatr. (2009), vol. 21, pp. 745-750. (Year: 2009).*
Zhang et al. Anesth Analg (2003), vol. 97, pp. 1776-1783 (Year: 2003).*
Pluta et al. Neurol Res. (2009), vol. 31, pp. 151-158). (Year: 2009).*
Nelson Stroke (2007), vol. 38, pp. 742-745 (Year: 2007).*
Wang (Written translation by STIC) (Year: 2019).*
Roth et al., "Salvinorin A: a potent naturally occurring non-nitrogenous kappa opioid selective agonist", PNAS, 2002, 99: 11934.
Butelman et al., "The plant-derived hallucinogen, salvinorin A, produces kappa-opioid agonist-like discriminative effects in rhesus monkeys", Psychopharmacology, 2004, 172: 220.
Ji et al., "Herkinorin dilates cerebral vessels via kappa opioid receptor and cyclic adenosine monophosphate (cAMP) in a piglet model", Brain Res. 2013, 1490: 95-100.
Goodson et al., " ", Medical Applications of Controlled Release, 1984, vol. 2, pp. 115-138.
Langer, R. "New methods of drug delivery" Science, 249, 1527-1533, (1990).

(Continued)

*Primary Examiner* — Taina D Matos Negron
(74) *Attorney, Agent, or Firm* — Mark S. Cohen; Pearl Cohen Zedek Zedek Latzer Baratz LLP

(57) ABSTRACT

The invention relates to salvinorin compositions and uses thereof. Specifically, the invention relates to administering salvinorin compositions to treat diseases and disorders associated with vasoconstriction, vaso-occlusion, or disruption of blood flow and autoregulation. For example, salvinorin compositions may be administered to subjects with cardiac arrest, subarachnoid hemorrhage, stroke, cerebral vascular spasm, cerebral hypoxia/ischemia, cerebral artery occlusion, or any condition involved in autoregulation impairment.

23 Claims, 43 Drawing Sheets

(56) References Cited

OTHER PUBLICATIONS

Abuchowski et al. "Immunosuppressive properties and circulating life of Achromobacter glutaminase-asparaginase covalently attached to polyethylene glycol in man" Cancer Treat Rep. 65(11-12): 1077-81 1981.

Newmark et al., "Tuberous Sclerosis evaluated by Computerized Tomography", Computerized Radiol. 1982, vol. 6, pp. 287-293.

Katre et al. "Chemical modification of recombinant interleukin 2 by polyethylene glycol increases its potency in the murine Meth A sarcoma model" Proc Natl Acad Sci U S A. 84(6):1487-91. Mar. 1987.

Su et al., "Salvinorin A pretreatment preserves cerebrovascular autoregulation after brain hypoxic/ischemic injury via extracellular signal-regulated kinase/mitogen-activated protein kinase in piglets", Anesth. Analg. 2012, 114: 200-204.

Su et al., "Salvinorin A produces cerebrovasodilation through activation of nitric oxide synthase, K receptor, and adenosine triphosphate-sensitive potassium channel", Anesthesiology 2011, 114: 374-379.

Wang et al., "Salvinorin A administration after global cerebral hypoxia/ischemia preserves cerebrovascular autoregulation via kappa opioid receptor in piglets", PloS One, 2012, 7: e41724.

Sefton, "Implantable pumps", CRC Crit. Ref. Biomed. Eng. 14:201 (1987).

Buchwald et al. "Long-term, continuous intravenous heparin administration by an implantable infusion pump in ambulatory patients with recurrent venous thrombosis."Surgery 88:507 (1980).

Saudek et al."A preliminary trial of the programmable implantable medication system for insulin delivery." N. Engl. J. Med. 321:574 (1989).

Koudstaal et al., "Headache in transient or permanent celebral Ischemia", Stroke 1991, vol. 22, pp. 754-759.

Xu et al., "Recent advance on research and application of salvia militiorrhiza", Asian Journal of Pharmacodynamics and Pharmacokinetecs, 2007, vol. 7(2), pp. 99-130.

Wang et al., "Effect of Salvia militiorrhiza and cerebral vascular spasm induced by experimental SAH in rabbits", Henan Journal of Practical Neurons Diseases, 2003-2004, abstract only.

Endoh et al., "The influence of nicardipine-, nitroglycerin-, and prostaglandin E1-induced hypotension on cerebral pressure autoregulation in adult patients during propofol-fentanyl anesthesia", Anesth. Analg. 2002, vol. 94, pp. 169-173.

Birch et al. "Neuroprotective actions of GR89696, a highly potent and selective kappa-opioid receptor agonist"British journal of pharmacology. Jul. 1991;103(3):1819.

Partial Supplementary European Search Report for European Application No. 15765744.6. dated Oct. 23, 2017.

Supplementary European Search Report for European Application No. 15765744.6 dated Jan. 29, 2018.

Loftsson et al. "Cyclodextrins in drug delivery" Expert opinion on drug delivery. Mar. 1, 2005;2(2)335-51.

Lovell KM. "The Synthesis and Pharmacological Evaluation of Salvinorin A Analogues as Opioid Receptor Probes"(Doctoral dissertation, University of Kansas), pp. 68, 88-95, 2011.

Uekama "Control of drug release by cyclodextrins" Fragrance Journal, 1991, 19(3), 22-27.

Wang Yanjing et al., Advances in studies on chemical constituents in plants of Callicarpa Linn. and their bioactivities *Chinese Traditional and Herbal Drugs*, 2008 vol. 39, Issue 01.

Chinese Office Action dated Apr. 11, 2019.

\* cited by examiner

Image of Salvinorin A

FIGURE 8

Image of Cucurbit[7]uril

Salvinorin Cucurbituril7 complex

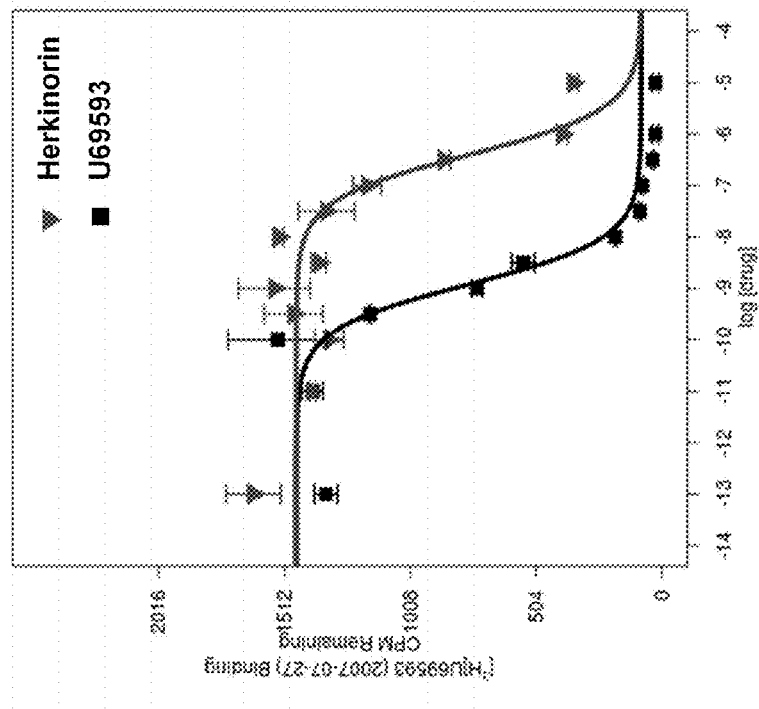
Figure 37A
Figure 37B
Figure 37

SALVINORIN COMPOSITIONS AND USES THEREOF

GOVERNMENT INTEREST STATEMENT

This invention was made with government support under grant number K08 GM093115 awarded by the National Institutes of Health. The government has certain rights in the invention.

CROSS-REFERENCE TO RELATED APPLICATIONS

This application claims the benefit of U.S. Provisional Patent Application No. 61/968,667, filed Mar. 21, 2014; and this application is a Continuation-in-Part of U.S. patent application Ser. No. 13/806,068, filed Dec. 20, 2012, which is a National Phase Application of PCT International Application No. PCT/US11/42427, International Filing Date Jun. 29, 2011, claiming priority of U.S. Provisional Patent Application No. 61/359,611, filed Jun. 29, 2010, all of which are incorporated by reference herein in their entirety.

FIELD OF THE INVENTION

The invention relates to salvinorin compositions and uses thereof. Specifically, the invention relates to administering salvinorin compositions to treat diseases and disorders associated with vasoconstriction, vaso-occlusion, or disruption of blood flow and autoregulation. For example, salvinorin compositions may be administered to subjects with cardiac arrest, subarachnoid hemorrhage, stroke, cerebral vascular spasm, cerebral hypoxia/ischemia, cerebral artery occlusion, or any condition involved in autoregulation impairment.

BACKGROUND OF THE INVENTION

Salvinorin A is an active component of *Salvia divinorum*, a perennial herb of the Lamiaceae (mint) family, indigenous to Mexico. *Salvia divinorum* has long been traditionally used to produce visionary states of consciousness during spiritual healing sessions for religious purposes. It has been shown that salvinorin A is the most highly efficacious, naturally-occurring, nonpeptide, and the only non-nitrogenous kappa opioid receptor (KOR) agonist.

Similar to the history of opium, *Salvia divinorum* as a naturally abundant plant has been used by human beings for recreational purposes for several centuries, and it has been proposed that salvinorin A could be a potential new opioid receptor agonist to be used in clinical practice, i.e. to treat depression or addiction etc. None of the other opioid KOR agonists have been used clinically so far because of their side effects. These include induction of significant dysphoria, low selectivity, respiratory depression, and unknown safety profiles. Salvinorin A does not belong to opioids despite being a KOR agonist, and it is not a controlled substance in most countries. Many intrinsic characters of the compound, i.e. quick onset, short acting, readily cross the blood brain barrier, and no respiratory depression, etc., make it an attractive possible medication, especially for neurological diseases.

Cardiac arrest (CA), especially sudden cardiac arrest, is a leading cause of death in the United States. Each year, there are approximately 295,000 cases of out-of hospital CA with a survival rate of 7% and 200,000 cases of in-hospital CA with a survival rate of 20-30%. More than half of CA survivors subsequently suffer from various degrees of permanent neurological dysfunction including brain death. Studies in human subjects and different CA animal models demonstrate that these neurological conditions are induced by ischemia/reperfusion (IR) injury to the brain. Within seconds of CA, blood flow and oxygen delivery to the brain ceases, causing a cascade of metabolic events that may lead to brain tissue hypoxia and necrosis (hypoxia/ischemic injury). When circulation is restored via cardiopulmonary resuscitation (CPR), secondary injury from reperfusion may further exacerbate the brain injury during this time (reperfusion injury).

Presently, therapeutic hypothermia is considered the only effective post-CA treatment for neurological injuries. However, this treatment can only be applied to eligible patient populations and can be dangerous in under-resourced facilities, thereby leading to, among other things, an increased incidence of mortality, multiple organ failure, pulmonary hypertension, and bleeding, Therefore, a significant medical need exists for an easily manageable medication to improve survival rate and reduce the burden of neuronal injury from CA.

Stroke is a leading cause of death worldwide. Each year, about 795,000 people experience a new or recurrent stroke in the United States; every 40 seconds, someone in the U.S. has a stroke; every 4 minutes, someone dies from a stroke. Stroke is a leading cause of serious long-term disability. 87% of all strokes are ischemic when blood supply to the brain is interrupted, a typical example of ischemia/reperfusion (IR) organ injury. Many potential neuroprotectants that reduce such neuronal injuries in experimental animals have failed in clinical trials. Due to the narrow therapeutic window of stroke, a potential neuroprotectant has to be able to be delivered in a timely manner without significant barrier with quick onset time.

Subarachnoid hemorrhage (SAH) occurs in the U.S. in approximately 30,000 patients each year. In up to 70% of SAH patients, cerebral vasospasm is estimated and is a major source of morbidity and mortality. A large number of treatment methods have been proposed and evaluated. Nevertheless, no single treatment modality has proven effective.

Salvinorin A is a very hydrophobic molecule and is insoluble in water. Salvinorin A is soluble in known to be soluble in organic solvents like ethanol, DMSO, and acetone. However, these solvent are not suitable for routine clinical use, especially for intravenous (IV) delivery. Since salvinorin A is useful clinically, for neurological disorders, there is a need to identify materials, preferably FDA approved materials, which can be used to formulate salvinorin A for clinical delivery.

Accordingly, there exists a need for exploring new uses and formulations of salvinorin A as a clinical medication to treat various diseases and disorders.

SUMMARY OF THE INVENTION

In one aspect, provided herein are methods of treating neurological injuries associated with cardiac arrest in a subject suffering from or having suffered cardiac arrest, the methods comprising: administering to said subject a therapeutically effective amount of salvinorin or a pharmaceutical composition thereof. In another aspect, provided herein are methods of increasing the likelihood of survival in a subject suffering from or having suffered cardiac arrest, the methods comprising: administering to said subject a therapeutically effective amount of salvinorin or a pharmaceutical composition thereof.

In another aspect, provided herein are methods of treating cerebral vasospasm in a subject with a subarachnoid hemorrhage, the methods comprising: administering to said subject a therapeutically effective amount of salvinorin or a pharmaceutical composition thereof.

In another aspect, provided herein are methods of treating a cerebral artery occlusion in a subject suffering from or having suffered a cerebral artery occlusion, the methods comprising: administering to said subject a therapeutically effective amount of salvinorin or a pharmaceutical composition thereof.

In another aspect, provided herein are methods of reducing infarct size in a subject suffering from or having suffered a cerebral hypoxic/ischemic insult, the methods comprising: administering to said subject a therapeutically effective amount of salvinorin or a pharmaceutical composition thereof. In yet another aspect, provided herein are methods of reducing vascular leakage in a subject suffering from or having suffered a cerebral hypoxia/ischemia, the methods comprising: administering to said subject a therapeutically effective amount of salvinorin or a pharmaceutical composition thereof.

In another aspect, provided herein are pharmaceutical compositions of salvinorin A, the compositions comprising: an aqueous solution of salvinorin A and a cyclodextrin.

In another aspect, provided herein are pharmaceutical compositions, the compositions comprising: salvinorin for use in the methods described herein.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

Figure 8:
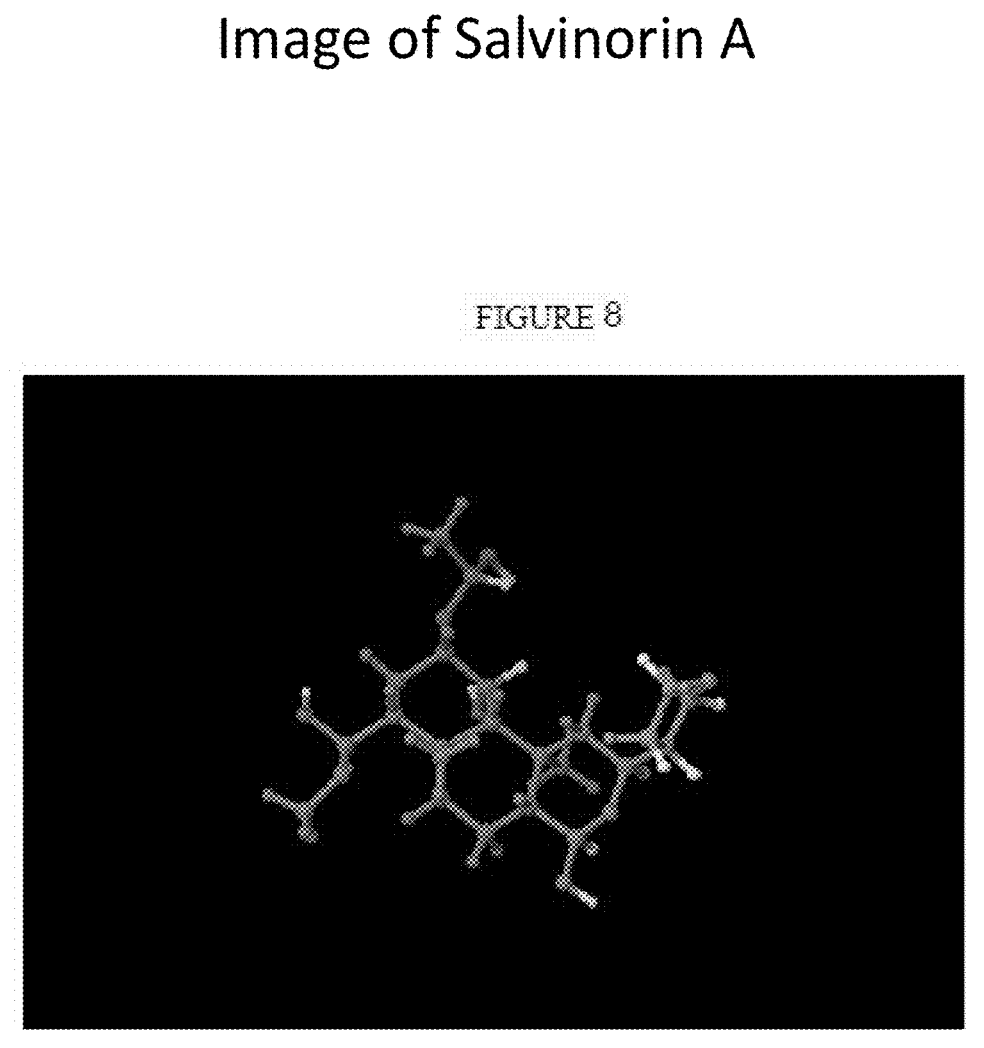

FIG. 8 is an image of salvinorin A.
FIG. 10 is an image of salvinorin-cucurbituril complex.
FIG. 12 is an image of a salvinorin-cucurbituril complex.

FIG. 36A demonstrates the binding affinity of herkinorin with the mu receptor as compared to DAMGO, a potent mu agonist. The $K_i$ is 2.5 nM for DAMGO and 45 nM for herkinorin. The model illustrated in FIG. 36B suggests that herkinorin (labeled as H over the red sphere ligand in the binding pocket) binds to the same binding site as that for β-funaltrexamine (labeled as β over the light blue sphere ligand in the binding pocket), a selective mu opioid receptor ligand found in the crystal structure.

FIG. 37. Affinity determination for herkinorin in HEK cells over-expressed with kappa opioid receptor and the location of the binding site. FIG. 37A demonstrates the binding affinity of herkinorin with kappa receptor as compare to U69593, a potent kappa agonist. The $K_i$ is 0.8 nM for U69593 and 184 nM for herkinorin. The model illustrated in FIG. 37B suggests that herkinorin (labeled as H over the red sphere ligand in the binding pocket) binds to the same binding site as that for JDTic (labeled as J over the green sphere ligand in the binding pocket), a selective kappa opioid receptor ligand found in the crystal structure.

FIG. 38 demonstrates the dilatation effect of herkinoin (Herk) on pial artery is blocked by the kappa receptor antagonist norbinaltorphimine (NTP) (FIG. 38A); but not blocked by the mu receptor antagonist β-funaltrexamine (β-FNA, FIG. 38B). The dilatation effect of herkinoin is equivalent to that of isoproterenol (ISO), a potent beta adrenergic agonist (FIG. 38A)(Ps>0.05). Administration of NTP or β-FNA alone does not have any dilatation effects (One way Anova followed by Dunnett's multiple comparison tests). n=5 for each group. *for p<0.05, for p<0.01, *for p<0.005 in t-tests, and #for p<0.05 in ANOVA tests.

FIG. 39A demonstrates that the levels of cAMP in CSF elevated with herkinorin administration, which were abolished with administration of the kappa antagonist NTP. FIG. 39B demonstrates that the cerebrovasodilation effects of herkinorin were abolished by administration of 10 µM Rp-cAMPS, a cAMP antagonist (n=5) Sp: Sp-cAMPS, Rp: Rp-8-Br-cAMPs. *for p<0.05, for p<0.01, *for p<0.005

DETAILED DESCRIPTION OF THE INVENTION

Figure 1:
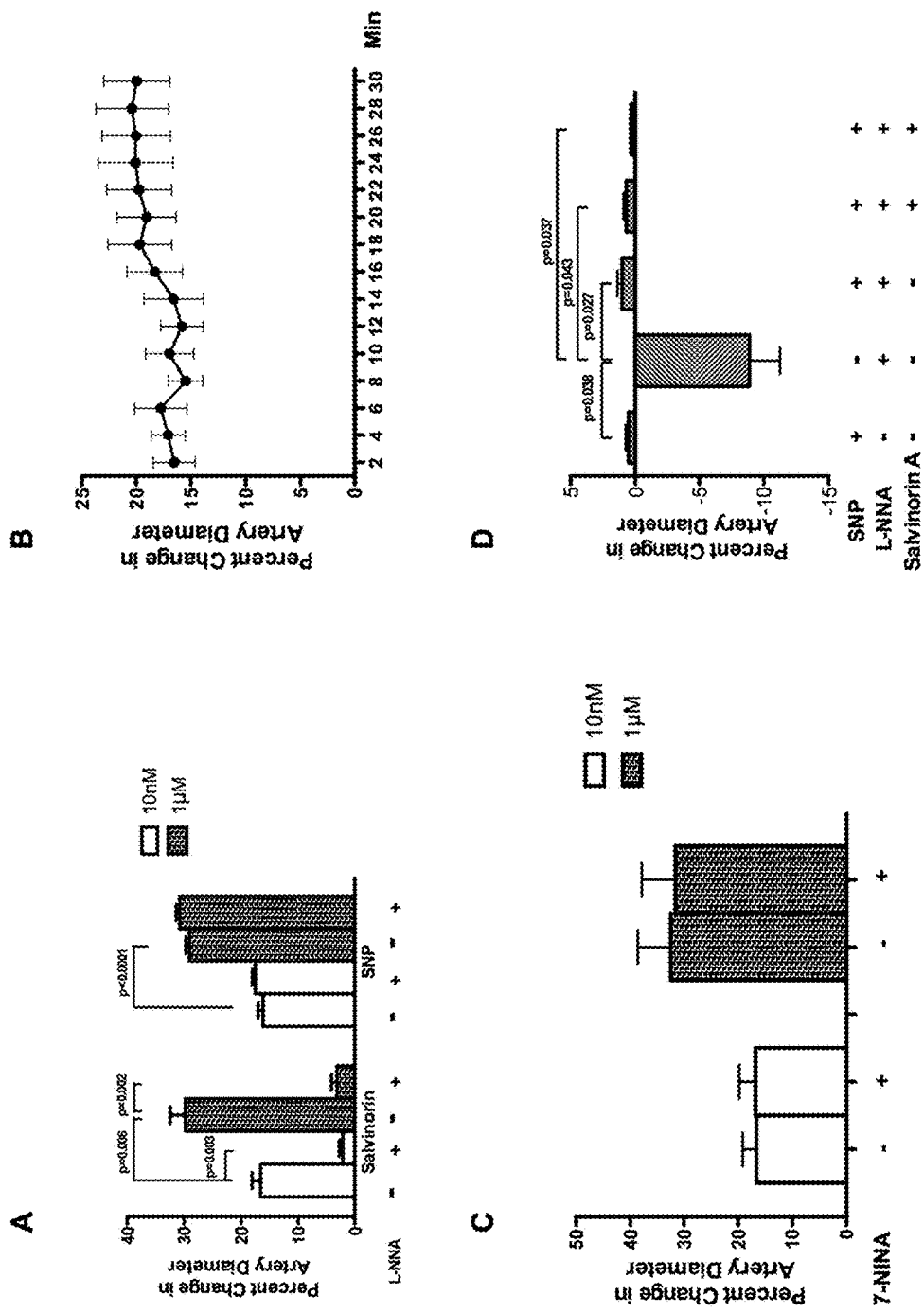
FIG. 1. Salvinorin A dilated the pial artery of piglet. Panel A: Salvinorin A dose-dependently dilated brain pial artery. L-NNA, a Nitric Oxide Synthase Inhibitor, blocks the dilation effects of salvinorin but not SNP. Panel B: Salvinorin A administration per 2 minutes can sustain the pial artery dilatation. Panel C: 7-NINA the nNOS inhibitor did not block the dilation effects of salvinorin. Panel D: SNP (100 pM) restored the construction effects of L-NNA but didn't restore the dilation effects induced by salvinorin A which was blocked by L-NNA (n=5). L-NNA: N(G)-nitro-L-arginine; SNP: sodium nitroprusside; 7-NINA: 7-nitroindazole.

The invention relates to salvinorin compositions and uses thereof. Specifically, the invention relates to administering salvinorin to increase survival of a subject following cardiac arrest or stroke in that subject. The invention further relates to treating a subject with cerebral vascular spasm, a subarachnoid hemorrhage, cerebral hypoxia/ischemia, cerebral artery occlusion, or any condition involved in autoregulation impairment.

In one aspect, provided herein are methods of treating neurological injuries associated with cardiac arrest in a subject suffering from or having suffered cardiac arrest, the methods comprising: administering to said subject a therapeutically effective amount of salvinorin or a pharmaceutical composition thereof. In another aspect, provided herein are methods of increasing the likelihood of survival in a subject suffering from or having suffered cardiac arrest, the methods comprising: administering to said subject a therapeutically effective amount of salvinorin or a pharmaceutical composition thereof.

In another aspect, provided herein are methods of treating cerebral vasospasm in a subject with a subarachnoid hemorrhage, the methods comprising: administering to said subject a therapeutically effective amount of salvinorin or a pharmaceutical composition thereof.

In another aspect, provided herein are methods of treating a cerebral artery occlusion in a subject suffering from or having suffered a cerebral artery occlusion, the methods comprising: administering to said subject a therapeutically effective amount of salvinorin or a pharmaceutical composition thereof.

In another aspect, provided herein are methods of reducing infarct size in a subject suffering from or having suffered a cerebral hypoxia/ischemia, the methods comprising: administering to said subject a therapeutically effective amount of salvinorin or a pharmaceutical composition thereof. In yet another aspect, provided herein are methods of reducing vascular leakage in a subject suffering from or having suffered a cerebral hypoxia/ischemia, the methods comprising: administering to said subject a therapeutically effective amount of salvinorin or a pharmaceutical composition thereof.

In another aspect, provided herein are pharmaceutical compositions, the compositions comprising salvinorin for use in the methods described herein.

In another aspect, provided herein are methods for producing cerebrovasodilation in a subject in need thereof, the methods comprising: administering to said subject a therapeutically effective amount of salvinorin or a pharmaceutical composition thereof. In another aspect, provided herein are methods for treating a disease associated with cerebrovasospasm, hypoxia, and/or ischemia in a subject, the method comprising: administering to said subject a therapeutically effective amount of salvinorin or a pharmaceutical composition thereof.

In another aspect, provided herein are methods for treating a disease associated with vasoconstriction, vaso-occlusion, or disruption of blood flow and autoregulation in a subject, the methods comprising: administering to said subject a therapeutically effective amount of salvinorin or a pharmaceutical composition thereof. In another aspect, provided herein are methods for producing a sedative or anesthetic effect in a subject in need thereof, the methods comprising: administering to said subject a therapeutically effective amount of salvinorin or pharmaceutical composition thereof.

In another aspect, provided herein are pharmaceutical compositions, the compositions comprising: a therapeutically effective amount of salvinorin, wherein said salvinorin is present in an amount effective to produce cerebrovasodilation in a subject in need thereof. In another aspect, provided herein are pharmaceutical compositions, the compositions comprising: a therapeutically effective amount of salvinorin, wherein said salvinorin is present in an amount effective to treat a disease associated with cerebrovasospasm, hypoxia, and/or ischemia in a subject. In another aspect, provided herein are pharmaceutical compositions, the compositions comprising: a therapeutically effective amount of salvinorin to treat cerebral vasospasm in a subject with a subarachnoid hemorrhage.

In another aspect, provided herein are pharmaceutical compositions, the compositions comprising: a therapeutically effective amount of salvinorin, wherein said salvinorin is present in an amount effective to provide organ protection from hypoxia/ischemia in a subject. In another aspect, provided herein are pharmaceutical compositions, the compositions comprising: a therapeutically effective amount of salvinorin, wherein said salvinorin is present in an amount effective to treat a disease associated with vasoconstriction, vaso-occlusion, or disruption of blood flow and autoregulation in a subject.

In another aspect, provided herein are pharmaceutical compositions, the compositions comprising: a therapeutically effective amount of salvinorin, wherein said salvinorin is present in an amount effective to produce a sedative or antinociceptive effect in a subject in need thereof.

In another aspect, provided herein are pharmaceutical compositions of salvinorin A, the compositions comprising: an aqueous solution of salvinorin A and a cyclodextrin. Preferably, the cyclodextrin is a 2-hydroxypropyl-cyclodextrin, such as 2-hydroxypropyl-β-cyclodextrin (HPBCD) or 2-hydroxypropyl-γ-cyclodextrin (HPGCD). More preferably, the cyclodextrin is 2-hydroxypropyl-β-cyclodextrin (HPBCD). In some embodiments, the composition is adapted for intravenous administration. In some embodiments, the salvinorin A concentration is at least 25 µg/mL. Preferably, the salvinorin A concentration is at least 50 µg/mL.

In some embodiments, the cyclodextrin (e.g., HPBCD) concentration in the aqueous salvinorin A solution is at least 1% (w/v), at least 2.5% (w/v), at least 5% (w/v), at least 7.5% (w/v), at least 10% (w/v), at least 12.5% (w/v), at least 15% (w/v), at least 17.5% (w/v), at least 20% (w/v), at least 22.5% (w/v), or at least 25% (w/v). In some embodiments, the cyclodextrin (e.g., HPBCD) concentration in the aqueous salvinorin A solution is less than 50% (w/v), less than 45% (w/v), less than 40% (w/v), less than 35% (w/v), less than 30% (w/v), less than 25% (w/v), less than 22.5% (w/v), less than 20% (w/v), less than 17.5% (w/v), less than 15% (w/v). Preferably, the cyclodextrin is HPBCD with a concentration in the aqueous salvinorin A solution of about least 20% (w/v).

Figure 7:
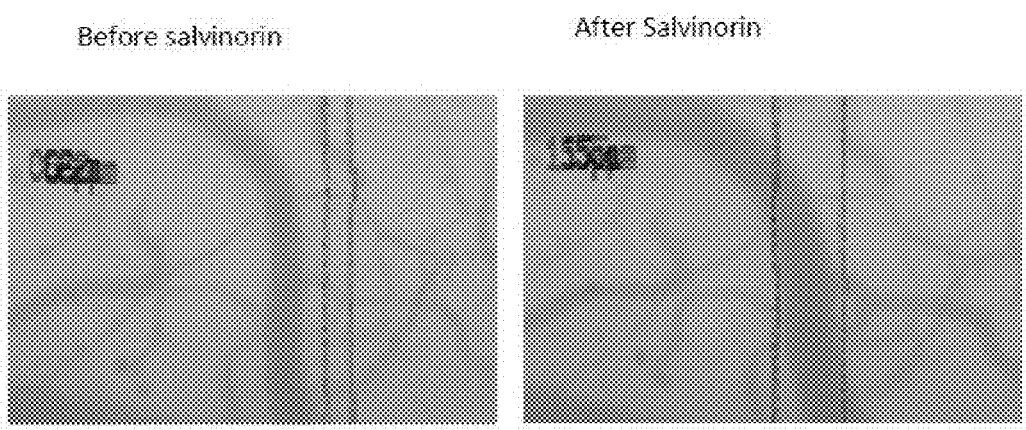
FIG. 7. Adding 1 µM of salvinorin A over the pial artery dilated the vessel immediately within seconds. It dilated the artery ~40% and the vessel diameter returned to baseline within 5 minutes.
Figure 9:
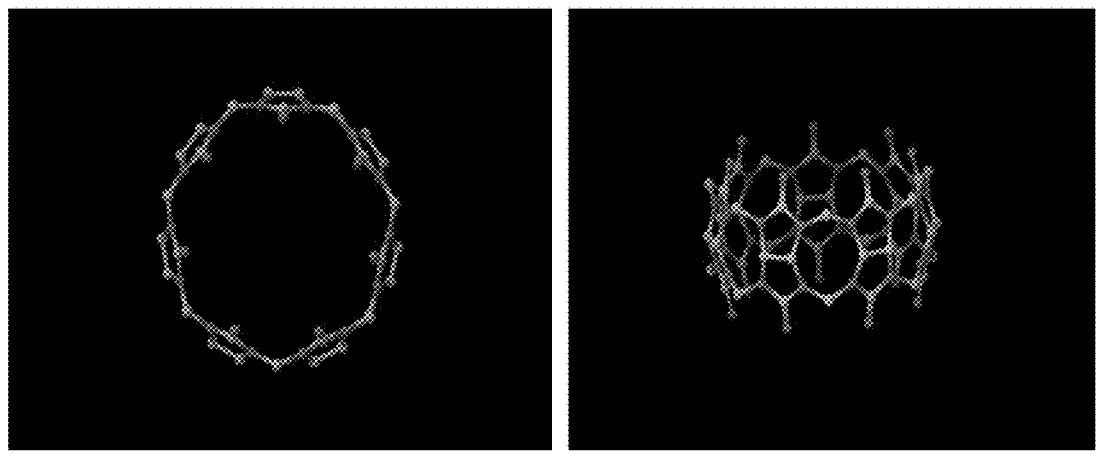
FIG. 9 is an image of cucurbituril.

The inventor of the instant application surprisingly and unexpectedly found that salvinorin dilates cerebral vessels dramatically with rapid onset and offset, and without a change in hemodynamics. The diameter of the cerebral artery dilated up to 40% with 1 micromolar salvinorin as shown in FIG. 7. The vessels dilated immediately after application of salvinorin and the dilation effect lasted less than 3 to 5 minutes. This finding demonstrates that salvinorin can be used to treat cerebral vascular spasm in stroke, brain injury, or other related clinical situations associated with cerebral vascular spasm, including post subarachnoid hemorrhage and head trauma. Furthermore, salvinorin may be used to treat towards spinal cord ischemia and other nerve ischemia.

Salvinorin A and its analogues are known compounds. Salvinorin A, the active component of *Salvia divinorum*, which is used by nearly a million people for recreational purposes annually in United States, is the only known non-nitrogenous selective kappa opioid receptor (KOR) agonist.

A diterpene salvinorin A has been shown to be a high affinity and selective kappa opioid receptor agonist. See Roth et al., Proc. Natl. Acad. Sci. USA 99:11934 (2002); and Butelman et al., Psychopharmacology 172:220 (2004).

Salvinorins and their derivatives are known in the art. For example, salvinorins, their derivatives, and methods for synthesizing them are described in U.S. 2006/0052439, U.S. 2007/0213394, WO 2005/089745, and WO2008/119097, each of which is incorporated by reference herein in its entirety.

A salvinorin or its derivative, known to one of skilled in the art, may be used in the methods and compositions described herein. Examples of a salvinorin include, but are not limited to, salvinorin A, B, C, D, E, or F. In one embodiment, salvinorin is salvinorin A. In another embodiment, salvinorin is salvinorin B. In another embodiment, salvinorin is salvinorin C. In another embodiment, salvinorin is salvinorin D. In another embodiment, salvinorin is salvinorin E. In another embodiment, salvinorin is salvinorin F. In another embodiment, salvinorin is an ester of a salvinorin. In another embodiment, salvinorin is a salvinorin benzoate. In another embodiment, salvinorin is a metabolite of salvinorin. In another embodiment, salvinorin is an analogue of salvinorin A. For example, herkinorin, an analogue of salvinorin A (Ji F, et al., Brain Res. 2013, 1490:95-100, which is hereby incorporated by reference in its entirety). Other salvinorin analogues that may be used in the methods and compositions described herein are 2-O-ethoxymethylsalvinorin B and 2-O-methoxymethylsalvinorin B.

According to one embodiment, administering a therapeutically effective amount of a salvinorin produces vasodilation in a subject in need thereof.

The invention further provides methods of treating a disease or condition, comprising administering to a mammal in need thereof a therapeutically effective amount of salvinorin.

In one embodiment, methods are provided for treating a disease associated with vasoconstriction, vaso-occlusion, or disruption of blood flow and autoregulation in a subject, the method comprising: administering to said subject a therapeutically effective amount of salvinorin or a pharmaceutical composition thereof.

The pharmaceutical compositions described herein may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which toxic or detrimental effects of the molecule are outweighed by the therapeutically beneficial effects.

As used herein, the terms "treat" and "treatment" refer to therapeutic treatment, including prophylactic or preventative measures, wherein the object is to prevent or slow down (lessen) an undesired physiological change associated with a disease or condition. For example, treating neurological injuries associated with cardiac arrest includes, but is not limited to, preventing neurological injuries in a subject suffering from or having suffered cardiac arrest. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition. "Treatment" can also mean prolonging survival as compared to expected survival if not receiving treatment. Those in need of treatment include those already with the disease or condition as well as those prone to having the disease or condition or those in which the disease or condition is to be prevented.

Examples of diseases or disorders caused by or otherwise associated with vasoconstriction, vaso-occlusion, or disruption of blood flow and autoregulation, include, but are not limited to, a cerebral vascular spasm, a subarachnoid hemorrhage, a stroke, a brain trauma or injury, an ischemia reperfusion injury, low perfusion status, and hypoxia.

The salvinorins and pharmaceutical compositions thereof described herein can administered to a subject by a method known in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally, intrathecally, and inhalationally. In preferred embodiments, they are administered transmucosally. In more preferred embodiments, they are administered intranasally.

In another embodiment of methods and compositions described herein, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the pharmaceutical compositions are administered by intravenous, intra-arterial, or intramuscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered intranasally and are thus formulated in a form suitable for intranasal administration.

In another embodiment, the pharmaceutical compositions are administered topically to body surfaces and are thus formulated in a form suitable for topical administration. Topical formulations include gels, ointments, creams, lotions, drops and the like.

In another embodiment, the pharmaceutical composition is administered as a suppository, for example, a rectal suppository or a urethral suppository. In another embodiment, the pharmaceutical composition is administered by subcutaneous implantation of a pellet. In another embodiment, the pellet provides for controlled release of active agent over a period of time.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g., *acacia*, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which of the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials are used; e.g. in microspheres in or an implant. In yet another embodiment, a controlled release system is placed in proximity to the target cell, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, cyclodextrin, cucurbituril, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compounds solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In one embodiment, the methods comprise administering an active compound as the sole active ingredient. However, also encompassed within the scope of the present invention are methods for treating diseases and disorders that comprise administering the active compound in combination with one or more additional therapeutic agents. These additional agents are appropriate for the disease or disorder that is being treated, as is known in the art.

The other therapeutically effective agent may be conjugated to the salvinorin, incorporated into the same composition as the salvinorin, or may be administered as a separate composition. The other therapeutically agent or treatment may be administered prior to, during and/or after the administration of the salvinorin.

The administration of the salvinorin with other agents and/or treatments may occur simultaneously, or separately, via the same or different route, at the same or different times. Dosage regimens may be adjusted to provide the optimum desired response (e.g., a therapeutic or prophylactic response).

Effective doses of the compositions described herein, for treatment of conditions or diseases as described herein vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

In one example, a single bolus may be administered. In another example, several divided doses may be administered over time. In yet another example, a dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms are dictated by and directly dependent on the unique characteristics of the active compound and the particular therapeutic or prophylactic effect to be achieved.

The composition may be administered only once, or it may be administered multiple times or continuous infusion. For multiple dosages, the composition may be, for example, administered three times a day, twice a day, once a day, once every two days, twice a week, weekly, once every two weeks, or monthly.

Dosage values may vary with the type and severity of the condition to be alleviated. It is further understood that for any particular subject, specific dosage regimens may be adjusted over time according to the individual need and the professional judgment of the person administering or supervising administration of the compositions, and that dosage ranges set forth herein are exemplary and are not intended to limit the scope or practice of the methods.

"Administration" to a subject is not limited to any particular delivery system and may include, without limitation, parenteral (including subcutaneous, intravenous, intramedullary, intraarticular, intramuscular, or intraperitoneal injection) rectal, topical, transdermal or oral (for example, in capsules, suspensions or tablets), intrathecal, intranasal and inhalational. Administration to a subject may occur in a single dose or in repeat administrations or continuous infusion, and in any of a variety of physiologically acceptable salt forms, and/or with an acceptable pharmaceutical carrier and/or additive as part of a pharmaceutical composition. Once again, physiologically acceptable salt forms and standard pharmaceutical formulation techniques are known to persons skilled in the art (see, for example, Remington's Pharmaceutical Sciences, Mack Publishing Co.).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, when referring to a measurable value such as an amount, a temporal duration, a concentration, and the like, may encompass variations of ±20% or ±10%, more preferably ±5%, even more preferably ±1%, and still more preferably ±0.1% from the specified value, as such variations are appropriate to perform the disclosed methods.

The methods of treatment described herein can be used to treat a suitable mammal, including primates, such as monkeys and humans, horses, cows, cats, dogs, rabbits, and rodents such as rats and mice. Preferably, the mammal to be treated is human.

Any reference including patents, patent applications, or scientific publications, cited herein, are incorporated by reference in their entirety.

The following examples are presented in order to more fully illustrate the preferred embodiments of the invention. They should in no way be construed, however, as limiting the broad scope of the invention.

EXAMPLES

Example 1

Salvinorin a Produces Cerebrovasodilation Through Activation of Nitric Oxide Synthase, Kappa Receptor and Adenosine Triphosphate Sensitive Potassium Channel In this Example, we demonstrated that salvinorin A dilates pial arteries under resting tone and elevated tone conditions induced by hypocarbia or endothelin via activation of nitric oxide synthase, Adenosine Triphosphate Sensitive Potassium ($K_{ATP}$) channels and kappa receptors.

Materials and Methods

Salvinorin A (purity ≥98%), sodium nitroprusside (SNP), N(G)-nitro-L-arginine (L-NNA), glibenclamide, iberiotoxin, cromakalim, calcitonin-gene related polypeptide (CGRP), NS 1619, naloxone, methionine enkephalin, nor-binaltorphimine, 7-nitroindazole(7-NINA), sulpiride and isoproterenol are obtained from Sigma-Aldrich (St. Louis, Mo., USA). All other chemicals were also obtained from Sigma and were of reagent grade.

Animals and Surgery

Newborn pigs (1-6 days old, weighing 1.3-1.8 kg) of both genders were used for this study. Protocols were approved by the Institutional Animal Care and Use Committee of the University of Pennsylvania. The animals were induced with isoflurane (1-2 minimal alveolar concentration) and then maintained with alpha-chloralose (80-100 mg/kg supplemented with 5 mg/kg/h IV). Both femoral arteries were catheterized to monitor blood pressure and blood gas. A catheter was inserted into right femoral vein for medication administration. The animals were ventilated with room air after trachea cannulation. Rectal temperature was maintained at 37-39° C. by a heating pad. A closed cranial window was placed for direct pial artery visualization and diameter measurement. The closed cranial window consisted of three parts: a stainless steel ring, a circular glass cover-slip, and three ports consisting of 17-gauge hypodermic needles attached to three precut holes in the stainless steel ring. Cortical periarachnoid cerebrospinal fluid (CSF) was collected through the cranial window port for cyclic guanosine monophosphate (cGMP) determination. Before placing the window, the scalp was reflected and an opening was made in the skull over the parietal cortex. Then the dura mater was cut and retracted over the bone edge. The cranial window was placed on the cranial opening and cemented in place with dental acrylic. The space under the window was filled with artificial CSF with the following composition (in mM): 3.0 KCl, 1.5 $MgCl_2$, 1.5 $CaCl_2$, 132 NaCl, 6.6 Urea, 3.7 Dextrose, and 24.6 $NaHCO_3$ per liter, pH 7.33, $PCO_2$ 46 mmHg and $PO_2$ 43 mmHg. The artificial CSF was warmed to 37-38° C. before application to the cerebral cortical surface. Pial arteries were observed with a television camera mounted on a dissecting microscope. Vascular diameter was measured from a video monitor connected the camera with a video microscaler (model VPA 550, For-A-Corp., Los Angeles, Calif.).

Experimental Protocols

Pial artery diameter (small artery diameter 120-160 micro meter; arteriole diameter 50-70 micro meter) was monitored and recorded every half minute for 10 min after injection of artificial CSF in the presence or absence of the investigated drug. In general, the window was flushed over 30 s with 1-2 ml CSF through the port connected into the side of the window. CSF samples were collected for cGMP analysis before and at 10 min after medication administration. We collected the cerebral cortical periarachnoid CSF by slowly infusing CSF into one port of the window and allowing the CSF to drip freely into a collection tube on the opposite port.

Responses to salvinorin A (10 nM, 1 μM, dissolved with alcohol) and SNP (10 nM, 1 μM), were obtained in the absence and presence of N(G)-nitro-L-arginine (L-NNA, 1 μM), a nitric oxide synthase (NOS) inhibitor and 7-nitroindazole (100 nM), an antagonist of neuronal NOS.

In order to distinguish the direct or permissive roles of nitric oxide in the dilation response to salvinorin A, pial artery diameter changes were recorded after SNP (100 pM), a sub threshold vascular concentration of a nitric oxide donor, administration together with L-NNA and salvinorin A. The influences of sulpiride (100 nM), a dopamine receptor D2 antagonist: glibenclamide (100 nM), a $K_{ATP}$ channel antagonist; iberiotoxin (100 nM, Sigma-Aldrich), a $K_{Ca}$ channel antagonist on pial artery response to salvinorin A, cromakalim (1 µM) and calcitonin-gene related polypeptide (10 nM, 1 µM), a $K_{ATP}$ agonist, and NS1619 (10 nM, 1 µM), a KCa channel agonist, were also determined. Finally, the effect of naloxone (1 mg/kg IV) and norbinaltorphimine (1 µM topical administration, a kappa opioid receptor antagonist, on the response to the salvinorin A, methionine enkephalin (10 nM, 1 µM) and isoproterenol (10 nM, 1 µM), a beta adrenergic receptor agonist, were investigated. All tested drug solutions were made fresh on the day of use. Pial artery response to salvinorin A administrated every 2 minutes was recorded for 30 min to determine whether the sustained vascular dilatation could be achieved.

cGMP Determination

To determine the role of nitric oxide pathway on the effect of salvinorin on cerebral vasculature, CSF samples were collected for cGMP determination before and after salvinorin A administration with or without L-NNA and norbinaltorphimine pretreatment. Commercially available ELISA kits (Enzo Life Sciences International, Inc. Plymouth Meeting, Pa.) were used to quantify cGMP concentration.

Salvinorin a on Constricted Vessels

To test the cerebrovascular effect of salvinorin during elevated cerebrovascular tone, we induced vasoconstriction via hypocarbia ($PaCO_2$ reduced by 20-30% for 10 min) and endothelin (0.1 pM). The pial artery diameter were monitored at baseline, after hypocarbia or administration of endothelin, and after salvinorin A (10 nM, 1 µM) administration (n=4 for hypocarbia, n=5 for endothelin).

Statistical Analysis

All data (diameters and cGMP) were analyzed using ANOVA with repeated measures followed by Bonferroni post hoc test (two-tailed) with a Statistical Package for the Social Sciences (SPSS) of 10.0. A level of p<0.05 was considered statistically significant. Values are represented as mean±SEM of the absolute value; or as percentage changes from the baseline values. Distributions of all values were evaluated by histograms.

Results

Dilation Effect and the Role of Nitric Oxide Pathway

Figure 2:
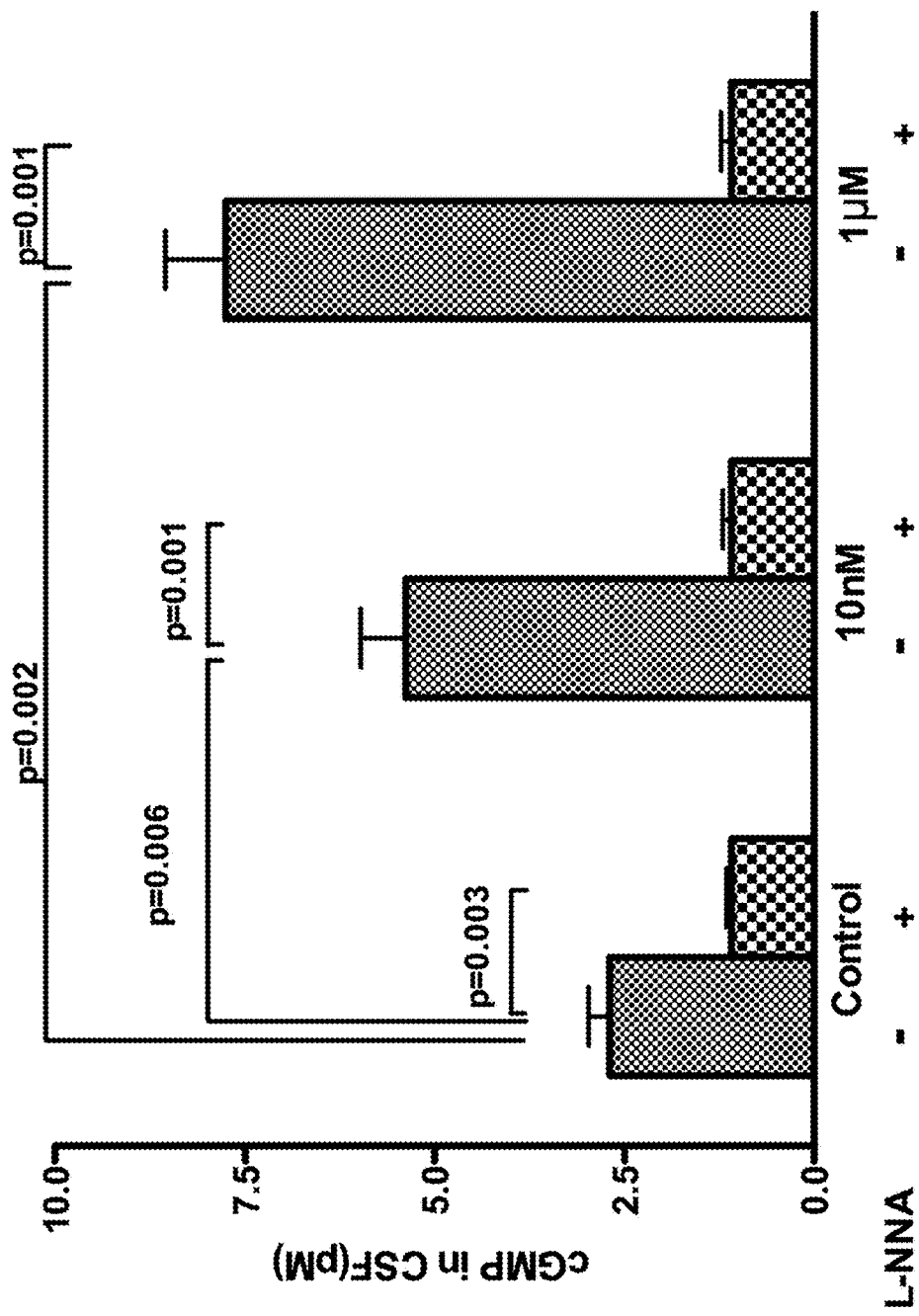
FIG. 2. Salvinorin A increases cGMP in the CSF, and L-NNA blocked salvinorin induced cGMP elevation and vascular dilation (n=5). cGMP: cyclic guanosine monophosphate; CSF: cerebrospinal fluid; L-NNA; N(G)-nitro-L-arginine FIG. 3. Glibencamide, but not Iberiotoxin, blocked the dilation effects of salvinorin A. Glibencamide given with Iberiotoxin in any sequences blocked the dilation effects of salvinorin (n=5). S: salvinorin A; Glib: glibencamide; Iberi: Iberiotoxin; *: the agent administered first.

Salvinorin A dose dependently (10 nM, 1 µM) dilated the pial artery of piglet as shown in FIG. 1A. The dilation effect is observed immediately after salvinorin administration and the duration of dilation lasted less than 5 minutes for both doses. When the salvinorin A was administration administered every 2 minutes, sustained dilation effects was observed as shown in FIG. 1B. The dilation response was abolished by L-NNA, the NOS inhibitor, but not 7-nitroindazole (100 nM), the antagonist of neuronal NOS (nNOS) (FIG. 1A,C). Dilation response to SNP was not affected by L-NNA (FIG. 1A). SNP (100 pM) had no effects on the pial artery, but it restored the constriction induced by L-NNA. However, it didn't restore the dilation response of salvinorin A blocked by the L-NNA (FIG. 1D). Dilation in response to salvinorin A was associated with elevated cGMP in CSF, and L-NNA blocked the elevation of the cGMP (FIG. 2). No significant blood pressure changes occurred during salvinorin administration.

$K_{ATP}$ Channel, not KCa Channel, Involved in the Dilatation Effect

Figure 3:
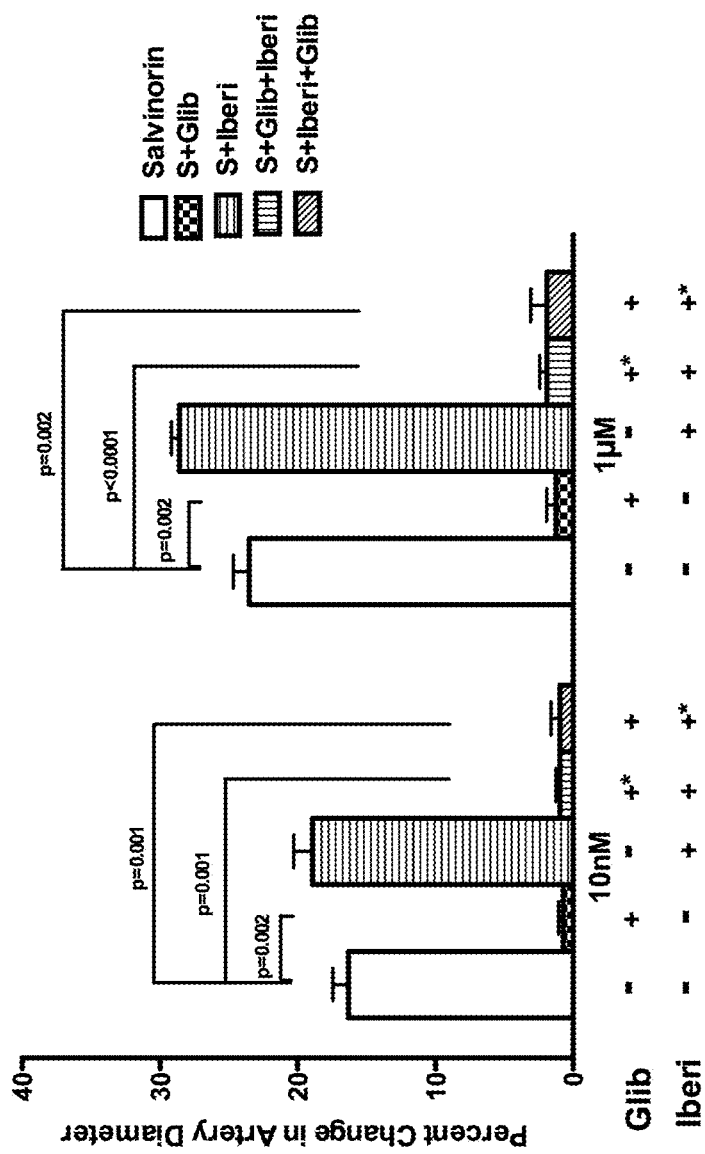
Figure 4:
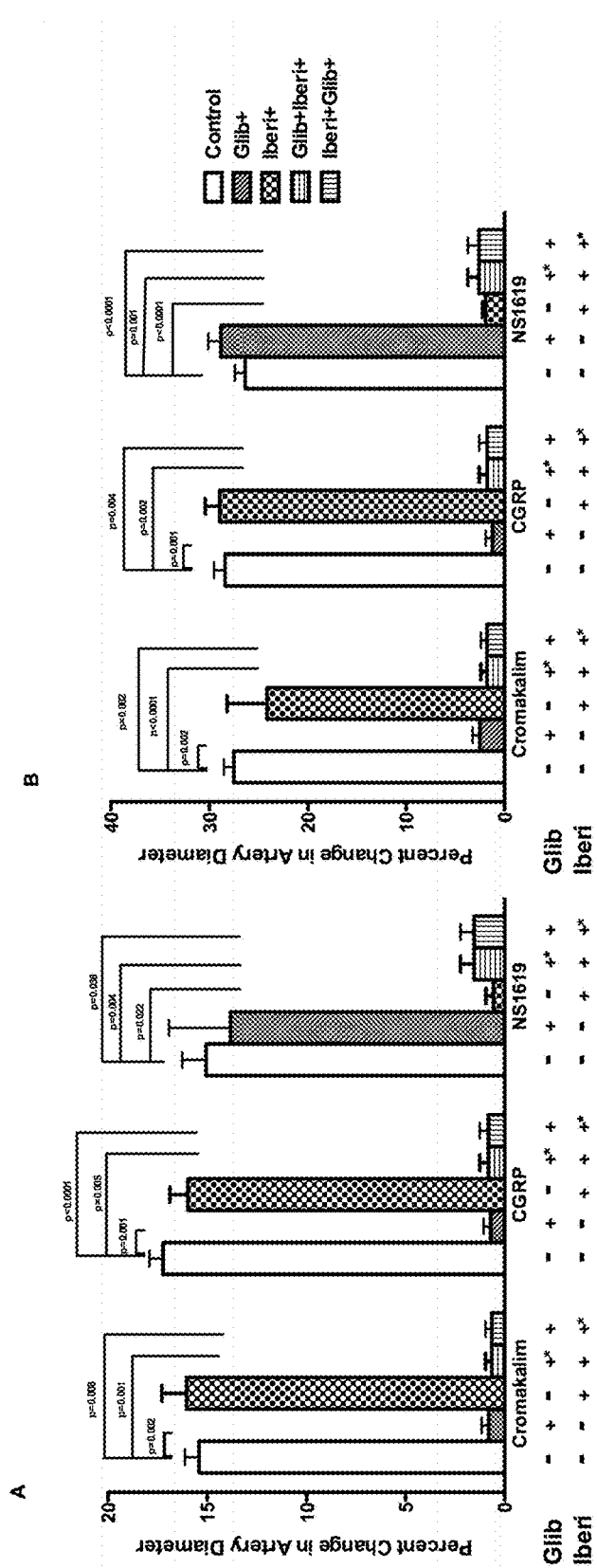
FIG. 4. Glibencamide, but not iberiotoxin, blocks the dilation effects of cromakalim and CGRP. Iberiotoxin but not glibencamide block the dilation effects of NS1619. Panel A demonstrates the effects of 10 nM of cromakalim, CGRP and NS1619, in the presence or absence of the pretreatment agents. Panel B demonstrates the effects of 1 M of cromakalim, CGRP and NS1619 (n=5). Glib: glibencamide; Iberi: Iberiotoxin; CGRP: calcitonin-gene related polypeptide; *: the agent administered first.

Glibenclamide (100 nM), the $K_{ATP}$ channel inhibitor, but not iberiotoxin (100 nM), the Ca2+-activated K+(KCa) channel inhibitor, blocked the dilation effects of salvinorin A. Glibenclamide with iberiotoxin in any sequence also blocked the dilation induced by salvinorin A (FIG. 3). Glibenclamide (100 nM) but not iberiotoxin (100 nM) blocked the dilation in response to cromakalim (an agonist of $K_{ATP}$ channel, 10 nM and 1 µM) and calcitonin-gene related polypeptide (another $K_{ATP}$ channel agonist, 10 nM and 1 µM); iberiotoxin (100 nM) but not glibenclamide (100 nM) blocked the dilation effects of NS1619 (KCa channel agonist, 10 nM and 1 µM) (FIG. 4).

Figure 5:
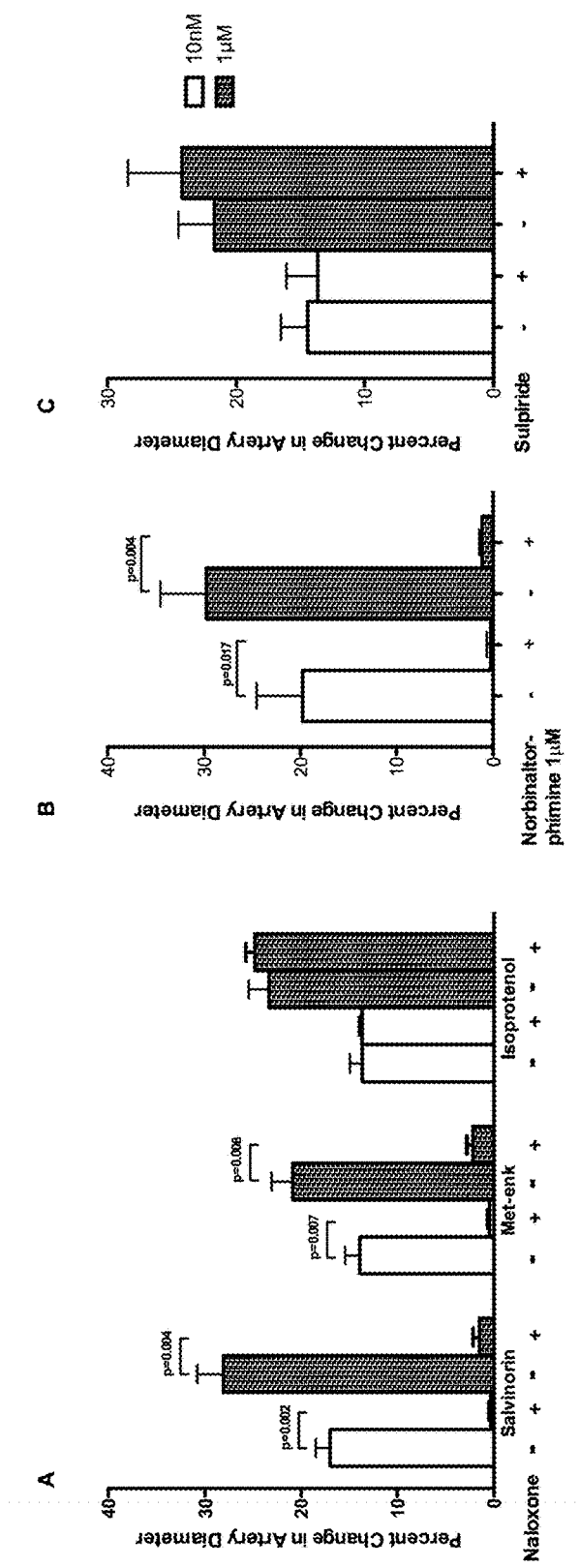
FIG. 5. Naloxone and norbinaltrophimine but not sulpiride block the dilation effects of salvinorin A. Panel A: Naloxone and Met-enkaphlin but not isoprotenol block the dilation effects of salvinorin A. Panel B: norbinaltrophimine block the dilation effects of salvinorin A. Panel C: Sulpiride didn't block the dilation effects of salvinorin A (n=5). Met-enk: methionine enkephalin.

Opioid Receptor not Dopamine Receptor D2 Antagonist Blocks Dilation Effect of Salvinorin Norbinaltorphimine, the kappa opioid receptor selective antagonist, and naloxone blocked the dilation effects to salvinorin A and methionine enkephalin. The response to isoproterenol was unaffected (FIG. 5A,B). Sulpiride, the dopamine receptor (D2) antagonist, had no effect on the dilation response to the salvinorin A (FIG. 5C). Norbinaltorphimine blocked the elevation of cGMP in the CSF from salvinorin A administration. There were no differences among the levels of cGMP before and after salvinorin A (10 nM and 1 µM) administration with norbinaltorphimine pretreatment (p=1).

Salvinorin Dilates Pial Arteries in Elevated Cerebrovascular Tone Conditions

Figure 6:
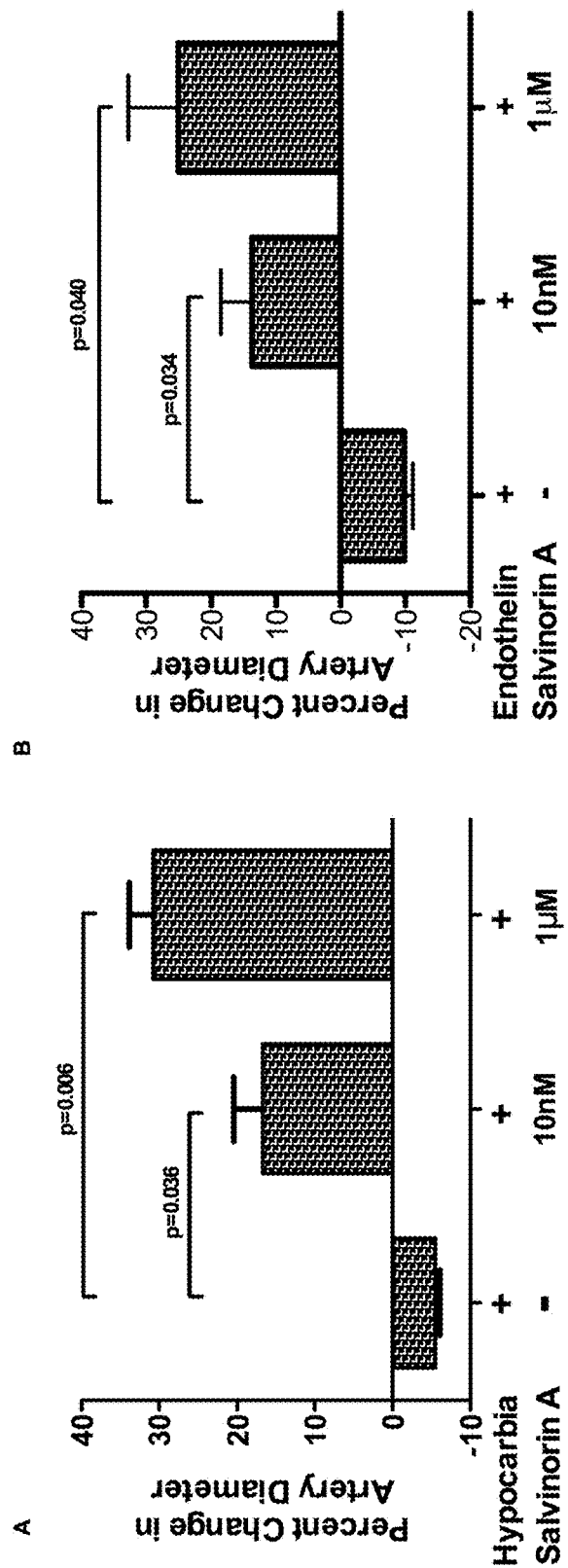
FIG. 6. Salvinorin A dose dilated the constricted pial artery induced by hypocarbia and endothelin for both tested dose in a dose-dependent manner. Panel A: hypocarbia (n=4); Panel B: Endothelin (n=5).

Hypocarbia and endothelin significantly decreased the diameter of pial arteries (FIG. 6). Salvinorin dilated pial arteries under elevated tone conditions similar to that observed under normocapnic (resting tone) conditions (FIG. 6). No significant differences between responses of small artery and arteriole were observed in any of above experiments, thus, only changes in small artery was presented.

Discussion

In this Example, salvinorin A is demonstrated to be a potent pial artery dilator in piglet in normal and vessel constricted conditions induced by endothelin and hypocarbia. The dilatation effect was observed immediately after salvinorin administration, lasted less than 5 min for both tested doses, and was dose-dependent. Sustained dilation effects of salvinorin A was observed with continuous administration. The activation of the opioid receptor, NOS and $K_{ATP}$ channel were involved in the signal pathway of such dilation effects.

It had been demonstrated that U50488, an exogenous KOR agonist, and dynorphin, an endogenous KOR agonist, dilated the pial artery. It has also been demonstrated that U50488 dose-dependently relaxed the isolated aortic artery in rat. Different than other KOR agonists, the dilatation effect of salvinorin is very short-lived, less than 5 minutes. This is the shortest acting agent so far among kappa agonists, which is an important pharmacological feature for many clinical medications for easy management and titration in perioperative settings and critical care. To achieve longer effects, infusion is the most common technique to be used in clinical anesthesia. In this Example, we found that persistent vascular dilatation can be achieved via continuous administration.

The unique structure of salvinorin A, not tachyphylaxis, contributes to its short acting character, because continuous administration results in a sustained dilatory effect. The ester linkage in its structure can be easily metabolized by esterase in the blood and tissues. One group demonstrated that carboxylesterase mainly involved in salvinorin A hydrolysis in rat plasma and the degradation products include salvinorin B and the lactone-ring-open forms of salvinorin A, both of which are not pharmacologically active.

Similar to other KOR agonists, the activation of NOS, $K_{ATP}$ channels and opioid receptors mediated the dilation effects of salvinorin A. Another group has demonstrated that selective KOR agonist BRL 52537 protected the ischemia brain via attenuating nitric oxide production in ischemic striatum. It was proved that the neuroprotection of BRL 52537 was lost in nNOS null mice. Therefore, the KOR agonist BRL 52537 attenuated nNOS activity and ischemia-evoked nitric oxide production. However, in this Example, pial artery dilation to salvinorin A was abolished by the L-NNA, a non-specific NOS inhibitor, but not 7-nitroindazole, a selective nNOS antagonist, indicating that nNOS is not involved in the dilative effective of salvinorin A. Since sub-threshold amount of the nitric oxide donor, SNP, failed to restore the dilation response, the elevation of cGMP in CSF is likely due to stimulation rather than inhibition of nitric oxide production, direct activation of salvinorin on endothelial NOS rather than as a permissive enabler.

$K_{ATP}$ channels activation may result in hyperpolarization of the membrane of vascular smooth muscle cell. Membrane potential changes would then regulate muscle relaxation through alterations in $Ca^{2+}$ influx through voltage-dependent $Ca^{2+}$ channels. This Example demonstrates that salvinorin A activates the $K_{ATP}$ channel directly or indirectly. Different from many other agents that can activate $K_{ATP}$ channel, salvinorin A can easily penetrate the blood-brain barrier. Since the $K_{ATP}$ channel plays a crucial protective role against brain injury from hypoxia, ischemia or metabolic inhibition, salvinorin A can be a neuro-protective agent for clinical use.

Although salvinorin A has been proved to have a high affinity for dopamine D2 receptors, sulpiride, the dopamine D2 receptor selective antagonist, has no effects on the dilation effects of salvinorin A. On the contrary, naloxone and norbinaltorphimine, the kappa opioid receptor selective antagonist, abolished the vascular dilative effects of salvinorin A, suggesting the important role of kappa receptor rather than the dopamine D2 receptor.

The vascular dilative effect observed in normal and constricted cerebral vessels by both hypocarbia and endothelin can allow for its clinical application to treat cerebral vessel spasm in many clinical situations including migraine and cerebral vascular spasm after subarachnoid hemorrhage in which increase of endothelin plays an important role. Similar to other short acting agents, continuous infusion could be used to titrate and achieve sustained effects by adjusting dosage.

In this Example, newborn piglets were used as the study subject. The gyrencephalic brain of pig has more white than gray matter which is selectively vulnerable to injury similar to the human, and also similar in maturity. The newborn piglet was also used because it is large enough for easy cranial window placement and vascular visualization. The newborn's cerebral vascular responses are similar to that in human subjects in many clinical situations.

In conclusion, salvinorin A is a fast and short acting potent pial artery dilator in piglet in normal and vessel constricted conditions induced by endothelin or hypocarbia. The mechanism involves the activation of NOS, $K_{ATP}$ channel and kappa receptor. These findings show the clinical value of salvinorin A in the setting of demanding cerebral vascular dilation.

Example 2

Salvinorin a Administration after Global Cerebral Hypoxia/Ischemia Preserves Cerebrovascular Autoregulation Via Kappa Opioid Receptor in Piglets The neuronal death and behavioral dysfunction caused by hypoxia/ischemia (HI) induced brain injury is not uncommon during the perinatal period. Worldwide, 23% of all new birth deaths are associated with asphyxia and 30% of children who's births involved moderate hypoxic-ischemic encephalopathy (HIE) may develop mental retardation, learning difficulties, and other disabilities. Unfortunately, there is no medication available to manage this devastating situation.

KOR agonists cause dilation of cerebral vessels, a key feature required to maintain cerebral autoregulation and reduce brain injury from ischemia. After ischemia, cerebral autoregulation is impaired, resulting in decreased cerebral blood flow and neuron death. We have demonstrated in a piglet model that administration of salvinorin A before global HI preserved the autoregulation of the cerebral artery, an important mechanism for the preservation of neuronal integrity. this Example, we hypothesized and tested whether administration of salvinorin A after HI could preserve cerebral autoregulation via the KOR and ERK pathway.

Materials and Methods

Salvinorin A (purity ≥98%) was obtained from Chroma-Dex, Inc. (Irvine, Calif., USA). Isoproterenol (ISO), nor-binaltorphimine (Nor-BIN) were obtained from Sigma-Aldrich (MO, St. Louis, Mo., USA). All other chemicals (reagent grade) were obtained from Sigma as well.

Animal and Surgery for Closed Cranial Window

Newborn pigs (1-5 days old, 1.2-1.5 kg) of both sexes were used in this study. The animal experimental protocol was approved by the Institutional Animal Care and Use Committee of the University of Pennsylvania. As described previously, Isoflurane (1 to 2 minimum alveolar concentration) was initially used for anesthesia induction, followed by α-chloralose (30-50 mg/kg supplemented with 5 mg/kg/hr intravenously) for maintenance of anesthesia. After tracheotomy, the animals were initially ventilated with room air and kept warm with heating pad to maintain the rectal temperature at 37-39° C. Bilateral femoral arteries were catheterized to monitor the blood pressure, blood gas tensions and pH. The femoral vein was catheterized for medication administration. A closed cranial window, consisting of a steel ring with a glass cover slip, connecting to 3 ports, was placed for direct pial artery visualization and diameter measurement. Small pial arteries (120 to 160 μm) and arterioles (50 to 70 μm) were identified under a microscope, visualized on a monitor connected to the microscope, and measured via a video microscaler (model VPA 550, For-A-Corp., Los Angeles, Calif.). The ports attached to the cranial window ring fit 17-gauge hypodermic needles for CSF sampling, washout, and drug administration. Cortical periarachnoid CSF was collected at baseline and 60 min after HI for ERK activity analysis.

HI Induction

Hypoxia was induced for 10 minutes by switching room air to N2 for ventilation, followed by restoring ventilation to room air. Global cerebral ischemia was then induced by infusing saline through a hollow bolt in the cranium to maintain intracranial pressure higher than the mean blood pressure for 20 min Global cerebral ischemia is confirmed when the blood flow in pial arteries were stopped visible on the monitor connected to the microscope over the cranial window. In order to avoid Cushing response (arterial pressure rising dramatically because of high intracranial pressure), blood was withdrawn when necessary to maintain the mean arterial blood pressure below 100 mmHg. The blood was returned via femoral vein at the end of ischemia.

Drug Treatments

Four groups of i.v. drug administration were performed after HI (n=5 in each group): (1) DMSO group: with DMSO (vehicle of salvinorin A) 1 µl/kg administered immediately after HI; (2) SA 0 min group: with salvinorin A (1 µg/µl in DMSO) 10 µg/kg immediately after HI; (3) SA 30 min group: with salvinorin A (1 µg/µl in DMSO) 10 µg/kg 30 min after HI; (4) SA+Norbin group: with salvinorin A (10 µg/kg) and nor-BIN (1 µM, topically injected through one port of cranial windows) immediately after HI.

Pial Artery Responses

Pial artery responses to hypercapnia, hypotension and isoproterenol (10 nM, 1 µM) were obtained before HI and 60 minutes after HI as previously described. Isoproterenol was used as a positive control since it is a short acting agent and its vascular dilatation effect in such model is well established in our lab. Two levels of hypercapnia ($PaCO_2$ of 50 to 60 mmHg for low level, 70 to 80 mmHg for high level) were produced by inhalation of high concentration $CO_2$ mixture gas (10% $CO_2$; 21% $O_2$; 69% $N_2$). Two levels of hypotension were produced by the rapid withdrawal of either 5-8 or 10-15 ml/Kg blood from the femoral artery to induce moderate and severe hypotension (25% decrease in mean blood pressure as moderate and 45% decrease as severe). Such decreases in blood pressure were maintained constantly for 10 min by withdrawal or reinfusion of additional blood.

ERK Activity Measurement

ERK activity were then determined from frozen CSF samples described above. The levels of pERK and ERK were measured by ELISA kits (Enzo Life Sciences International, Inc., Plymouth Meeting, Pa.).

Statistical Analysis

The data of pial artery diameter were analyzed by repeated-measures ANOVA followed by Bonferroni method as post hoc tests. One way ANOVA was used to compare the ERK activity changes (quantified as the ratio of pERK over ERK) in each group before and 60 min after HI and in the groups with or without salvinorin A administration. The baseline data were excluded in the repeated-measures analysis (Graph Pad Prism version 5.02). An alpha level of $P<0.05$ was considered significant in all statistical tests. Values are represented as means±standard error.

Results

Figure 13:
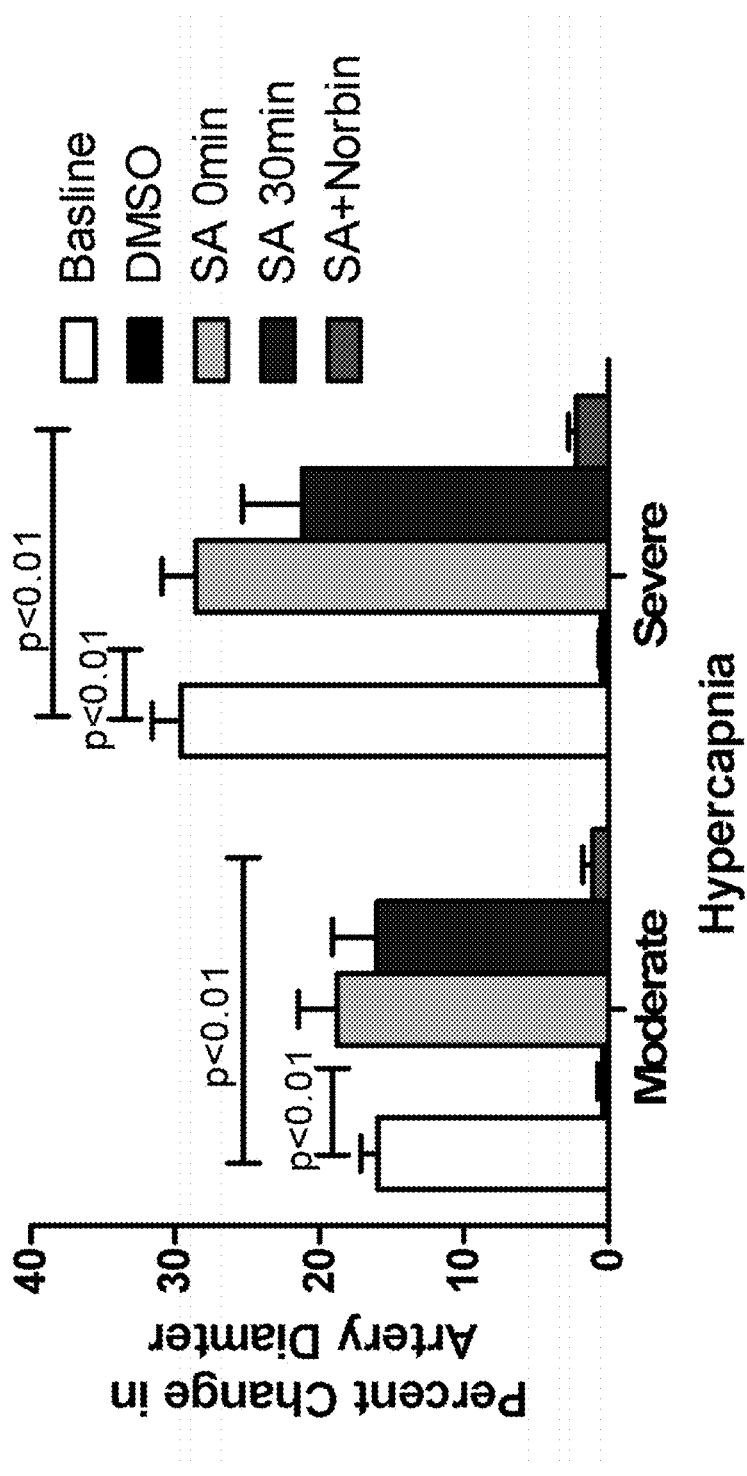
FIG. 13: Effects of post HI salvinorin A administration on pial artery dilation to hypercapnia. HI with DMSO impaired dilation of pial artery to hypercapnia. SA administered at onset and 30 min after HI preserved the dilation of pial artery to moderate and severe hypercapnia, which were blunted by norbinaltorphimine (Norbin). N=5 in each group. Percentage change=(diameter after hypercapnia-diameter before hypercapnia)/diameter before hypercapnia)×100. SA: Salvinorin A; Moderate: hypercapnia with $PaCO_2$ of 50 to 60 mmHg; Severe: hypercapnia with $PaCO_2$ of 70 to 80 mmHg.

Salvinorin a Preserves Pial Artery Autoregulation to Hypercapnia after Global Cerebral HI As shown in FIG. 13, the small pial artery dilated in response to two levels of hypercapnia before HI (presented as baselines). The dilatation responses to hypercapnia were blunted after HI when DMSO was administered immediately at the end of HI (ps<0.01 as compared with the baselines before HI). Administration of salvinorin A (10 µg/kg), immediately or 30 min after HI, preserved the dilation responses of pial artery to hypercapnia. Such responses were abolished completely when salvinorin A and norbinaltorphimine (nor-BIN) were co-administered 30 min after HI (ps<0.01 as compared with baselines before HI). Similar observations were obtained in pial arterioles (data not shown).

Figure 14:
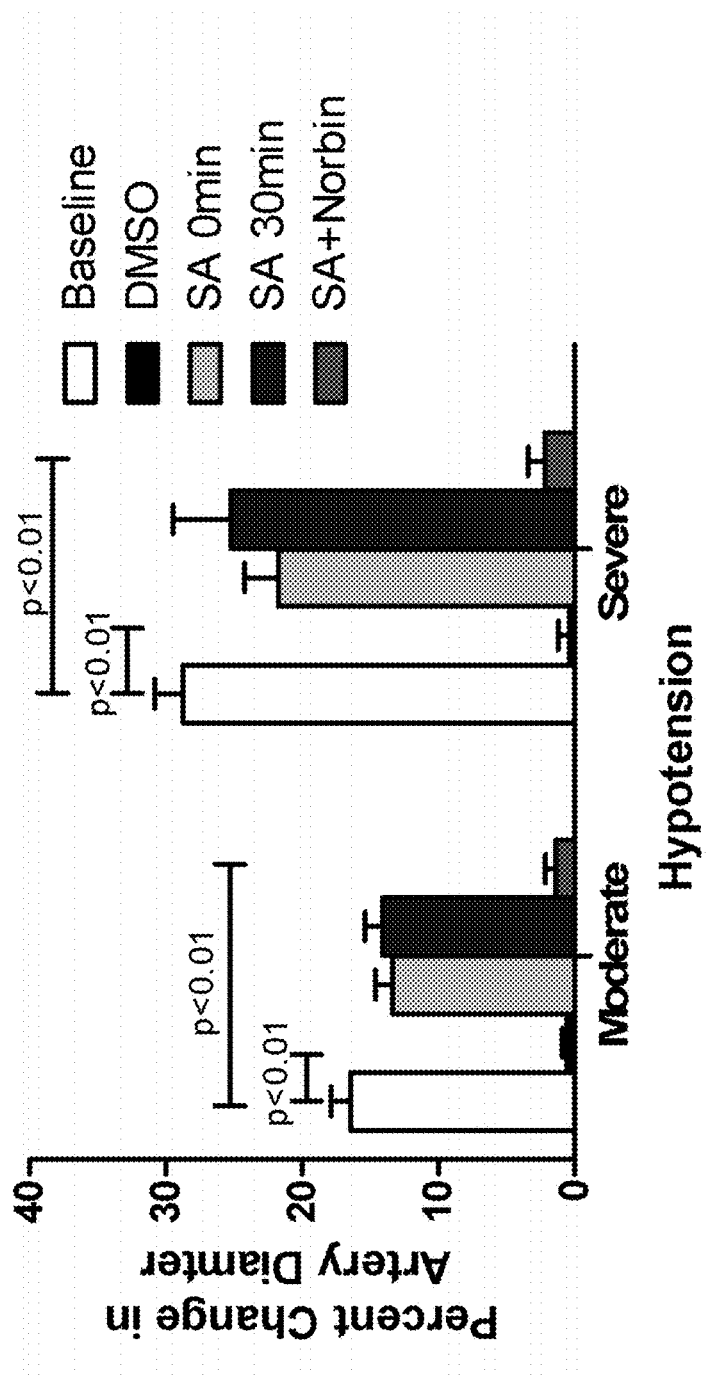
FIG. 14: Effects of post HI salvinorin A administration on pial artery dilation to hypotension. HI with DMSO damaged dilation of pial artery to hypotension. SA administered at onset and 30 min after HI preserved the dilations of pial artery to moderate and severe hypotension, which were blunted by co-administration of norbinaltorphimine (Norbin). Percentage change=(diameter after hypotension-diameter before hypotension)/diameter before hypotension)×100. N=5 in each group. SA: Salvinorin A. Moderate: 25% decrease of mean blood pressure. Severe: 45% decrease of mean blood pressure.

Salvinorin a Preserves Pial Artery Autoregulation to Hypotension after Global Cerebral HI Similar to the result of hypotension, the small pial artery dilated in response to two levels of hypotension before HI hypercapnia (presented as baselines, FIG. 14) before HI.

The dilatation responses were blunted after HI when DMSO was administered immediately at the end of HI (ps<0.01 as compared with the baselines before HI). Salvinorin A (10 µg/kg), administered immediately or 30 min after HI, preserved the dilation responses of pial artery to hypotension. Such responses to hypotension were abolished when salvinorin A and nor-BIN were co-administered 30 min after HI (ps<0.01 as compared with the baselines). Similar observations were obtained in pial arterioles.

Figure 15:
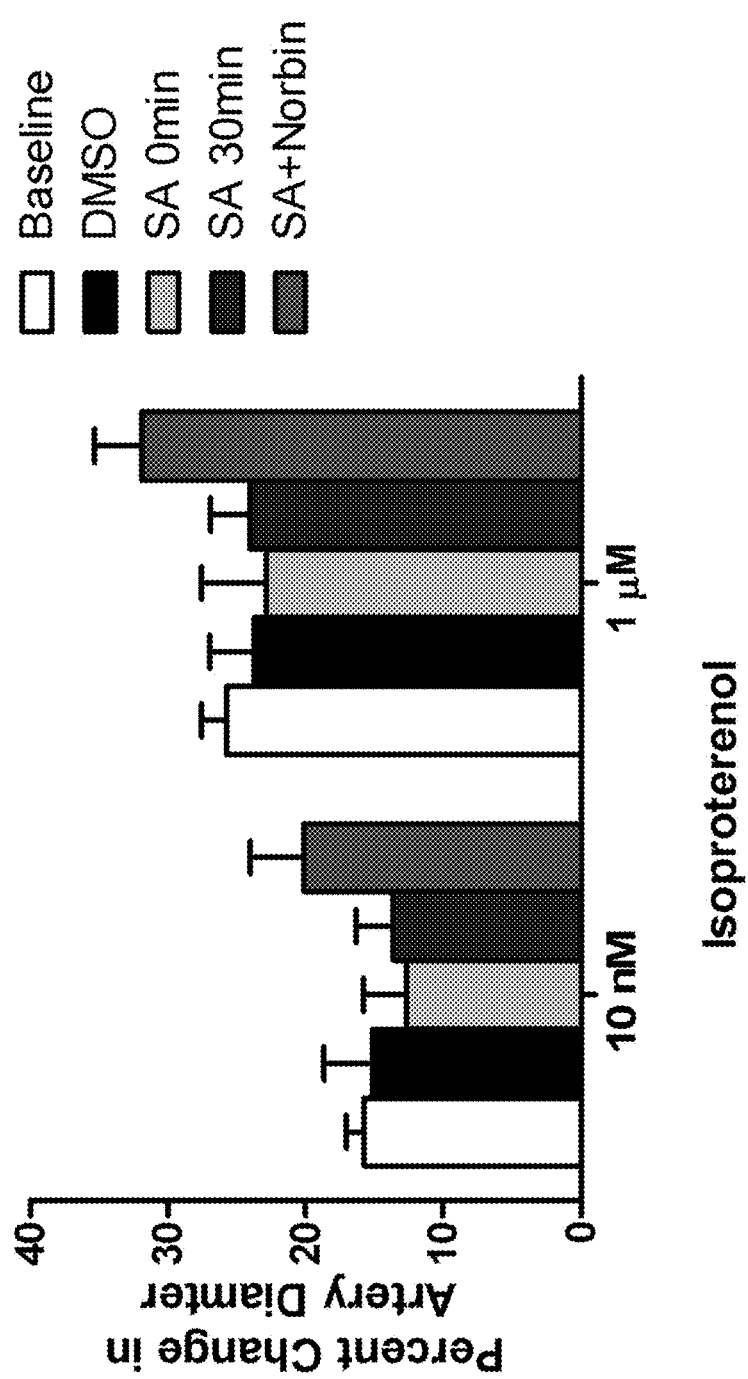
FIG. 15: Isoproterenol induced artery dilation was independent of KOR or ERK signaling. Effects of isoproterenol (10 nM, 1 µM) on pial artery diameter before (baseline) and after HI did not change significantly in the presence and absence of various interventions, compared to baseline p>0.05. N=5 in each group. Percentage change=(diameter after isoproterenol-diameter before isoproterenol)/diameter before isoproterenol)*100; SA: Salvinorin A; Norbin: norbinaltorphimine FIG. 16. Salvinorin A administration blocked the elevated CSF ERK activity observed 1 h after HI. The ration of pERK/ERK at 1 hour after HI in the control groups (n=10, DMSO and nor-BIN groups) increased significantly compared with the baseline. The baseline for all the groups are pulled together (n=20) and the data from DMSO and nor-BIN groups were pulled together and presented as DMSO+ Norbin (n=10) to increase the power of the statistical analysis because of some large variances were observed. The elevated ERK activities were abolished in the groups with salvinorin A administrated immediately (n=5) or 30 min (n=5) after HI. Norbin: norbinaltorphimine; SA: Salvinorin A.

Pial Artery Responses to Isoproterenol Remain Unchanged in all Sets of Experiments As a positive control, pial artery responses to isoproterenol (FIG. 15) were measured and no change was observed among all groups before and after HI.

ERK Signaling is Involved in the Preservation Effects of Salvinorin A

Figure 16:
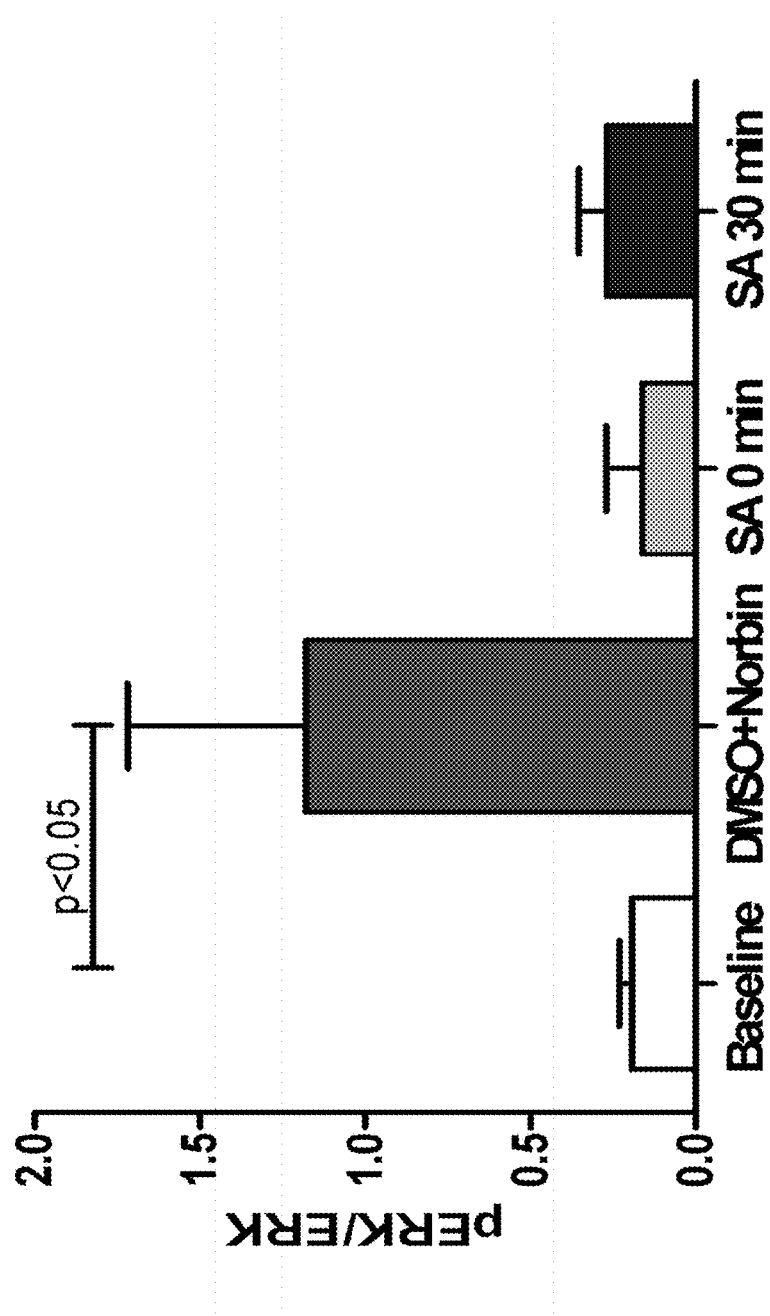

The ERK activities are quantified as the ratio of pERK/ERK levels in CSF. The ERK activity data in groups without salvinorin effects (DMSO group and SA+Norbin group; renamed as DMSO+Nornin group) are combined. As indicated in FIG. 16, the ERK activity in groups without salvinorin increased significantly 60 min after HI (p<0.05 as compared with pre-HI baseline). The ERK activity of salvinorin A administration groups reduced to the baseline level.

Discussion

There are three new findings from this Example. First, administration of salvinorin A instantly or 30 minutes after HI preserves the pial artery dilation response to hypercapnia and hypotension. Second, the preservation effects of salvinorin A were blunted KOR antagonist, nor-BIN. And third, salvinorin A blocked the increase of CSF ERK activity after HI.

The Problem of Cerebral HI and the Potential Role of KOR Agonist

Both birth asphyxia and pediatric ischemic stroke are the common complications of childbirth. Perinatal HI, occurring in both these complications, can induce severe and permanent neuropsychological deficits, including delayed cognitive and behavioral development, mental retardation, cerebral palsy, and epilepsy, which is devastating for the patients, the families, and society. Unfortunately, there is no medication available for effective perinatal HI management. Hypothermia is the only treatment for HIE to reduce negative complications. But it is not widely accepted in clinical practice or recommended to combine with pharmacologic agents. Recombinant tissue type plasminogen activator (t-PA), a FDA approved treatment for acute ischemic stroke, showed adverse effects including increased stroke infarct volume in mice subjected to induced stroke and impaired cerebral hemodynamics.

The neuroprotective effects of KOR agonists have been demonstrated in other ischemia animal models. For example, KOR agonist BRL 52537 and CI-977 reduces cortical damages, including brain swelling and infarction volumes, in response to different levels of ischemia when administered 30 min before or up to 6 hours after the insult. These findings suggest that KOR agonists could be a valuable alternative medication for HI treatment in clinical settings.

Salvinorin a as a Novel Medication

Although KOR agonists exhibit tremendous therapeutic value, most KOR agonists have not been used in clinical settings because of their intrinsic characteristics as opioids, (low selectivity and/or lack of an acceptable safety profile). Unlike other opioid KOR agonists, salvinorin A is the most potent, highly selective, and the only non-opioid KOR agonist known to be derived from natural sources. Salvinorin A is the active component of *Salvia divinorum*, a naturally abundant perennial herb that has been consumed by humans for recreational and sacred purposes for several centuries. Many intrinsic characteristics of this compound make it a potential therapeutic medication for various neurological conditions. Those characteristics include its ability to be extracted and purified from an abundant plant or produced via synthesis, a rapid onset of action, lipid solubility, easy passage through the blood brain barrier, sedative and antinociceptive effects (features of particular relevance for the critically ill patient), negative pathological findings in vital organs with high dose or prolonged exposure (non-toxic), no respiratory depression and no frank hallucinatory or dysphoric effects. Salvinorin A has been evaluated as a potential medication for depression. In addition to our findings demonstrating the protective effect of salvinorin A administration before HI insult, we have now demonstrated that salvinorin A administration (up to 30 min) after HI insult preserved the autoregulation of pial artery. This protective effect was abolished by the addition of the KOR antagonist, nor-BIN, which indicates that the protective effect of salvinorin A is mediated via KOR. Various studies have proven that autoregulation, a key protective mechanism of the brain, tends to worsen after cerebral HI. Autoregulation of cerebral vascular tone is a key protective mechanism of the brain. And impaired compensatory cerebrovasodilation during hypotension contributes to worsened outcome in the setting of ischemic stroke.

The Role of ERK Signaling

ERK signaling stimulated by cerebral ischemia/reperfusion is a crucial pathway for HI injury. We have demonstrated that ERK activity increases after HI and the increase relates to neuronal impairment of HI, and inhibition of such an increase is associated with neuroprotective responses against ischemia, which may be associated with the reduction in apoptosis. In this Example, HI induced increases in the CSF ERK activities were blocked by salvinorin A, which promoted protection of cerebral autoregulation post insult. It is worth noting that the role of ERK signaling in HI may be different before and after HI insult. Activation of ERK signaling may be related to the protective effects of preconditioning. Upregulating ERK signaling induced by preconditioning reduces neuronal apoptosis in stroke and activation of ERK signaling in the hippocampus after sublethal ischemia correlates with neuroprotection induced by preconditioning. These results are consistent with our work demonstrating that pre-injury administration of salvinorin A is protective of the impairment of cerebral autoregulation post insult. In conclusion, Salvinorin A administration 0 and 30 min after HI preserves autoregulation of the pial artery to hypercapnia and hypotension via KOR and the ERK pathway in a piglet model.

Example 3

Salvinorin a Pretreatment Preserves Cerebrovascular Autoregulation after Brain Hypoxic/Ischemic Injury Via ERK/MAPK in Piglets Cerebral hypoxia/ischemia because of the interruption of cerebral blood flow during cardiopulmonary bypass with deep hypothermia circulation arrest (DHCA) surgery for congenital cardiac surgery is a significant clinical issue. Fifty percent of children with complex congenital heart disease undergoing cardiopulmonary bypass with DHCA have developmental deficits, such as disabilities in speech and attention deficit disorder by school age. Cerebral hypoxia/ischemia occurred during DHCA is predictable, thus, it is possible to minimize the brain injury induced by ischemia with pharmacologic approaches. Unfortunately, no pharmacological agent with proven clinical benefit has been identified yet.

Loss of cerebral vascular autoregulation is one of the key features of cerebral hypoxia/ischemia. The loss of autoregulation to hypotension could result in a pressure passive cerebral circulation, which may decrease cerebral blood flow and further aggravate brain ischemia. Loss of cerebrovascular regulation to hypercapnia also contributes to the development of the pressure passive circulation and periventricular leukomalacia. Thus, preservation of cerebral vascular autoregulation from ischemia is very important to reduce the brain injury from ischemia. We have demonstrated that salvinorin A, an active component of *Salvia divinorum* and a non-opioid kappa opioid receptor (KOR) agonist, is a potent cerebral vascular dilator in normal and pathological conditions. Thus, salvinorin A can protect cerebral vasculature from ischemia. Unlike other KOR agonist, salvinorin A has long been used by different ethnic groups for various purposes, including spiritual experiences and "treating" illnesses, indicating its high potential as a clinically acceptable medication.

It has been demonstrated that systemic administration of KOR agonists has neuro-protective effects in animal models of cerebral ischemia. KOR agonist could activate mitogen-activated protein kinase (MAPK). MAPK is a key intracellular signaling system, which includes extracellular signal regulated kinase (ERK), c-Jun-N-terminal kinase (JNK) and p38. It was demonstrated that a prolonged and persistent activation of the ERK cascade is an important contributory mechanism of cerebral ischemic preconditioning. This pathway is also involved in many other forms of pharmacological preconditioning, such as isoflurane and sevoflurane. Thus, salvinorin A may generate cerebral protective effects via this pathway. Based on the above evidence, we hypothesized that salvinorin A pretreatment might preserve autoregulation of pial vessel to hypotension and hypercapnia from hypoxia/ischemia via activation of MAPK.

Methods

Salvinorin A (purity ≥98%) is from ChromaDex, Inc. (Irvine, Calif., USA). Isoproterenol, U0126, sp600125 and sb203580 are obtained from Sigma-Aldrich (MO, St. Louis, Mo., USA). All other chemicals were also obtained from Sigma and were of reagent grade.

Animals and Surgery

One to five days old piglets were used. Protocols were approved by the Institutional Animal Care and Use Committee of the University of Pennsylvania (Philadelphia). Isoflurane (1-2 minimum alveolar concentration) was initially used for induction, followed by alpha-chloralose for maintenance of anesthesia (30-100 mg/kg, supplemented with 5-30 mg/kg every 20-30 min IV). After tracheotomy, piglets were mechanically ventilated with room air and kept warm with a heating pad, maintaining rectal temperature at 37 to 39° C. Femoral arteries were cannulated for continuous blood pressure monitoring or intermittent blood gas monitoring, and the femoral vein was catheterized for medication administration. As described previously (21), a closed cranial window was placed for direct pial artery visualization and diameter measurement (21). Small pial artery (120 to 160 μm) and arteriole (50 to 70 μm) are identified under microscope, visualized on a monitor connected to the microscope, and measured via a video microscaler (model VPA 550, For-A-Corp., Los Angeles, Calif.). The cranial window is a steel ring with a glass cover slip, connecting to three ports for cerebrospinal fluid (CSF) sampling, washout and medicine administration. Cortical periarachnoid CSF was collected through one of the above ports at baseline and 30 minutes after administration of salvinorin A or U0126 plus salvinorin A for ERK/MAPK analysis.

Protocol

Hypoxia was induced for 10 minutes by switching room air to N2 for ventilation, followed by restoring ventilation to room air; and then global cerebral ischemia was induced by infusing saline through a hollow bolt in the cranium to maintain intracranial pressure higher than the mean blood pressure for 20 min Global ischemia is confirmed when the blood flow in pial artery stopped, visualized on the monitor connected to the microscope over the cranial window. In order to avoid Cushing response (arterial pressure rising dramatically because of high intracranial pressure), blood was withdrawn when necessary to maintain mean arterial blood pressure no higher than 100 mmHg. The blood was returned via femoral vein at the end of ischemia.

Five sets of experiments were performed (n=5 in each set of experiment): (1) hypoxia/ischemia with vehicle of salvinorin A, DMSO, 1 μl/kg administrated 30 minutes before hypoxia/ischemia; (2) hypoxia/ischemia with salvinorin A, 1 μg/μl in DMSO, 10 μg/kg i.v.; (3) hypoxia/ischemia with salvinorin A (10 μg/kg i.v.) and U0126 (1 mg/kg, i.v.), an inhibitor for the protein kinase upstream of ERK, (4) hypoxia/ischemia with salvinorin A and sp600125 (1 μM, topically injected through one port of cranial windows), an inhibitor of JNK, (5) hypoxia/ischemia with salvinorin A and sb203580 (10 μM, topically injected through one port of cranial windows), an inhibitor of P38. U0126, sp600125 and sb203580 are administrated 30 minutes before salvinorin A. Sp600125 and sb203580 were co-administered with the vasoactive stimulus so as to have continued exposure of the cerebral cortical surface after injury.

Hypercapnia ($PaCO_2$ of 50 to 60 mmHg for low level, 70 to 80 mmHg for high level) was produced by inhalation of high concentration $CO_2$ mixture gas (10% $CO_2$; 21% $O_2$; 69% $N_2$). Hypotension was produced by withdrawing blood from the femoral artery (25% decrease in mean blood pressure as moderate and 45% as severe). Pial artery responses to hypotension, hypercapnia, and isoproterenol (10 nM, 1 μM) were obtained before hypoxia/ischemia and 60 minutes after injury as described previously.

ERK and pERK Measurement

To test the role of ERK on the observed effects of salvinorin A on brain hypoxia/ischemia, CSF samples were collected for MAPK. MAPK isoforms were measured by commercially available ELISA kits (Enzo Life Sciences International, Inc., Plymouth Meeting, Pa.).

Statistical Analysis

Data obtained for the investigation of the effects of cerebral hypoxia/ischemia on pial artery responses to hypercapnia, hypotension, and isoproterenol on pial artery diameter were analyzed by repeated measures ANOVA with a Greenhouse Geisser correction. Bonferroni correction was used for all post hoc analyses (10 comparisons for each stimulation). Five different treatments (DMSO, SA, SB203580, U0126, and SP600125) were as the factors for the comparisons between group and four times measure for three stimulation before and after hypoxia/ischemia was used as the repeated measure factor (5×4×3×2). The baseline was not included in the repeated measure analysis. The same statistical methods were used for the pERK/ERK data to compare the ratio changes before and after administration of salvinorin A, three different treatment (DMSO, SA and SA+U0126) as the between groups factor, times (before and 30 min after SA) as the repeated measure factor. An alpha level of $P<0.05$ was considered significant in all statistical tests. All values are represented as means±standard error. All P-values reported in this Example have been corrected for the effect of multiple comparisons. Although the sample size in this Example is rather small, there was no apparent violation of the assumptions of lack of interaction, homogeneity of variance, and normal distribution.

Results

Salvinorin a Preserved Pial Artery Autoregulation to Hypotension after Hypoxia/Ischemia.

Figure 17:
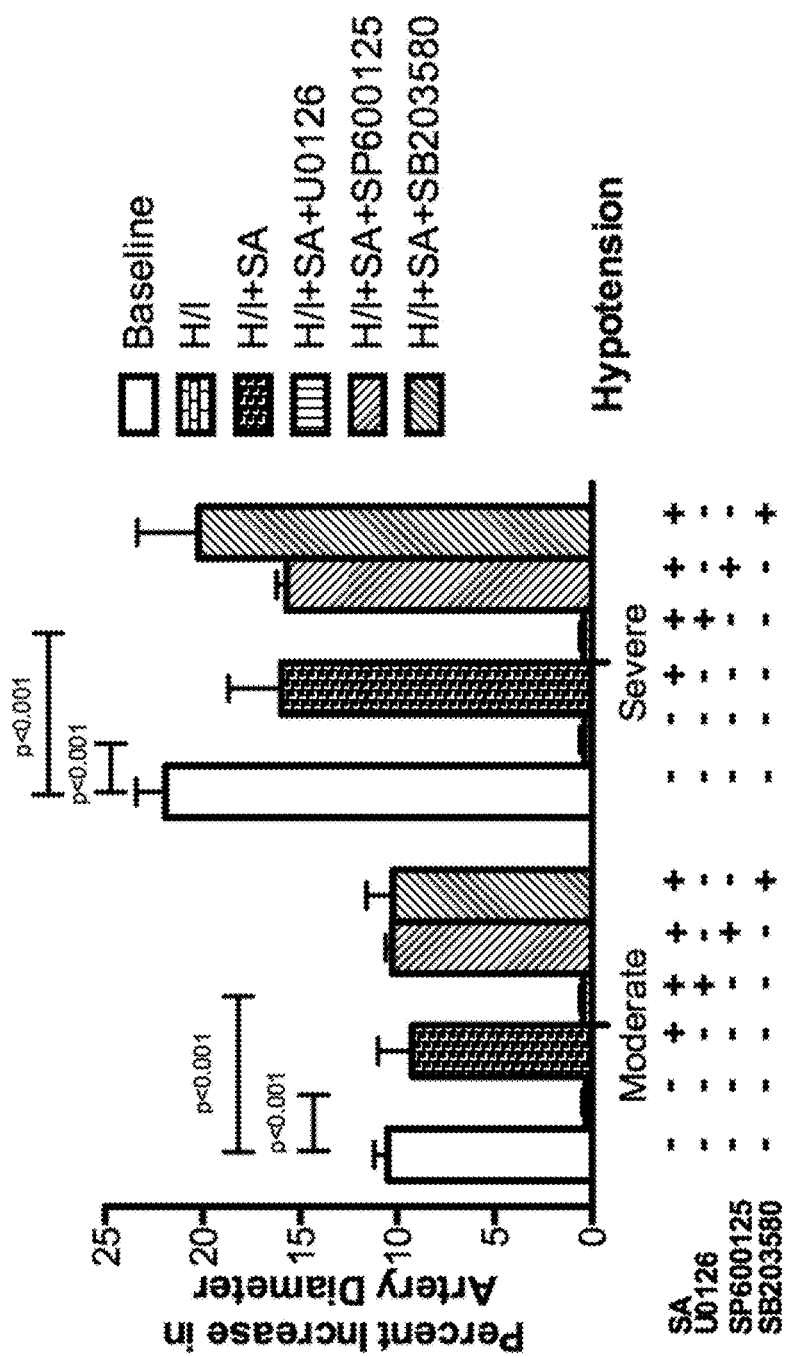
FIG. 17. Effects of hypotension on pial artery diameter before (baseline), after hypoxia/ischemia (H/I; PO2 of 35 mm Hg for 10 minutes followed by global cerebral ischemia for 20 minutes), after H/I pretreated with salvinorin A (10 μg/kg i.v.; H/I+SA) 30 minutes before H/I, and after H/I pretreated with U0126 (1 mg/kg, i.v.; H/I+SA+U0126), the antagonist of ERK, 30 minutes before salvinorin A, SP600125 (1 μM, administered topically; H/I+SA+ SP600125), the antagonist of JNK, 30 minutes before salvinorin A, SB203580 (10 μM, administrated topically; H/I+ SA+SB203580), the antagonist of P38, 30 minutes before salvinorin A. Pretreatment with salvinorin A preserved the dilation response of pial artery to hypotension, which is abolished by U0126. SA: Salvinorin A; H/I: Hypoxia/ischemia; Moderate: moderate hypotension (25% decrease of MAP); Severe: severe hypotension (45% decrease of MAP). N=5 each group; baseline bar represents the data from all 25 animals. All non-listed corrected P-values >0.405. All corrected 95% confidence interval width <10.32.

As shown in FIG. 17, small pial artery dilated to two levels of hypotension at baseline before hypoxia/ischemia, but the dilatation response was decreased significantly after hypoxia/ischemia ($p<0.001$ compared with that before hypoxia/ischemia). Pretreatment with salvinorin A (10 μg/kg, iv.) preserved the dilation response of pial artery to hypotension. This is abolished by U0126 ($p<0.001$ compared with SA group), the antagonist of ERK. However, there were no significantly changes after treatment of SP600125 (antagonist of JNK, $p>0.05$ compared with SA group) and SB203580 (antagonist of P38, $p>0.05$ compared with SA group) which were administered 30 minutes before administration of salvinorin A. Similar observations were obtained in pial arterioles (data not shown).

Salvinorin a Preserved Pial Artery Autoregulation to Hypercapnia after Hypoxia/Ischemia.

Figure 18:
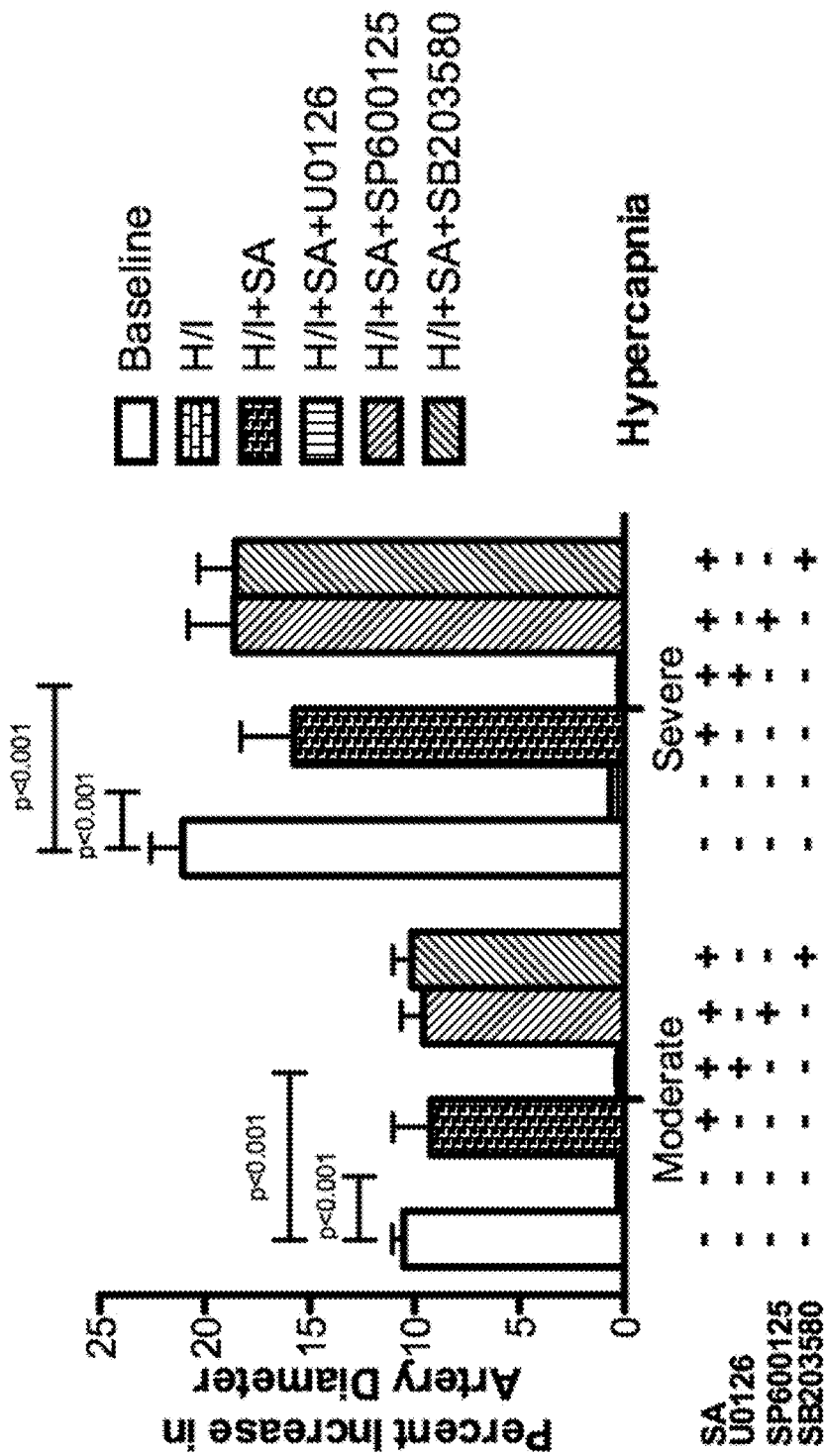
FIG. 18. Effects of hypercarbia on pial artery diameter before (baseline), after hypoxia/ischemia (H/I; PO2 of 35 mm Hg for 10 minutes followed by global cerebral ischemia for 20 minutes), after H/I pretreated with salvinorin A (10 μg/kg i.v.; H/I+SA) 30 minutes before H/I, and after H/I pretreated with U0126 (1 mg/kg, i.v.; H/I+SA+U0126), the antagonist of ERK, 30 minutes before salvinorin A, SP600125 (1 μM, administered topically; H/I+SA+ SP600125), the antagonist of JNK, 30 minutes before salvinorin A, SB203580 (10 μM, administrated topically; H/I+ SA+SB203580), the antagonist of P38, 30 minutes before salvinorin A. Pretreatment with salvinorin A preserved the dilation response of pial artery to hypercarbia, which is abolished by U0126. SA: Salvinorin A; H/I: Hypoxia/ischemia; Moderate: moderate hypercapnia with PaCO2 of 50 to 60 mmHg; Severe: severe hypercapnia with PaCO2 of 70 to 80 mmHg N=5 each group; baseline bar represents the data from all 25 animals. All non-listed corrected P-values >0.108. All corrected 95% confidence interval width <10.43.

Similar to the response to hypotension, small pial artery dilated to two levels of hypercapnia at baseline before hypoxia/ischemia (FIG. 18). The dilatation response was blunted after hypoxia/ischemia. Pretreatment with salvinorin A (10 μg/kg, iv.) preserved the dilation response of pial artery to hypercapnia. This is abolished by U0126, the antagonist of ERK. No significant change in the preservative effects was observed from SP600125 and SB203580 administered 30 minutes before administration of salvinorin A ($P>0.05$). Similar observations were obtained in pial arterioles (data not shown).

Pial Artery Response to Isoproterenol Unchanged in all Sets of Experiments

Figure 19:
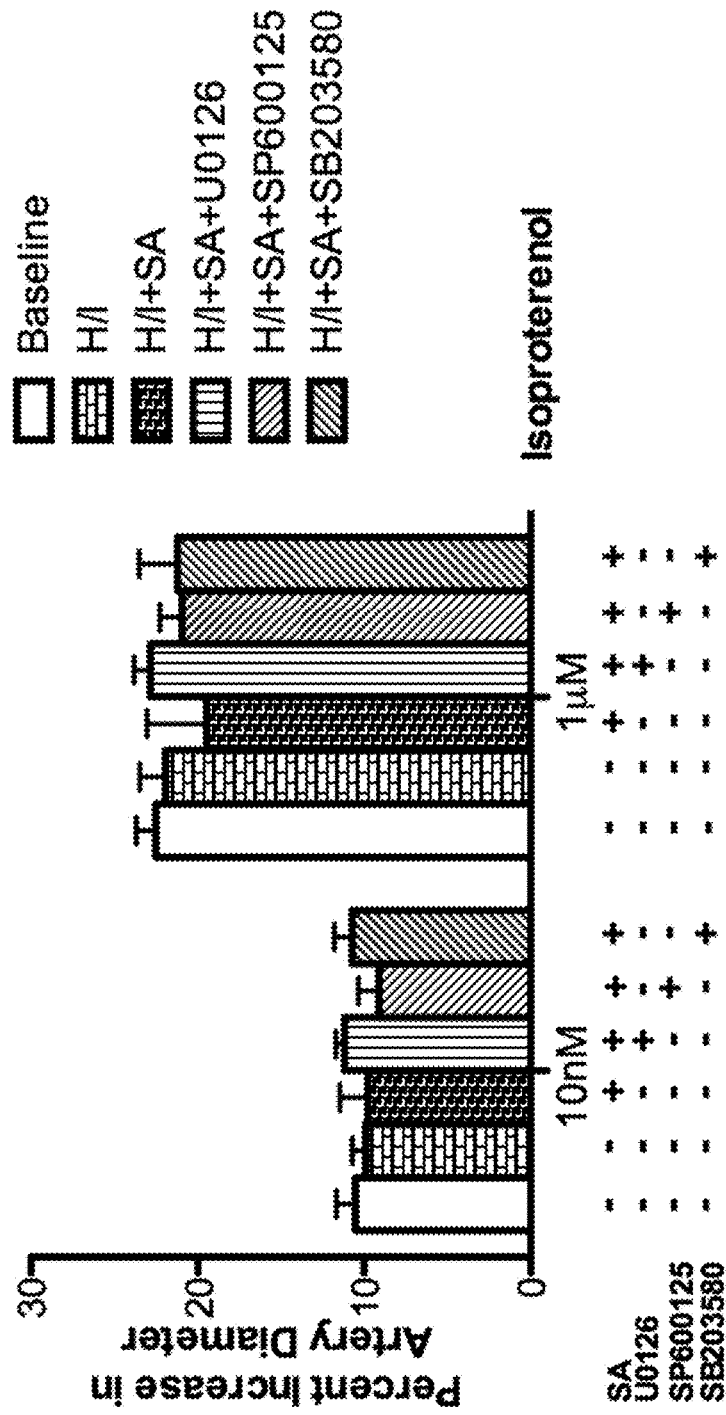
FIG. 19. Effects of isoproterenol (10 nM, 1 μM) on pial artery diameter before (baseline) and after hypoxia/ischemia did not change significantly in the presence and absence of various interventions. SA: Salvinorin A; H/I: Hypoxia/ischemia. N=5 each group; baseline bar represents the data from all 25 animals. All non-listed corrected P-values=1. All corrected 95% confidence interval width <10.13.

As a positive control and shown in FIG. 19, pial artery response to isoproterenol was unchanged in all groups before and after hypoxia/ischemia in the presence or absence of the above interventions.

ERK Involved in the Preservation Effects of Salvinorin A

Figure 20:
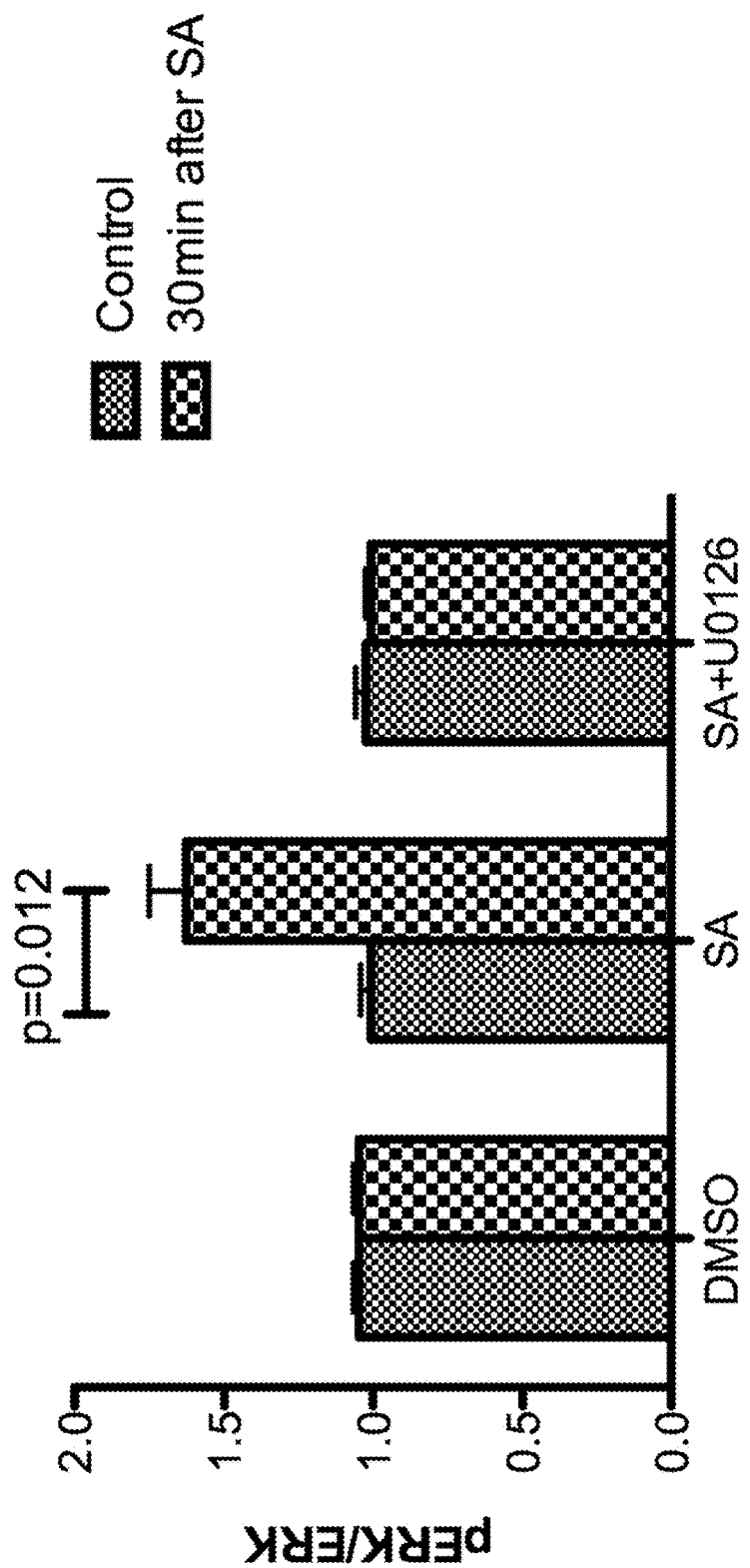
FIG. 20. The ratio of pERK/ERK before administration of salvinorin A and 30 minutes after pretreatment of salvinorin A or U0126 plus salvinorin A. The ratio of pERK/ERK in CSF increased significantly 30 minutes in the salvinorin A pretreatment group; and such increase was abolished by the ERK antagonist (U0126) pretreatment SA: Salvinorin A. H/I: Hypoxia/ischemia. All non-listed corrected P-values=1. All corrected 95% confidence interval width <0.33.

The ratio of pERK/ERK in CSF increased significantly 30 minutes after salvinorin A pretreatment (FIG. 20). However, if U0126, an antagonist of ERK, was administrated 30 minutes before salvinorin administration, the ratio of pERK/ERK was unchanged 30 minutes after salvinorin A pretreatment (FIG. 20).

Discussion

There are two principal new findings in this Example. First, pretreatment of salvinorin A preserved cerebrovascular autoregulatory ability after hypoxia/ischemia. Second, ERK/MAPK is involved in the ability of salvinorin A to preserve autoregulation. This Example also confirmed earlier findings that global hypoxia/ischemia in the newborn piglets blunts the autoregulatory ability of the cerebral vascular response to hypotension and hypercapnia.

Although the pathophysiological responses to cerebral hypoxia/ischemia in infants is not fully elucidated, cerebrovascular dysfunction plays a very important role in neurological insult after hypoxia/ischemia. There is no optimal pharmacological intervention that could be used to prevent or preserve cerebral vascular autoregulatory responses to hypotension and hypercapnia secondary to brain injury. The only medication approved by the Food and Drug Administration for stroke is recombinant tissue plasminogen activator (tPA). However, despite its salutary role in reopening the clotted blood vessel, tPA increases stroke infarct volume in mice and it potentiates the impairment of autoregulation induced by hypoxia/ischemia. L-NNA, an inhibitor of nitric oxide synthesis, was proven to be able to restore cerebral vascular auto regulation administrated after ischemia, however, its safety profile is unclear for clinical usage.

In this Example we demonstrate that salvinorin A pretreatment preserved the autoregulatory responses to hypotension and hypercapnia after hypoxia/ischemia in a piglet model, which opens its clinical applications to attenuate cerebral hypoxia/ischemia, especially for anticipated brain ischemia during DHCA in infant. More studies are needed to provide direct evidence to demonstrate whether it could attenuate neuronal cell injury from hypoxia/ischemia.

Unlike other KOR receptors that have no proven clinical values, salvinorin A is extracted from an abundant natural plant, *Salvia divinorum*. Very similar to the history of opium, *Salvia divinorum* as a naturally abundant plant has been used by human beings for various purposes, for centuries. It has been proposed that salvinorin A, the active component of *Salvia Divinorum*, could be a potential new kappa agonist to be used in clinical practice.

Salvinorin A is a potent cerebral vascular dilator in normal and constricted conditions as we have demonstrated. However, this dilatation effect is short lived unless with continued administration; thus, the preservation of autoregulation is unlike induced from the dilatation effects since salvinorin was administrated 30 min prior hypoxia/ischemia. MAPK has been proven to be important in signal transduction from the cell surface to the nucleus. Elevation of ERK/MAPK before ischemia is related to neuronal survival after ischemia (15). Activation of ERK/MAPK in the hippocampal CA1 region after sublethal ischemia correlates with neuro-protection induced by preconditioning. Exercise preconditioning reduces neuronal apoptosis in stroke by up-regulating ERK/MAPK. In this Example, pERK/ERK in CSF increased significantly 30 minutes after administration of salvinorin A, indicating the activation of ERK and also suggesting that salvinorin A might be vascularly or neuronally protective when administered prior to brain ischemia. However, other studies have observed that elevation of ERK/MAPK in the immediate post injury reperfusion period is associated with impairment of responses to cerebrovasodilators as well as histopathology after hypoxia/ischemia in the piglet (32). The reason for the observed duality of ERK/MAPK function is uncertain but may relate to the cellular site of origin, signal coupling, or temporal pattern of release.

Newborn piglets used in this Example offer the unique advantage of a gyrencephalic brain containing substantial white matter, which is more sensitive to ischemic damage than rodent brain, and more similar to humans. In conclusion, salvinorin A pretreatment preserved cerebrovascular autoregulation to hypotension and hypercapnia after brain hypoxia/ischemia via ERK/MAPK in a piglet model.

Example 4

Salvinorin as an Adjunctive Medication for Difficult Airway Management

Figure 11:
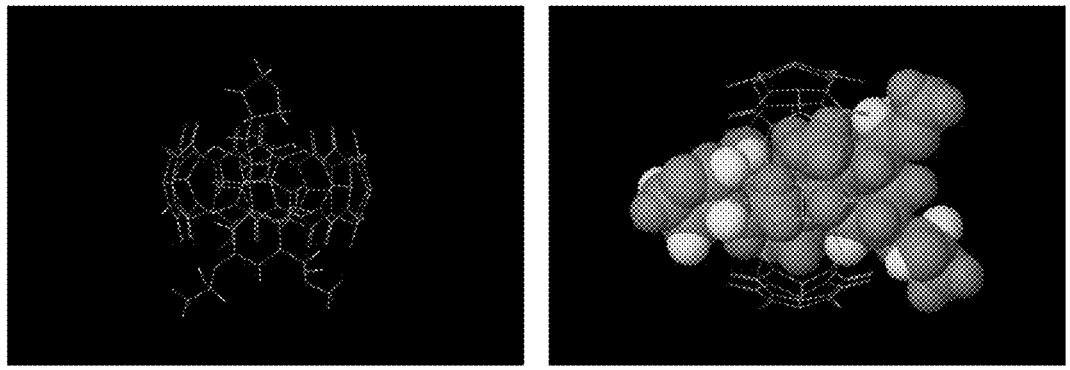
FIG. 11 is an image of salvinorin-cucurbituril complex.
Figure 12:
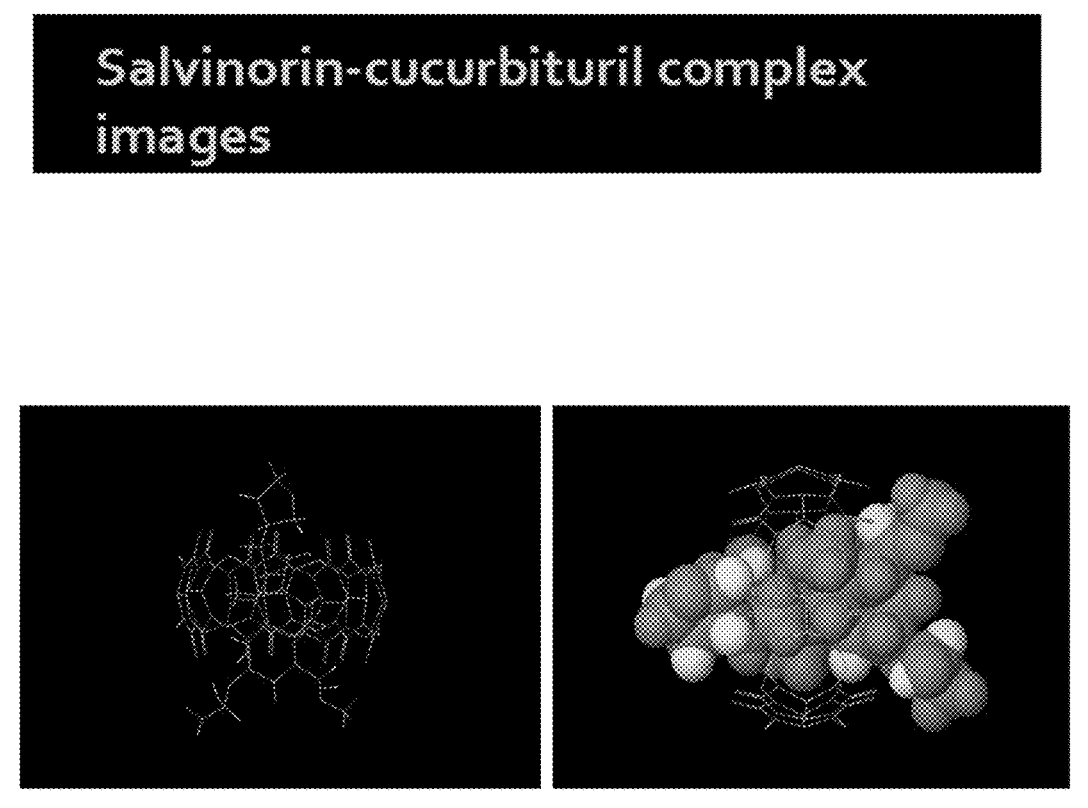

We often have to manage a patient's airway in the awake (unanesthetized) state when difficult airway is an issue, but partial sedation facilitates patient comfort and conduct of the procedure. An ideal sedative should meet the following criteria: (1) be sedative; (2) have a rapid onset; (3) be short acting; (4) inhibit coughing; (5) have minimal respiratory inhibition; (6) have minimal hemodynamic effects, and (7) be easy to be deliver intravenously. Salvinorin A meets these criteria, at least based on data available in the literature. It is a kappa opioid receptor agonist which has sedative and dissociative effects, inhibits cough and has minimal respiratory depressive effects, at least as compared to conventional mu receptor agonists (morphine). It has fast onset and offset with minimal hemodynamic changes. Thus, salvinorin can be useful during awake intubation. However, salvinorin is poorly soluble in water. One option is to use its salt form to increase water solubility, and the other is to use lipid emulsion. Both techniques are readily available and have been successfully used for other anesthetic drugs in the perioperative settings. Cucurbituril (FIG. 11) could be used as a carrier. As shown in FIGS. 12-13, a complex of salvinorin and cucurbituril can be used.

Another concern related to this medication is its dysphoric effects, which can be addressed with short-acting benzodiazepines like midazolam.

Example 5

Salvinorin a Decreases Mortality and Improves Neurological Outcome in a Neonatal Mouse Hypoxia Model Neonatal hypoxic-ischemic (HI) injury can induce high mortality and lifelong catastrophic neurologic and neurodevelopmental deficits that include epilepsy, learning disabilities, and behavioral disorders. Unfortunately, no effective drug is available for managing HI-related neurological deficits. Therapeutic hypothermia along with supportive treatment is considered the only effective approach. However, well-controlled hypothermia can only be applied to highly selected patient populations in well-established facilities and it can only produce an outcome improvement of only about 30% in asphyxiated infants. It requires extensive training and multidisciplinary collaborations. In under-resourced facilities, therapeutic hypothermia can be dangerous, leading to an increased incidence of mortality, multiple organ failure, sudden cardiac arrest, pulmonary hypertension, and bleeding. Thus, there is a significant medical need to develop a novel medication and/or easily manageable therapeutic strategy to reduce neuronal injury from cerebral HI in the perinatal period.

Salvinorin A (SA) is a non-opioid, highly selective and potent kappa opioid receptor (KOR) agonist extracted from *Salvia divinorum*, a plant that has been consumed by human for several centuries. Using a piglet model, it has previously been demonstrated that SA administration before or after brain HI protects the brain from HI (Su D, et al., Anesth Analg. 2012; 114:200-204; Su D, et al., Anesthesiology. 2011; 114:374-379; and Wang Z, et al., PLoS One. 2012; 7:e41724; each of which is hereby incorporated by reference in its entirety), indicating that SA could be a potential medication for brain protection for neonates. Unlike other opioid KOR agonists, SA does not produce dysphasia and its intrinsic characteristics make it an ideal therapeutic candidate for various neurological conditions. These characteristics include: rapid onset, easy passage to the central nervous system, antinociceptive and sedative effects, no negative pathological changes in organs following prolonged or high dose exposure, and no respiratory depressive effect. Although the compound has been reported to have hallucinogenic activity, such effects are short-lived and do not produce blood pressure and heart rate changes or cognition impairment. In a recent human study, no persisting adverse effects related to SA were observed.

In this Example, we hypothesized that SA administration could improve outcomes in a neonatal mouse hypoxia model. The mouse model was chosen due to the availability of a well-established model, neurobehavioral testing strategies and the capability to investigate both short-term and long-term neurological outcomes.

Subjects and Methods

Salvinorin A (purity ≥98%) was obtained from Apple Pharms (Asheville N.C., USA). All other chemicals (reagent grade) were obtained from Sigma-Aldrich (MO, St. Louis, Mo., USA).

Experimental Protocol

The protocol was approved by the Institutional Animal Care and Use Committee (IACUC) of the University of Pennsylvania and carried out in accordance with National Institutes of Health guidelines for the use of animals. C57BL/6J mice were purchased from The Jackson Laboratory (Bar Harbor, Me.) and inbreed pups were used for subsequent experiments. Pups were housed under a 12-hour light/dark cycle after birth with free access to food and water throughout the study. Pups from different litters were divided into 3 groups randomly. Pups in the control group (n=11) received i.p. injection of 17% dimethyl sulfoxide (DMSO) without hypoxia insult; the hypoxia group (n=46) received i.p. injection of 17% DMSO and hypoxia insult; SA group (n=26) received i.p. injection of 0.5 mg/kg SA in 17% DMSO and hypoxia insult. Pups of low weight (<1.2 g) were excluded from the study.

Hypoxic Insult

The hypoxic insult was induced on postnatal day 1. After i.p. injections, pups were put into a glass chamber in a water bath where the temperature was maintained at 37° C. The chamber was tightly closed and filled with 8% oxygen with balanced nitrogen. Following 120 minutes of hypoxic gas exposure, the chamber was opened and the pups were exposed to the air. Chest compressions and limb stretches were performed for up to 20 minutes to regain spontaneous breathing. The pups that successfully regained spontaneous breathing were then returned to their mothers after recovery for 30 minutes.

Mortality Rate Determination

The neonate mouse will be considered as non-survival if no spontaneous breathing can be restored for 20 min resuscitation immediately after anoxic insult. The mortality rate will be calculated as: survival rate=(number of mice in a group-number of non-survival)/number of mice in a group.

Short-Term Developmental Motor Behavior Observation

From postnatal day 2 to postnatal day 21, the pups were weighed and motor behavior observation was performed every day. Pups were observed individually in a plastic testing box. Each of the following behaviors was recorded for 3 minutes: crawling, walking, running, head point and sniffing, sitting, rearing and eye opening. After the observation, placing reflex, cliff aversion, negative geotaxis, righting response and forelimb grasping testing were performed. The first appearance of the behavior or reflex continued for two consecutive days was recorded.

Long-Term Neurobehavioral Effects of SA

The open field test was performed to gauge locomotor activity on postnatal day 21 at which the mouse was considered juvenile. Mice were individually placed in a 41 cm (L)×41 cm (W)×30 cm (H) plastic box. The "central area" was defined as a 20.5 cm×20.5 cm square in the center of the box. The rest of the area was defined as the "peripheral area" (see FIG. 25A). The time each mouse spent on exploring the central and periphery parts and the number of rearing behaviors in each respective area were recorded for the first 5 minutes and 30 minutes.

At the age of 10-11 weeks, all mice were tested in several behavioral tasks in the order of: zero mazes, barnes maze and fear conditioning. These tasks were performed to examine the basal anxiety level, spontaneous locomotor activity, motor learning, spatial learning and associative memory of the mice. The mice were given 5 days for rest between each behavioral test.

Zero Maze (Anxiety-Like Behavior):

"Time in open" measures mice anxiety due to their tendency to avoid open spaces. The anxiety was measured by recording the time spent in the open vs. enclosed space. Increased anxiety correlates to decreased time in the open. Open/Closed transitions measure overall activity. Increased transitions equate to greater activity.

Barnes Maze (Spatial Learning):

Measures the ability to learn with visual cues. Time to Target measures the time taken to find the target hole in an arena with 19 other holes and several visual cues. The Barnes Maze is easier to set-up and probably less stressful and a valid alternative to the Water Maze to study spatial memory. One of the advantages of the Barnes maze task was that it was not influenced by stress as much as other similar tasks and no strong aversive stimuli or deprivation were used.

Fear Conditioning (Memory):

Training trial freezing, short term contextual freezing, long term contextual freezing and cued trial freezing were recorded to examine and assess the memory deficits after hypoxia injury.

Statistical Analyses

Mortality of pups in different groups was compared using a 2×2 contingency table. P-value was calculated with the Fisher exact test. For motor behavior observation, the first days of appearance for each parameter were compared with one-way ANOVA followed by Turkey's test. Statistical analyses were performed with Graph-Pad Prism (Version 5.0). Data were showed as mean±SEM. A value of $p<0.05$ was considered to be statistically significant.

Results

Figure 21:
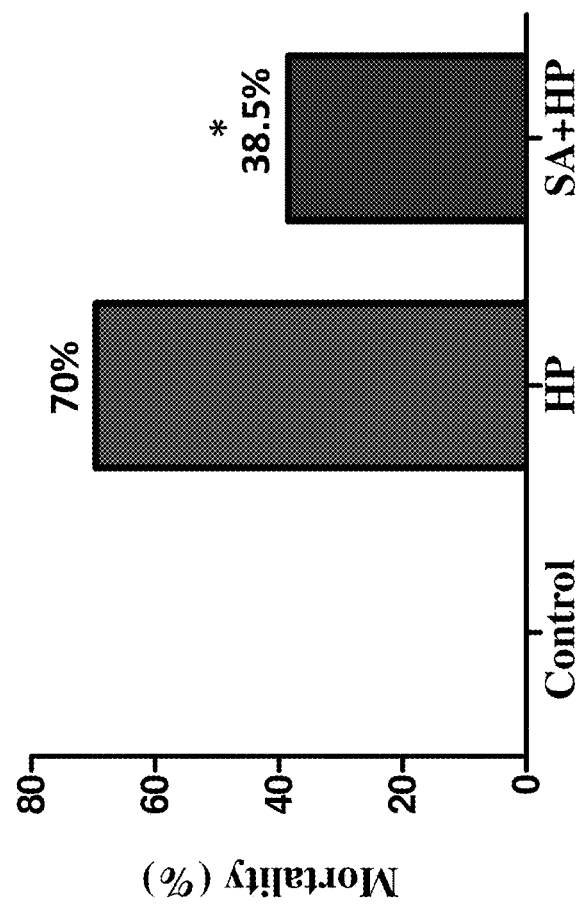
FIG. 21 shows the mortality of different groups in Example 5. The mortality of HP and SA group is 70% and 38.5%, respectively. There was no death in the control group. The difference between SA and HP groups indicated that SA statistically decreased the mortality significantly (*p=0.014, SA+HP vs. HP. SA: Salvinorin A; HP: Hypoxia).

SA Significantly Decreased Mortality 14 out of 46 pups in the hypoxia group and 16 out of 26 pups in the SA group survived after HI injury. SA significantly decreased the mortality rate from 70% to 38.5% (p=0.014) (FIG. 21).

SA Increased Body Weight on Postnatal Day 2 and Day 3

Figure 22:
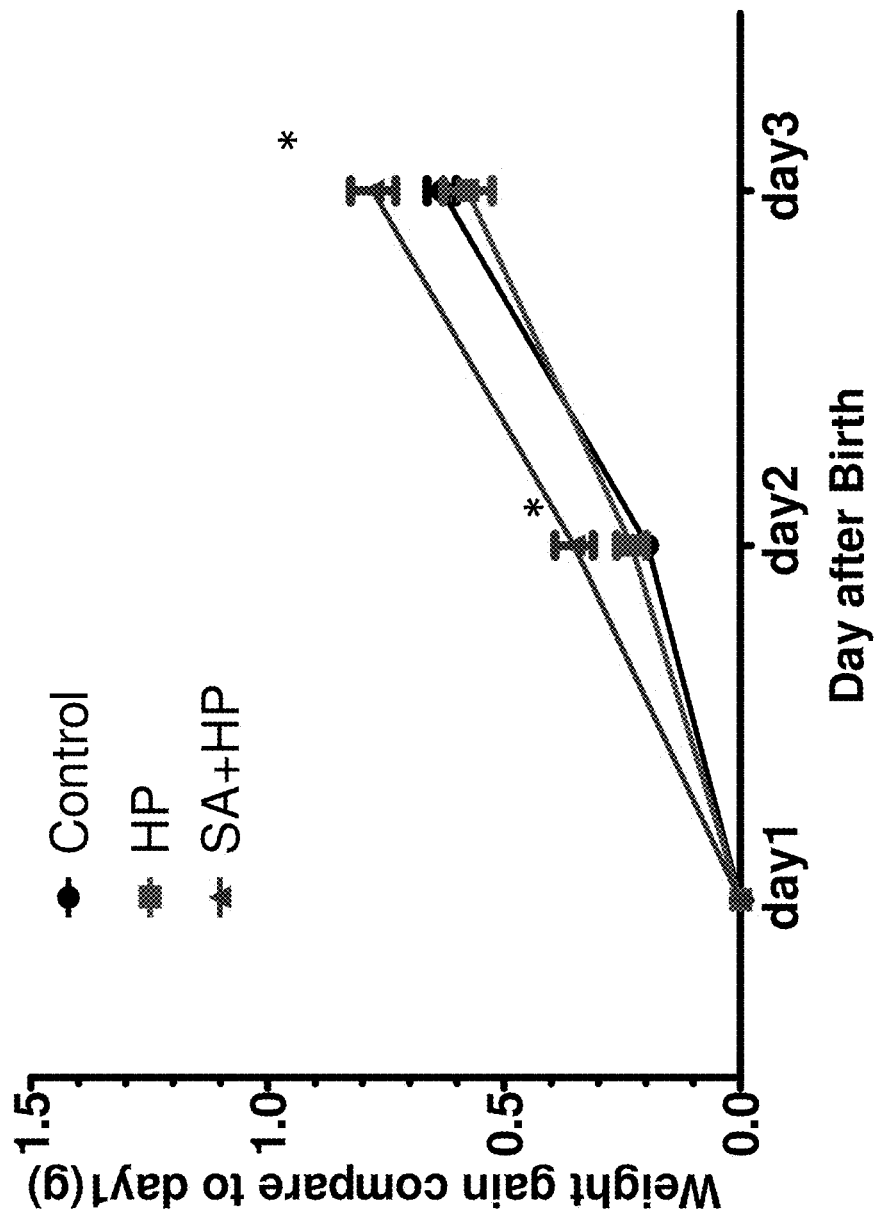
FIG. 22 shows that SA elevated the body weight gaining on postnatal day 2 and day 3 in Example 5. Body weight of pups in control, hypoxia, and SA treated groups on P1, P2, P3, P7, P14, and P21 were recorded in our study. SA treatment elevated the body weight gaining compared to day 1 on P2 (p=0.0318) and P3 (p=0.0221). However, on P3, P7, P14 and P21, no significant difference was observed between different groups (data not shown) (*p<0.05 SA+HP vs. HP. P: postnatal; SA: Salvinorin A; HP: Hypoxia).

SA administration increased body weight compared with those in the hypoxia group on postnatal day 2 (P2) (p=0.0318) and day 3 (P3) (p=0.0221). However, no significant difference was observed among groups on P7, P14 and P21 (FIG. 22).

SA Improved Developmental Outcomes

Figure 23:
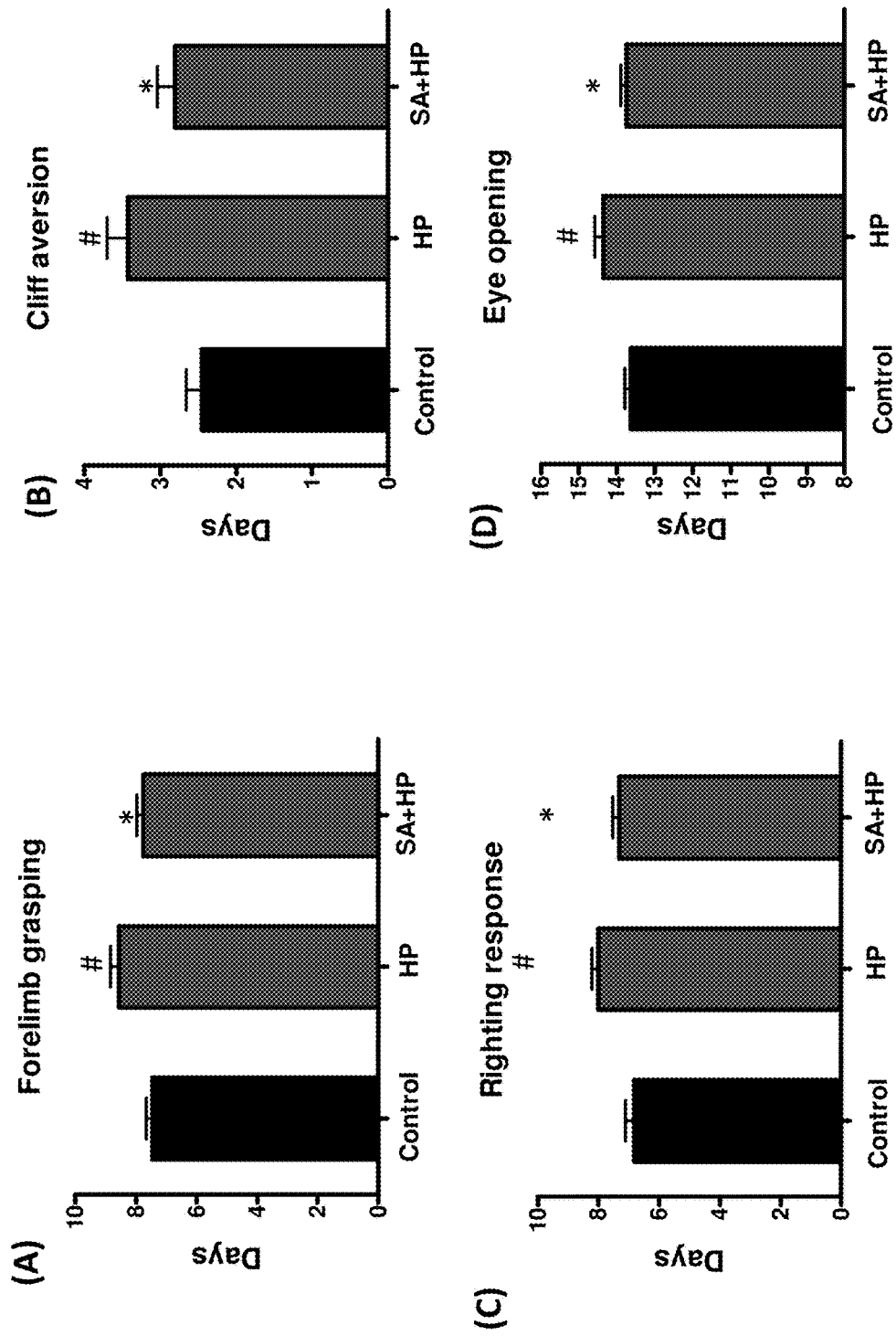
FIG. 23 shows that SA improved some developmental neurological outcomes in Example 5. Hypoxia induced significant delay in forelimb grasping (A), cliff aversion (B), righting response (C), and eye opening (D). SA rescued such hypoxia induced neurological outcomes significantly (#p<0.05 HP vs. Control; *p<0.05 SA+HP vs. HP. SA: Salvinorin A; HP: Hypoxia).

Pups in the hypoxia group showed delayed appearance of forelimb grasping, cliff aversion, righting response and eye opening. SA administration prevented these delays (FIG. 23).

Figure 24:
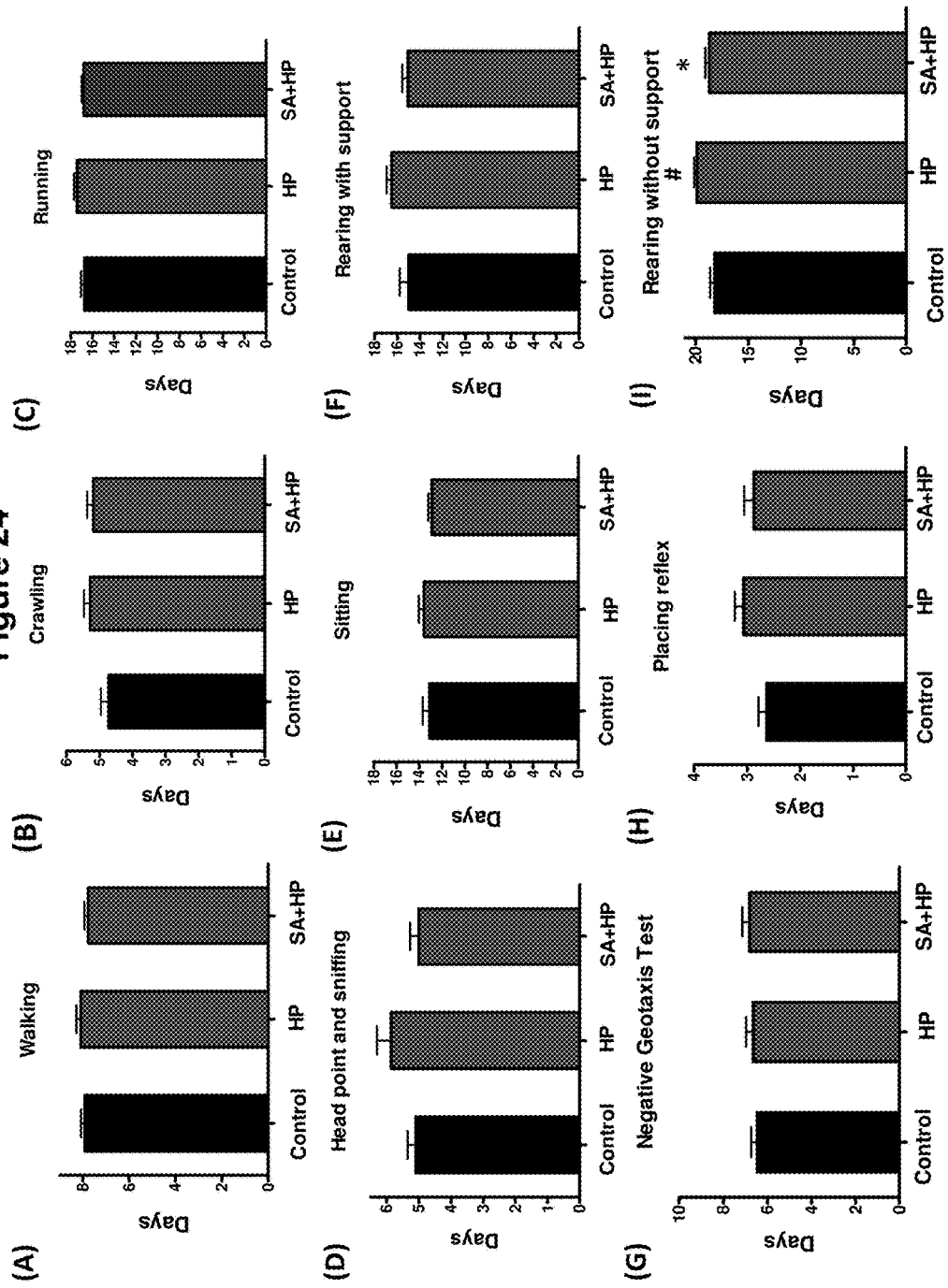
FIG. 24. SA showed no statistical improvement on some of the development parameters in Example 5. There are no statistical significance on some of the development parameters such as walking (A), crawling (B), running (C), head point and sniffing (D), sitting (E), rearing with support (F), negative geotaxis test (G) and placing reflex (H), though hypoxic pups also showed delayed appearance compared to control and SA groups. Hypoxia pups showed delayed appearance of rearing without support at day 19.86±0.29 compared to day 18.18±0.4435 in control group. Hypoxic pups treated with SA presented better performance than hypoxic pups at day 18.69±0.3843(I), which is similar with control group (#p<0.05 HP vs. Control; *p<0.05 SA+HP vs. HP. SA: Salvinorin A; HP: Hypoxia).

Hypoxia pups showed delayed appearance of rearing without support (FIG. 24I) at 19.86±0.29 day compared to 18.18±0.44 day in control group (p=0.0034). Hypoxia pups with SA administration presented significant improved performance than hypoxic pups at 18.69±0.38 (p=0.0252), which is similar to the control group. However, there was no statistical significance with other developmental parameters such as crawling (FIG. 24A), walking (FIG. 24B), running (FIG. 24C), head point and sniffing (FIG. 24D), sitting (FIG.

24E), rearing with support (FIG. 24F) negative geotaxis test (FIG. 24G) and placing reflex (FIG. 24H), though hypoxic pups also showed delayed appearance compared to both the control and SA groups.

Long-Term Neurobehavioral Outcome

Figure 25:
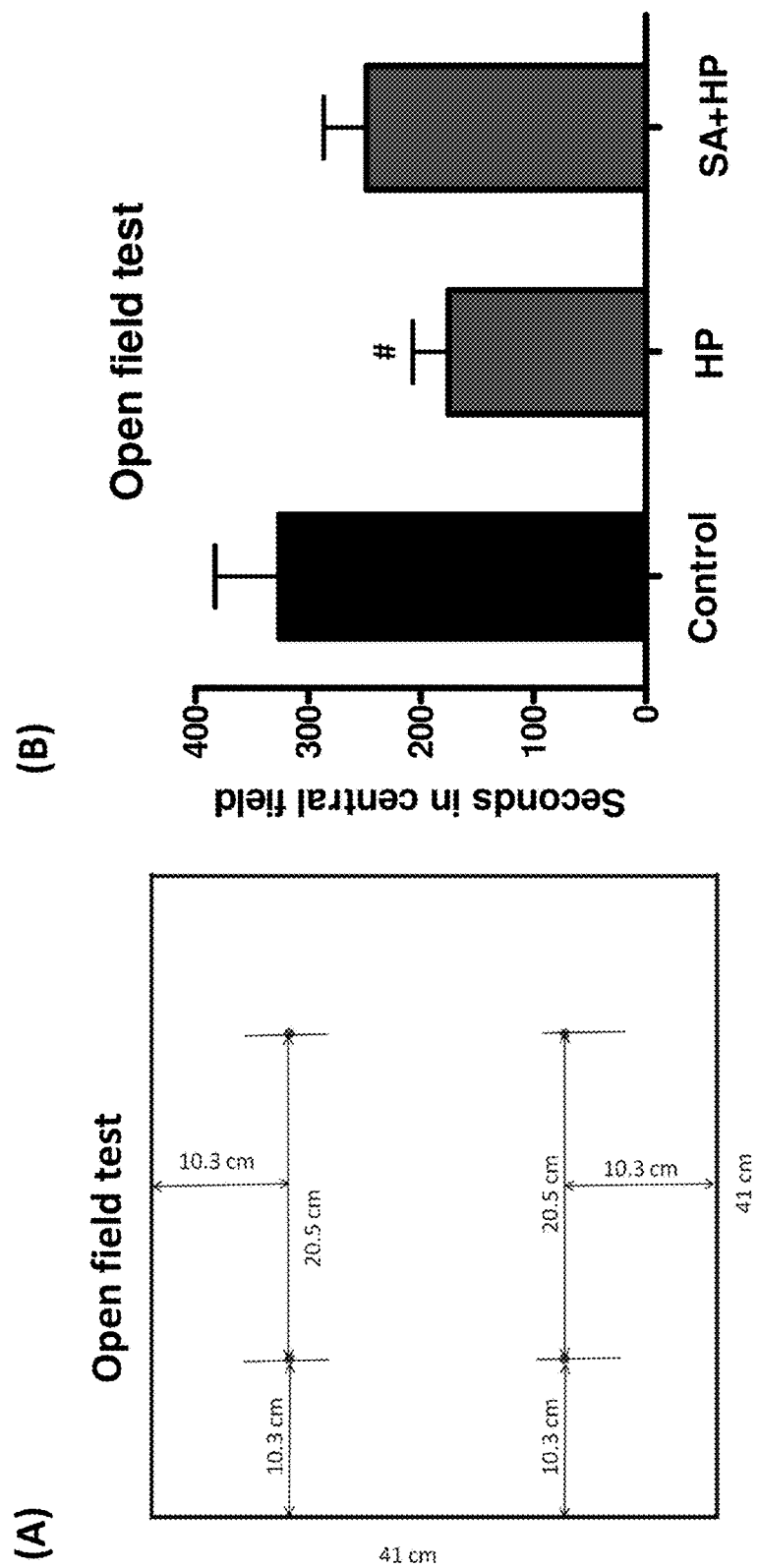
FIG. 25. SA did not improve the outcome of open field test significantly in Example 5. (A) The left figure shows the sketch of the open field test. Mice were individually placed in a 41 cm (L)×41 cm (W)×30 cm (H) plastic box. "Central part of the area" was defined as a 20.5 cm×20.5 cm square in the center of the box. The rest of the area was defined as "peripheral part of the area". The time each mouse spent on exploring the central part and periphery part of the area and the number of rearing behavior were recorded respectively in the first 5 minutes and 30 minutes. (B) The seconds in the central field was recorded in open field test at P21 which showed that HP significantly decreased the seconds compared to the control and SA administration increased seconds in the central filed after hypoxia, but the difference was not statistically significant (#p<0.05 HP vs. Control. P: postnatal; SA: Salvinorin A; HP: Hypoxia).
Figure 26:
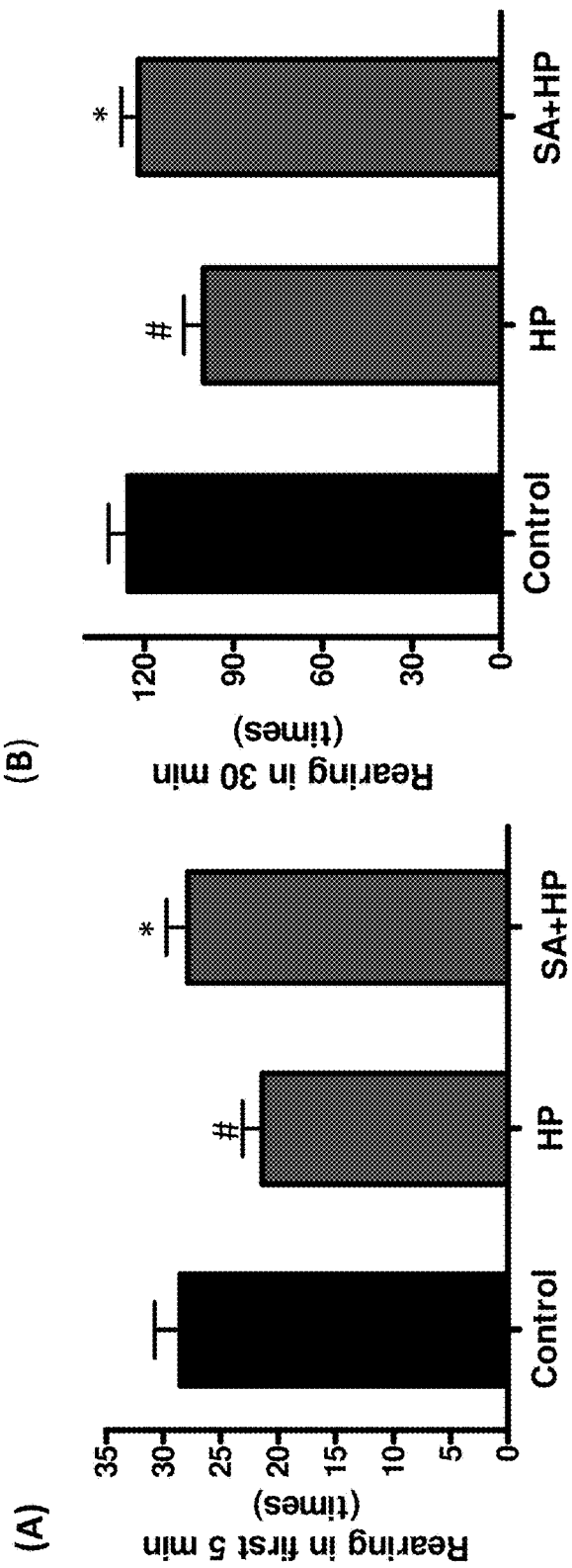
FIG. 26 shows that SA improved rearing activity at P21 significantly in Example 5. Rearing test at P21 in the first 5 min and 30 min was impaired by hypoxia and such impairment was not observed with SA administration which was similar to the control group, indicating that SA could improve some of the hypoxia induced long term neurological deficit (#p<0.05 HP vs. Control; *p<0.05 SA+HP vs. HP. P: postnatal; SA: Salvinorin A; HP: Hypoxia).

Although SA mice spent more time in the central area during open field testing at P21, this difference was not statistically significant (FIG. 25). Meanwhile, the rearing test at P21 in the first 5 minutes and 30 minutes was impaired after hypoxia. This impairment was not observed with SA administration, similar to that in the control group, suggesting that SA could improve hypoxia induced the neurological outcomes (p=0.0167 and p=0.0203, respectively) (FIG. 26).

Figure 27:
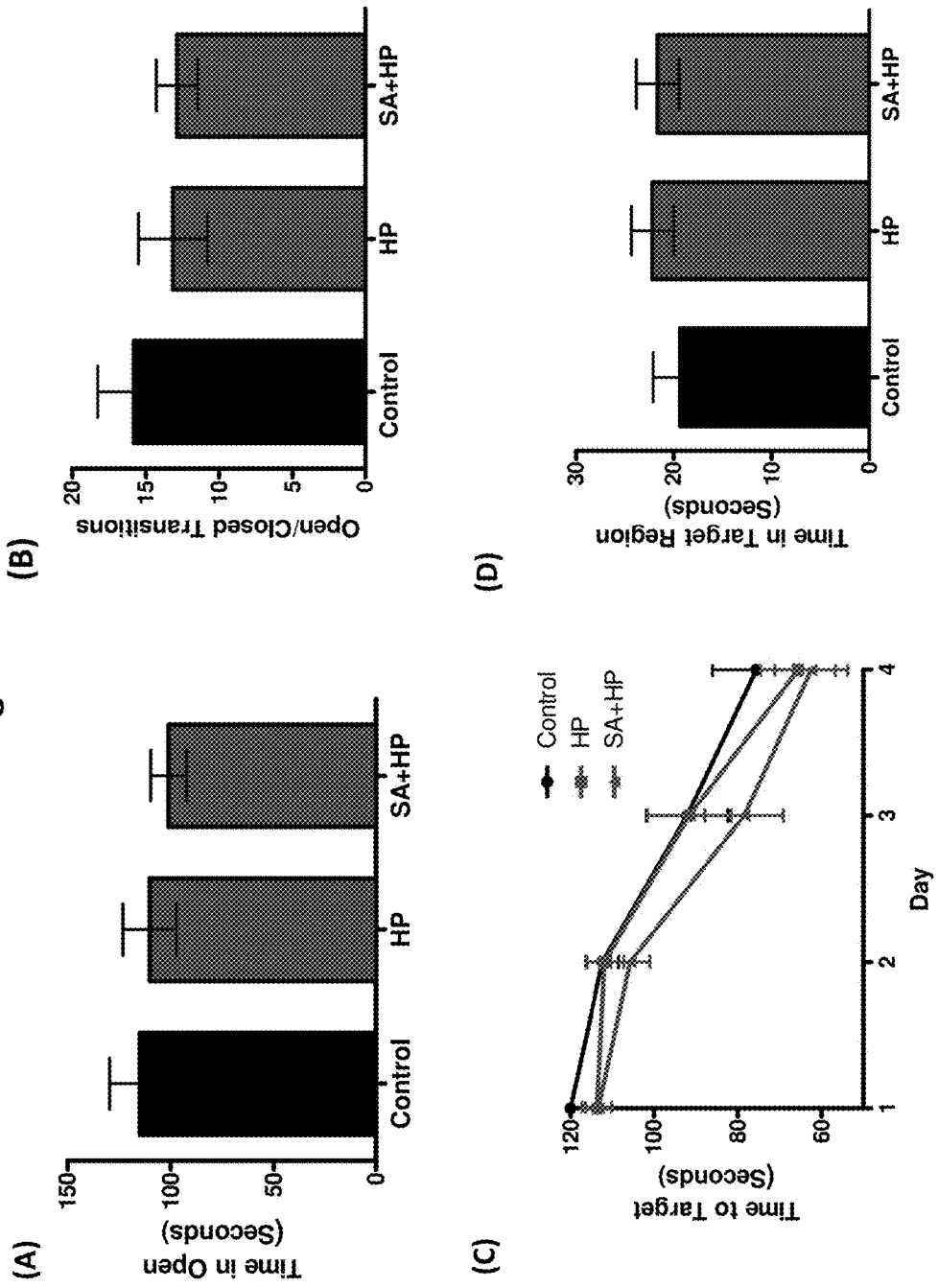
FIG. 27 shows that SA did not improve the long term anxiety level and spatial memory in Example 5. As for the elevated zero maze to detect the anxiety level and locomotor activity, there were no significant differences in the percentage of time spent in the open arm (A) and open/closed transitions (B) of the maze between SA administration and hypoxia alone groups. The Barnes maze task was used to assess spatial reference memory. In our study, there was no significant difference between the groups of the time to target (C) and time in target region (D). There was also no difference between the control and HP groups (SA: Salvinorin A; HP: Hypoxia).
Figure 28:
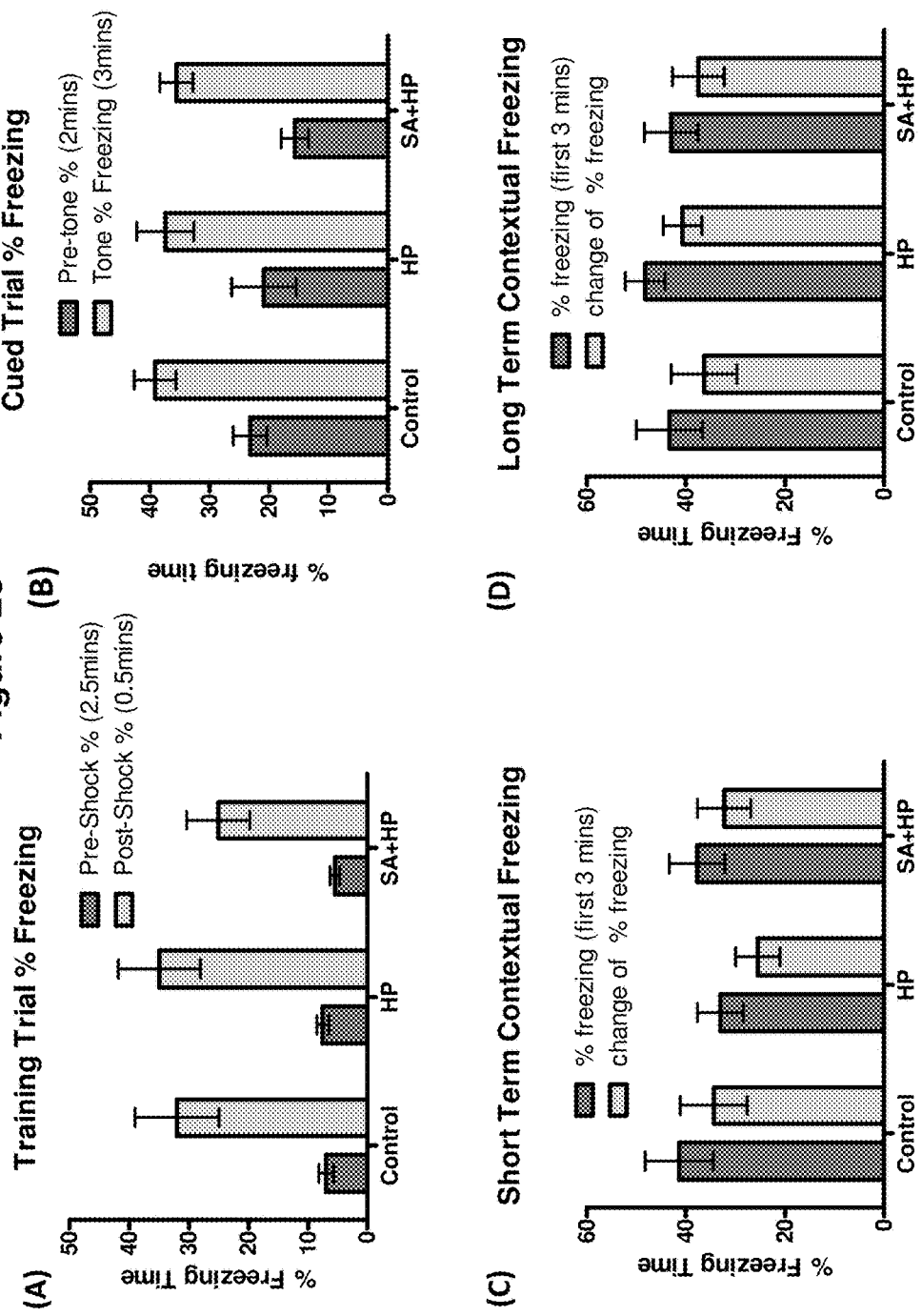
FIG. 28 shows that SA did not change the long term memory deficit in Example 5. All groups learned at similar rates and there was no significant difference in the long-term behavior of fear conditioning test. Control group showed no impairment compared to HP group in the training trial (A), cued trial (B), short term (C) and long term (D) contextual freezing behavior (p>0.05). Pretreatment with SA did not change the fear memory compared with HP and Control mice (p>0.05. SA: Salvinorin A; HP: Hypoxia).

The effects of SA on the anxiolytic properties after HI were tested using an elevated zero maze. There were no significant differences in the percentage of time spent in the open arm and open/closed transitions of the maze between SA and hypoxia groups (FIG. 27A, B). The Barnes maze task was used to assess spatial memory deficits. However, there was no significant difference among groups (FIGS. 27C and D). Also, tests of fear conditioning showed that all groups learned at similar rates and no significant differences were observed among groups either (FIG. 28).

Discussion

In this Example, we found that SA administration before hypoxia reduces the mortality rate and improves several neurological development parameters. However, no significant differences for neurological outcomes beyond 21 days were observed among groups. The findings in this Example are consistent with the study in piglets, which revealed that SA could reduce HI induced injury.

SA and Mortality after Hypoxia Insult

The reduction of the mortality rate is one of the most striking findings in this study. While it could be attributed to the neurological protective effects of SA, it is possible that SA could offer protective effects in other vital organs like heart during hypoxia insults. It has been demonstrated that KOR agonist could protect heart from ischemia. Further well defined and targeted studies using SA as a potential therapeutics are needed for future studies. The mortality in the control group for this model was very high (70%), which is higher than that was reported using the modified Rice-Vannucci model. A possible explanation may be related to the use of the pups at postnatal day 1 in our study instead of postnatal day 10 that was used in the Rice-Vannucci model. Due to the high mortality rate, we remained the design of the study relatively simple for neurological outcome observation only without dose-response studies and therapeutic time window investigation or mechanism studies.

Short-Term Developmental Outcome

Neurodevelopmental was impaired by hypoxic insult as indicated by the deficits in neurological developmental behaviors and reflexes (righting, placing, negative geotaxis and cliff aversion). SA improved some of the developmental behaviors (forelimb grasping, eye opening and rearing without support) and some of the reflexes (righting and cliff aversion). Although some significant improvements were observed, we found that SA did not provide neuroprotection on all aspects of the developmental parameters which are related to various regions of the brain. It is possible that not all the observation is sensitive enough to detect the subtle changes in behavior which may need fairly large sample size.

Long-Term Neurological Outcome

To gauge brain function and the influences on emotional behaviors of SA in the long-term at 10-11 weeks (adult age), we chose zero mazes to measure the anxiety level, barnes maze to measure spatial and visual learning, and fear conditioning to measure associative memory. Unfortunately, there was not any significant difference among groups. Most importantly, no difference of long-term neurological outcome was found between control and hypoxia group, indicating that this model may be not suitable for long-term neurological outcome studies. Although other reports have indicated that SA impairs long-term memory without affecting short-term memory, there is not any memory or learning disability observed after SA administration in this study.

Conclusion

In this Example, the administration of SA is associated with improved neurological outcomes in several aspects and reduced mortality rate after hypoxic injury, suggesting that SA could serve as a treatment strategy for neonatal hypoxia.

Example 6

Intranasal Salvinorin a Reduces Infarct Size and Improves Neurological Outcome in a Mouse Stroke Model Salvinorin A (SA) is the only known naturally occurring non-opioid KOR agonist that has been consumed by humans for centuries with a known safety profile. It has a rapid onset (within minutes) when delivered either via mucosa or inhalation. SA intranasal can be performed quickly in acute settings where intravenous (IV) access is unavailable (which is very common for out-of-hospital cardiac arrest events). A major barrier for effective therapies for ischemic stroke is how quickly the medication can be delivered to the patient. While IV administration ensures quick onset, IV access is generally not available in an out-of-hospital situation. Oral administration generally requires more than 30 min for pharmacological effects to be achieved. Thus, rapid therapeutic delivery intranasal would make SA an extremely practical and favorable medication for treating brain hypoxia/ischemic events.

Figure 29:
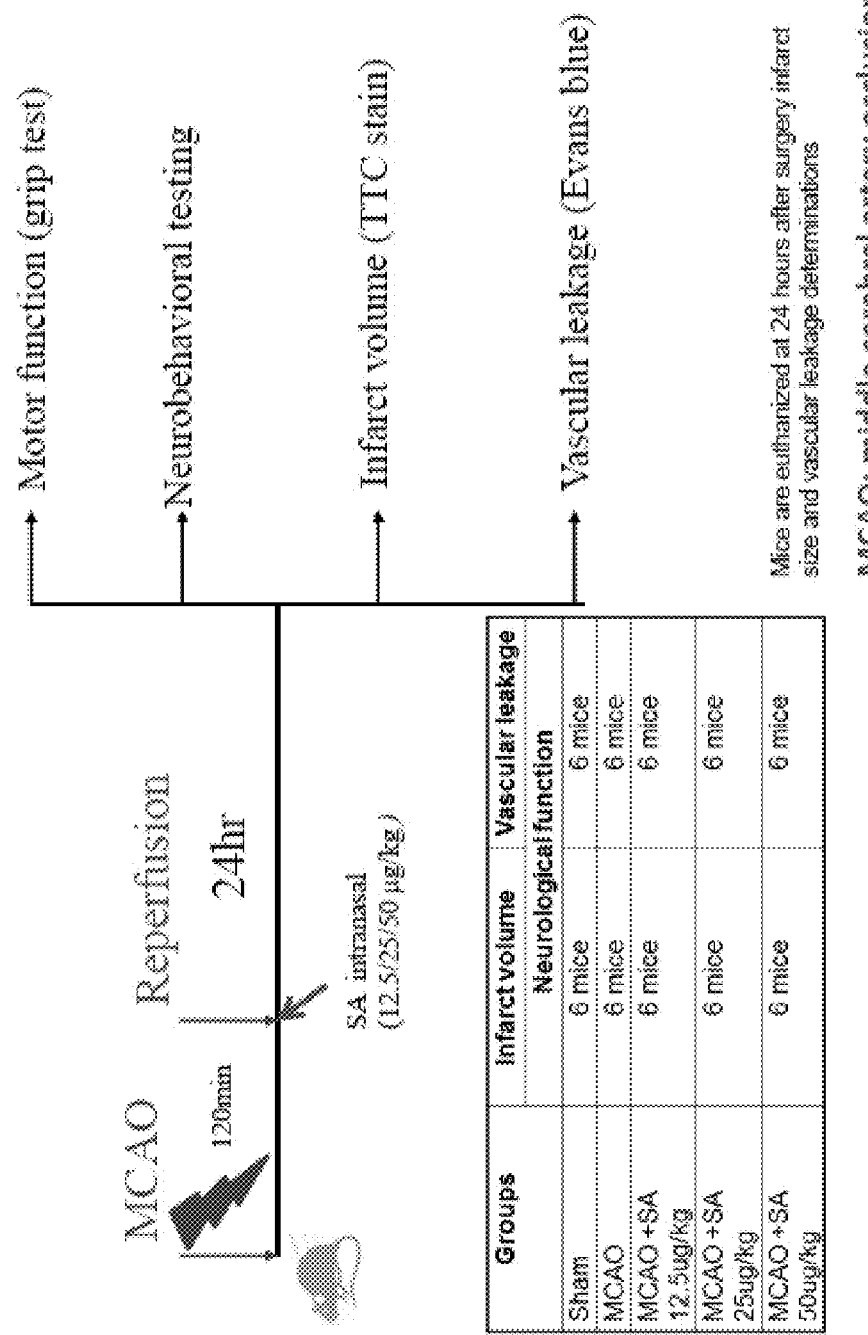
FIG. 29 depicts the protocol used in the mouse study of Example 6.
Figure 30:
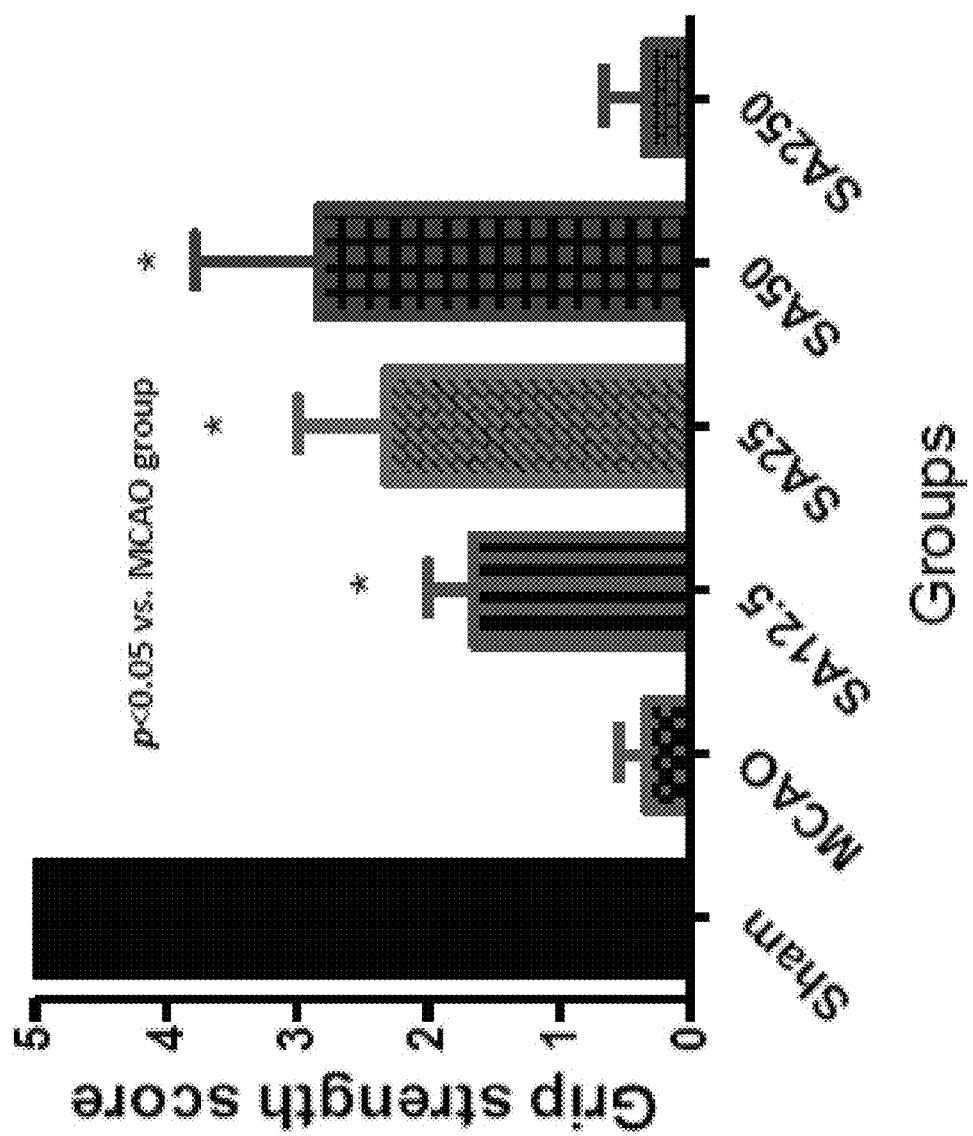
FIG. 30 shows that intranasal salvinorin A administration demonstrated dose-dependent improvements in motor function as measured by a grip strength score. However, such protective effects diminish beyond the dose of 250 µg/kg.
Figure 31:
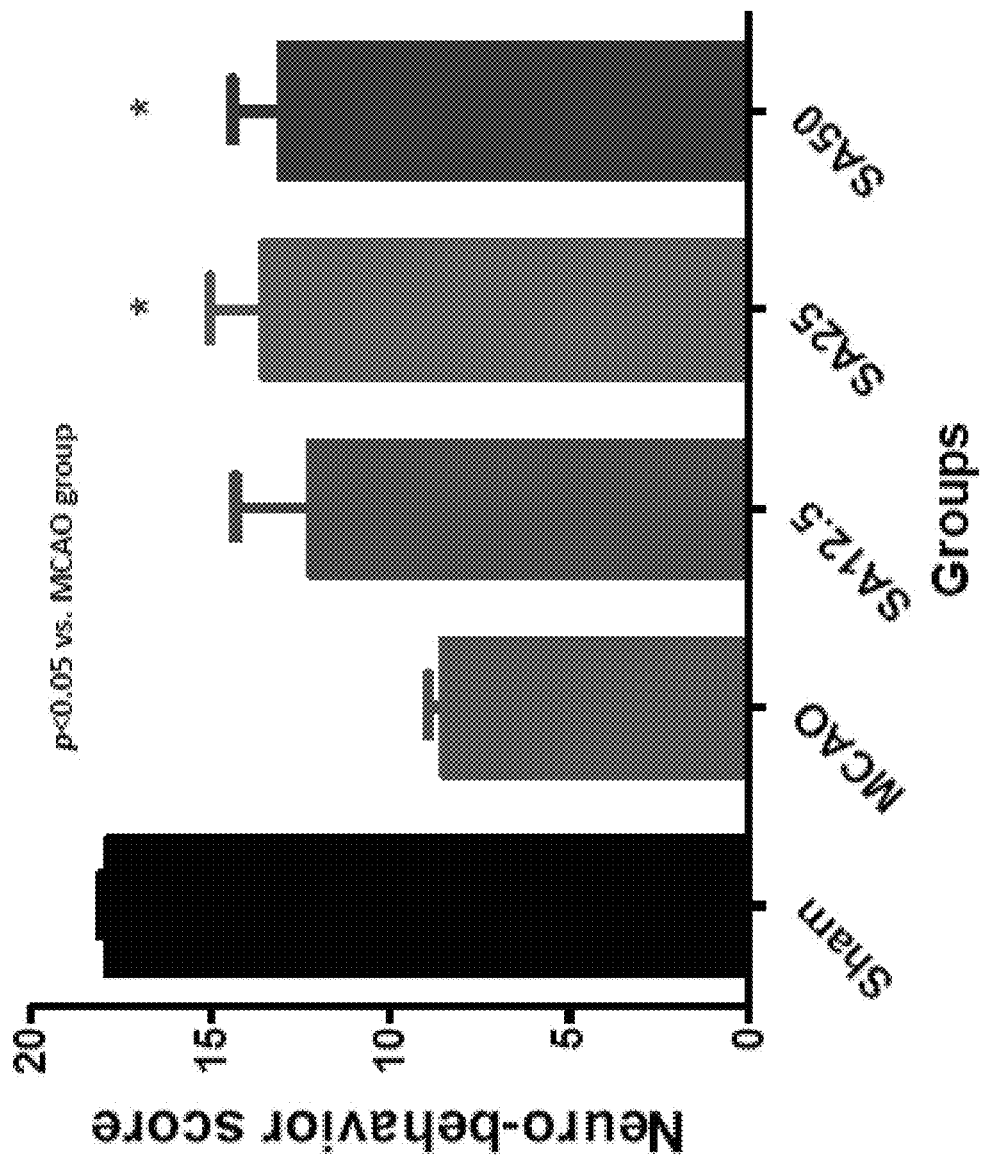
FIG. 31 shows that intranasal salvinorin A administration demonstrated dose-dependent improvements in neurobehavior.
Figure 32:
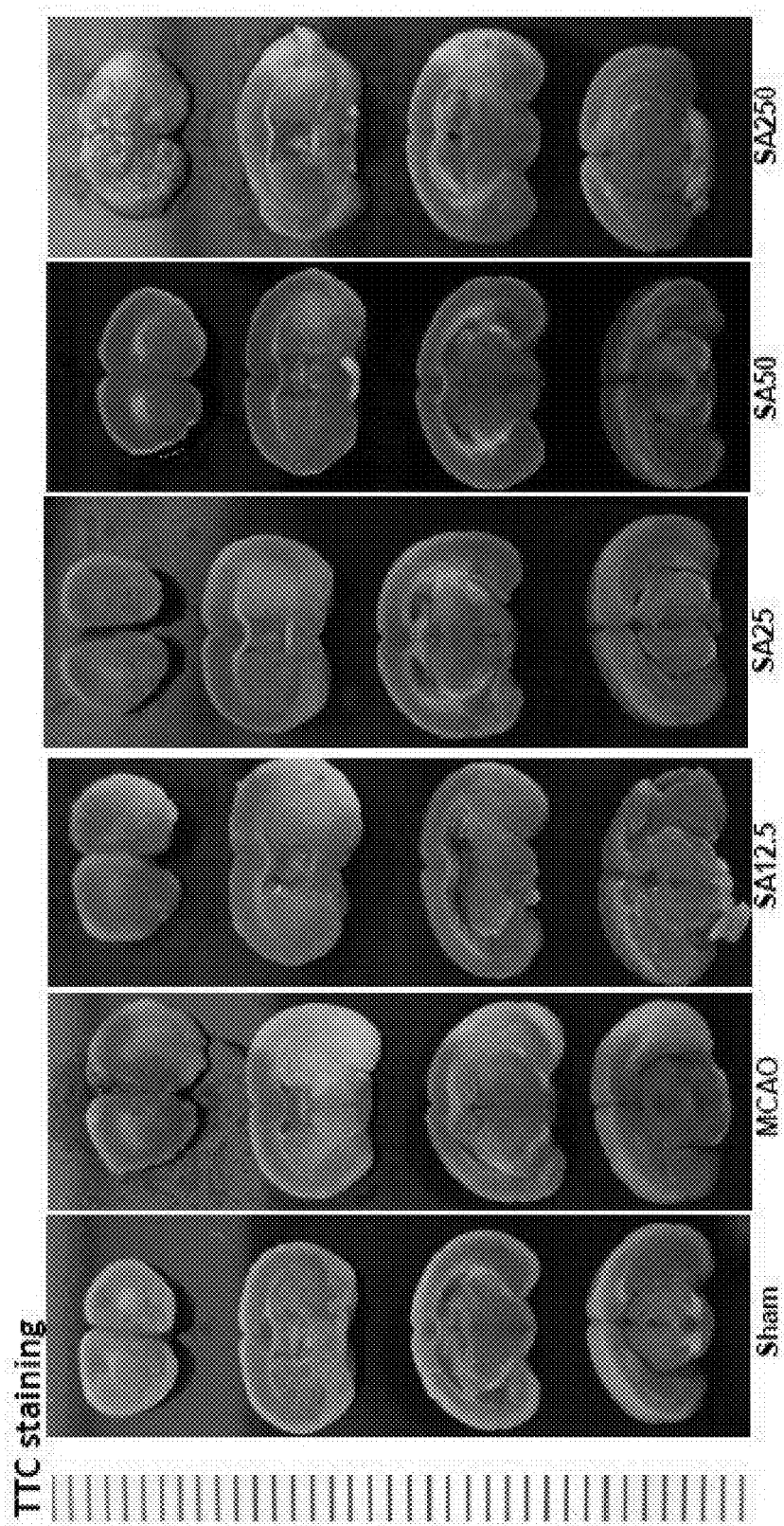
FIG. 32 shows that intranasal salvinorin A administration demonstrated dose-dependent reduction in infarct size as can be seen by the reduction of white infarcted area in TTC stains of the brain. Similar to the results indicated in FIG. 30, the protective effects diminish beyond the dose of 250 µg/kg.
Figure 33:
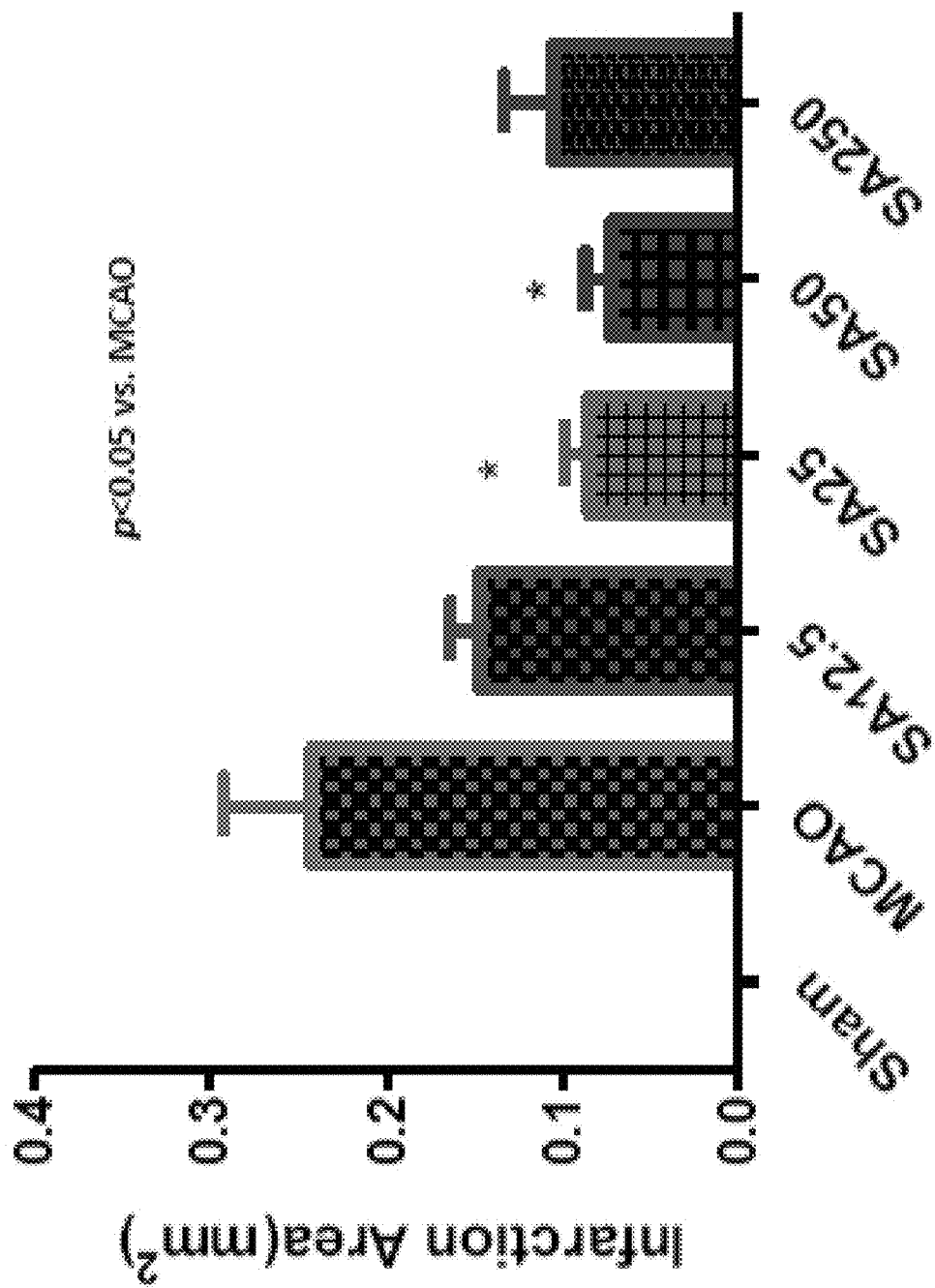
FIG. 33 shows the infarcted area as a function of the dose of intranasal salvinorin A administered.
Figure 34:
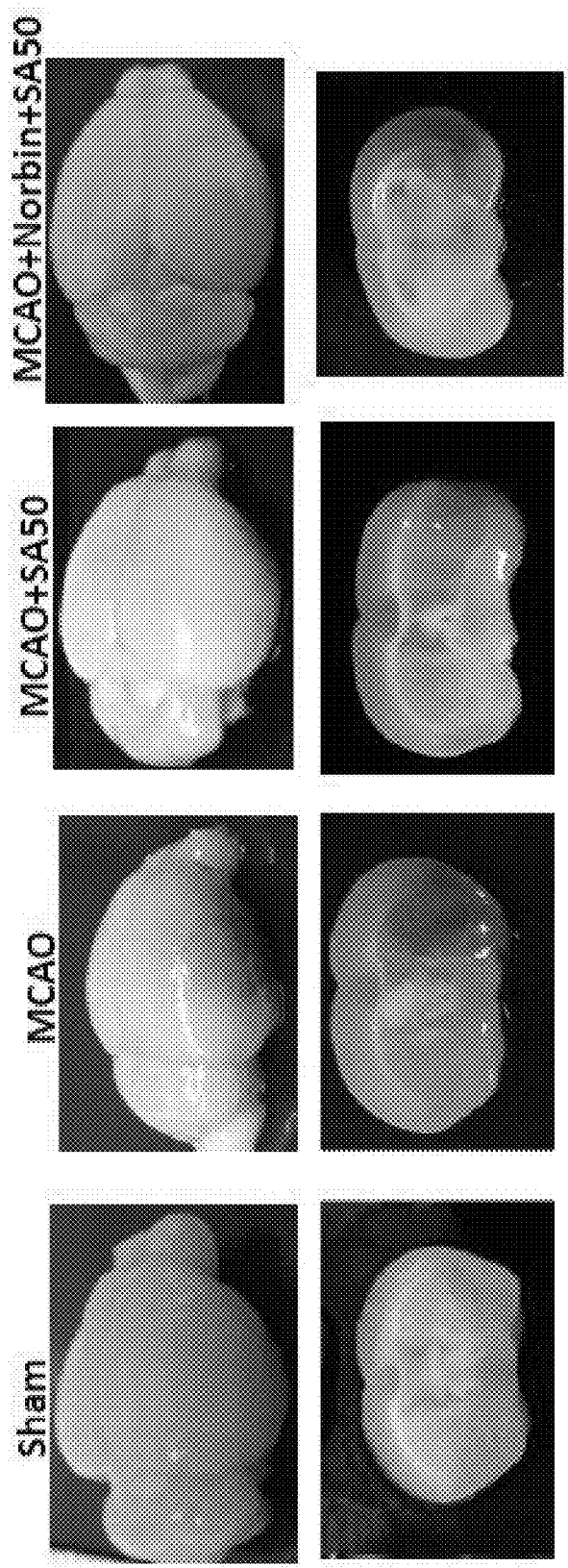
FIG. 34. Evans blue extravasation indicated blood brain bather disruption and vascular leakage after ischemia and reperfusion of the brain. Intranasal salvinorin A administration reduced the disruption and leakage, while the administration of the kappa receptor antagonist Norbinaltorphimine (norbin) inhibited the protective effect of salvinorin A.
Figure 35:
FIG. 35 shows that intranasal salvinorin A improves overall motor function. The mouse that has not been administered salvinorin A (the mouse on the ground) cannot walk normally since the left side was paralyzed 24 hours after 120 min of middle cerebral artery occlusion (MCAO). The mouse that has been administered intranasal salvinorin A after the injury (the mouse on the string) can crawl over a hanging string.

This Example demonstrates that intranasal administration of SA reduced infarct size and improved neurological outcome in a mouse stroke model. FIG. 29 depicts the protocol used. Briefly, a middle cerebral artery occlusion (MCAO) was induced in the mice and the indicated dose of salvinorin A in DMSO was administered intranasally. The mouse was reperfused for 24 hours after which the mice were euthanized and infarct size and vascular leakage was measured. Salvinorin A administration demonstrated dose-dependent improvements in motor function as measured by a grip strength score (FIG. 30) and neurobehavior (FIG. 31). Intranasal administration of salvinorin A also led to a dose-dependent reduction (except that the protective effect was diminished at a dose of 250 µg/kg) in infarct size as can be seen by the reduction of white infarcted area in TTC stains of the brain (FIGS. 32 and 33). Evans blue extravasation indicated blood brain barrier disruption and vascular leakage after ischemia and reperfusion of the brain. Intranasal salvinorin A administration reduced the disruption and leakage, while the administration of the kappa receptor antagonist Norbinaltorphimine (norbin) inhibited the protective effect of salvinorin A (FIG. 34). Intranasal salvinorin A improves overall motor function as shown in FIG. 35. The mouse that has not been administered salvinorin A (the mouse on the ground) cannot walk normally since the left side was paralyzed 24 hours after the MCAO; the mouse that has been administered intranasal salvinorin A (the mouse on the string) can crawl over a hanging string.

Intranasal administration of salvinorin A circumvents the need for intravenous access for quick drug delivery, reduces the time to deliver medication to patient, and increases the probability of successfully protecting the brain since the therapeutic window for ischemic brain injury is very narrow.

Example 7

Herkinorin Dilates Cerebral Vessels Via Kappa Opioid Receptor and Cyclic Adenosine Monophosphate (cAMP) in a Piglet Model Herkinorin is the first non-opioid mu agonist derived from the structurally related compound salvinorin A. Since kappa opioid receptor activation elicits pial artery dilation and salvinorin A is a potent cerebral vasculature dilator that activates nitric oxide synthases, kappa receptors, and adenosine triphosphate-sensitive potassium channels, it is likely that herkinorin could also elicit cerebrovasodilation. Herkinorin has an approximately 8-fold selectivity for mu over kappa receptors and an approximately 98-fold selectivity for mu over delta receptors in competition binding assays. Thus, it is important to elucidate whether its mu agonism plays any role in the cerebral vasculature effects for compounds from this category due to their potential clinical implications as non-opioid receptor agonist.

cAMP is a key modulator downstream of opioid receptors (Liu and Anand, 2001) and activation of cAMP signaling elicits vascular smooth muscle relaxation, resulting in cerebrovasodilation in the pig brain. In addition, administration of opioid receptor antagonists attenuated cAMP analog-induced pial, suggesting a potential connection between cAMP-mediated and opioid-mediated vasodilations. It is possible that herkinorin could induce cerebral vascular dilation via the cAMP pathway.

Here, we hypothesized that herkinorin, the first non-opioid mu agonist derived from salvinorin A, could dilate cerebral vasculature via mu and kappa opioid receptors and cAMP pathway. This hypothesis is distinctive from our previous study related to salvinorin A since herkinorin is categorized as a mu receptor agonist despite its structural similarity to the highly selective kappa opioid receptor agonist salvinorin A.

Experimental Procedures

Herkinorin (purity ≥99%) was obtained from Ascent Scientific LLC (Cambridge, Mass., USA). Isoproterenol, NTP, β-FNA, Rp-cAMPS and Sp-8-Br-2'-O-Me-cAMPS (Sp-cAMPS) were purchased from Sigma-Aldrich (St. Louis, Mo., USA). All other chemicals were of reagent grade and were obtained from Sigma as well.

In-Vitro Affinity Determination

Cell lines transfected with cloned rat kappa receptor and cloned human mu receptor were used for affinity determination as described previously. [3H]U69593, a potent kappa receptor agonist, and [3H]DAMGO, a μ receptor agonist, were used as competitors of the testing compounds. Herkinorin was prepared as 1 mg/ml stock in DMSO. A similar stock of salvinorin A (positive control) was also prepared. Ki determinations were performed at the National Institute of Mental Health's Psychoactive Drug Screening Program (Contract # HHSN-271-2008-00025-C, NIMH PDSP; http://pdsp.med.unc.edu/).

Binding Site Location with Computational Docking

Docking calculations were carried out using Docking-Server as described previously (http://www.dockingserver.com) to locate ligand binding site. The herkinorin coordinates were downloaded from the PubChem server (http://pubchem.ncbi.nlm.nih.gov/). The coordinates of the high-resolution structures of the murine μ opioid receptor (PDB code: 4DKL and kappa opioid receptor (PDB code: 4DJH) were downloaded from the protein data bank (PDB) server. We added Gasteiger partial charges to the herkinorin atoms through the server. Affinity (grid) maps of 30×30×30 Å grid points and 0.375 Å spacing were used in this study. The top tanked pose of the docking results were used to compare the overlapping of the ligand for each receptor. We used PyMOL (http://www.pymol.org/, Version 1.3, Schrödinger, LLC) to generate the graphical renderings.

Animals and Surgery

Newborn pigs (aged up to 6 days, 1.1-2.0 kg) of both genders were used for this study. Protocols were approved by the Institutional Animal Care and Use Committee of the University of Pennsylvania (Philadelphia). The newborn piglet model was used because its brain is gyrencepahalic and contains more white matter than grey matter, which is similar to that of humans. Furthermore, the head is large enough for the insertion of a cranial window and vascular visualization. Animals were induced with isoflurane (1-2 minimum alveolar concentration) and maintained with α-chloralose (80-100 mg/kg supplemented with 5 mg/kg·h, IV). Both femoral arteries were catheterized to monitor blood pressure and blood gas to maintain a constant carbon dioxide and pH. A catheter was inserted into the right femoral vein for medication administration. Animals were ventilated with room air after tracheal intubation. A heating pad was used to maintain the rectal temperature of animals at 37-39° C. A closed cranial window on the top of the head of the piglet was placed for direct pial artery visualization and diameter measurement. The closed cranial window consisted of three parts: a stainless steel ring, a circular glass cover slip, and three ports consisting of 17-gauge hypodermic needles attached to three precut holes in the stainless steel ring. CSF was collected through a cranial window port for cAMP measurement in some animals. The space under the window was filled with artificial CSF with the following composition (in mM): 3.0 KCl; 1.5 $MgCl_2$; 1.5 calcium chloride; 132 NaCl; 6.6 urea; 3.7 dextrose; 24.6 $NaHCO_3$; pH 7.33; $PaCO_2$, 46 mmHg; and $PO_2$ 43 mmHg. Artificial CSF was warmed to 37-38° C. before applying to the cerebral cortical surface. Pial arteries were observed with a video camera mounted on a dissecting microscope. Vascular diameter was measured from a video monitor that was connected to the camera with a video microscaler (VPA 550; For-A-Corp., Los Angeles, Calif.) by the investigator who administered the medication.

Protocol

Two types of pial vessels, small arteries (resting diameter 120-160 μm) and arterioles (resting diameter 50-70 μm), were monitored and recorded every 30 sec after injection of artificial CSF in the presence or absence of the investigated drugs. Typically, the window was flushed with 1-2 ml CSF through the port in 30 sec. Responses to herkinorin (0.1 nM and 10 nM, dissolved with DMSO) and isoproterenol (10 nM and 1 μM), were obtained with and without β-FNA, NTP, Sp-cAMPS and Rp-cAMPS. All tested drug solutions were made fresh on the day of use.

cAMP Assay

The cerebral cortical periarachnoid CSF samples were collected before and 10 min afterward administration of herkinorin and NTP to measure the cAMP level. Artificial CSF was slowly infused into one port of the window, allowing the CSF to drip freely into a collection tube on the opposite port. Commercially available ELISA kits (Assay Designs, Ann Arbor, Mich.) were used to quantify cAMP concentrations.

Statistical Analysis

All data were analyzed with one way-ANOVA (two-tailed) followed by Bonferroni post hoc test or by Dunnett's multiple comparison tests (SPSS 11.0 for Windows). An alpha level of $P<0.05$ was considered significant in all statistical tests. All values are represented as means±standard error. All P-values reported in the paper have been corrected for the effect of multiple comparisons. Although the sample size in this study was rather small, there was no apparent violation of the assumptions of lack of interaction, homogeneity of variance, and normal distribution.

Results

Herkinorin Binding with Mu and Kappa Receptors

Figure 36:
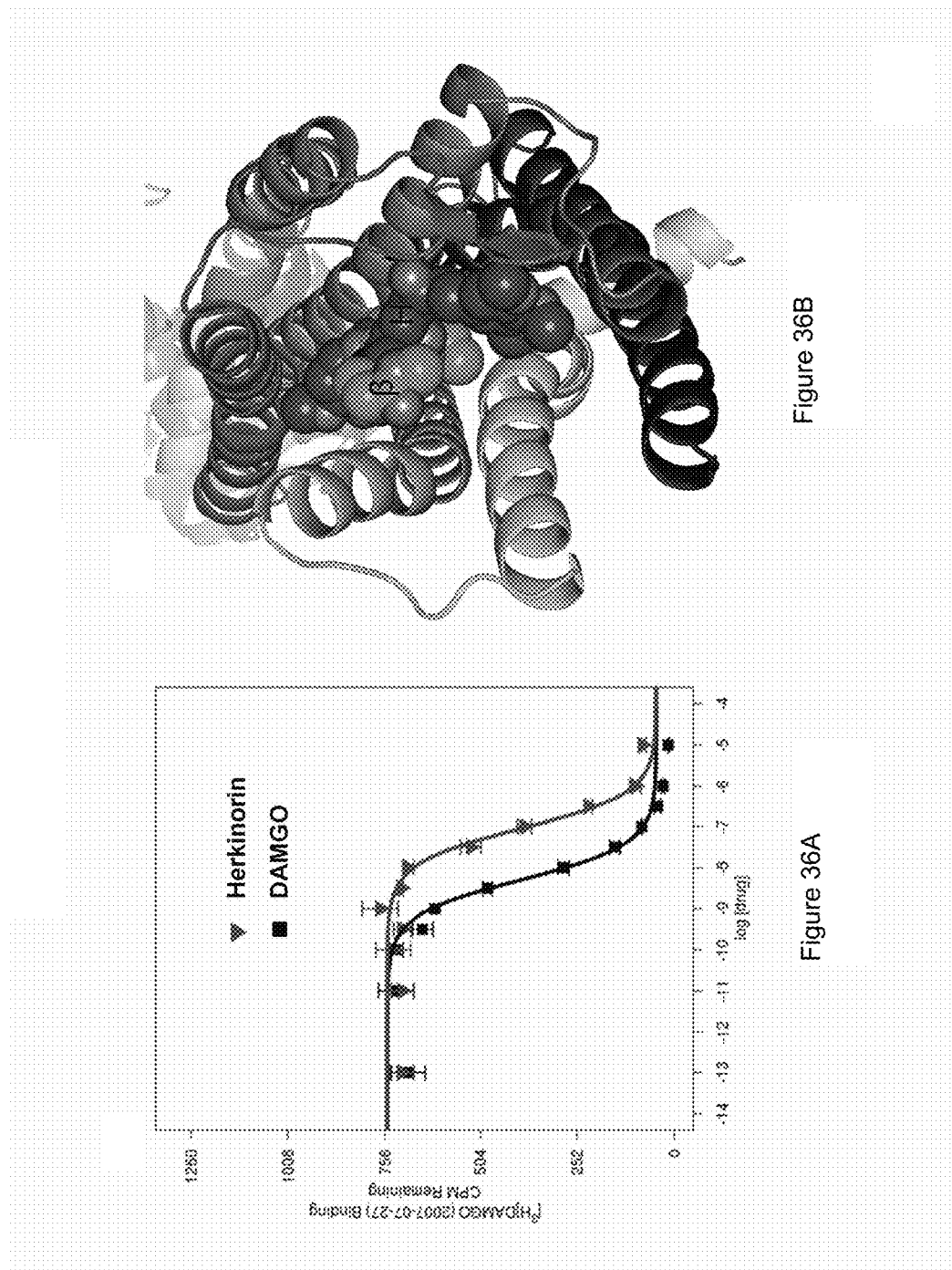
FIG. 36. Affinity determination for herkinorin in HEK cells over-expressed with mu and kappa opioid receptor.

As shown in FIG. 36A, herkinorin has a relatively weaker binding affinity with the mu receptor ($K_i$=45 nM) compared with DAMGO ($K_i$=2.5 nM). The binding site of herkinorin overlaps with that of β-FNA, a selective mu opioid receptor ligand in the crystal structure shown in FIG. 36B. Similarly, herkinorin has a relatively weaker affinity with kappa receptor (Ki=184 nM) compared with U69593 ($K_i$=0.8 nM, FIG. 37A) and the binding site overlaps with JDTic, a selective kappa receptor ligand in the crystal structure shown in FIG. 37B. The binding affinity of herkinorin to mu receptor is approximately 4-fold stronger than that to kappa receptor.

Herkinorin Induced Kappa Receptor-Dependent Vasodilation Upon Administration.

Figure 38:
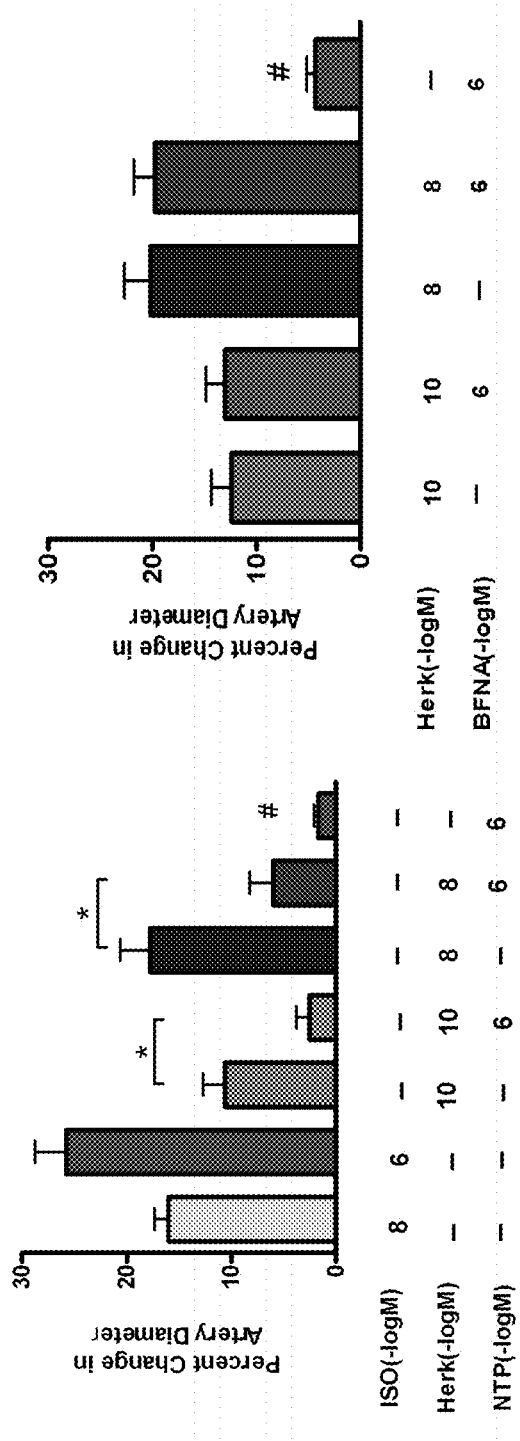
FIG. 38. The cerebrovasodilation effects of herkinorin is mediated though kappa opioid receptor.

The pial artery diameters increased after herkinorin administration without significant systemic blood pressure variation. Applying 0.1 nM herkinorin induced a 10.6% diameter dilation while 10 nM herkinorin induced a 17.8% diameter dilation on average. The dilation effects were totally abolished by norbinaltorphimine (NTP), a kappa receptor antagonist (FIG. 38A, Ps<0.05 compared with herkinorin administration groups), but not affected by β-FNA (FIG. 38B). Isoproterenol-induced pial artery dilation was unchanged by either NTP or β-FNA. β-FNA itself elicited minimal pial artery dilation (P<0.05, Dunnett's multiple comparison tests). These results indicate that the herkinorin-induced vasodilation is mediated via kappa, but not mu opioid receptor.

Pial Artery Dilation by Herkinorin was Mediated Via cAMP Signaling.

Figure 39:
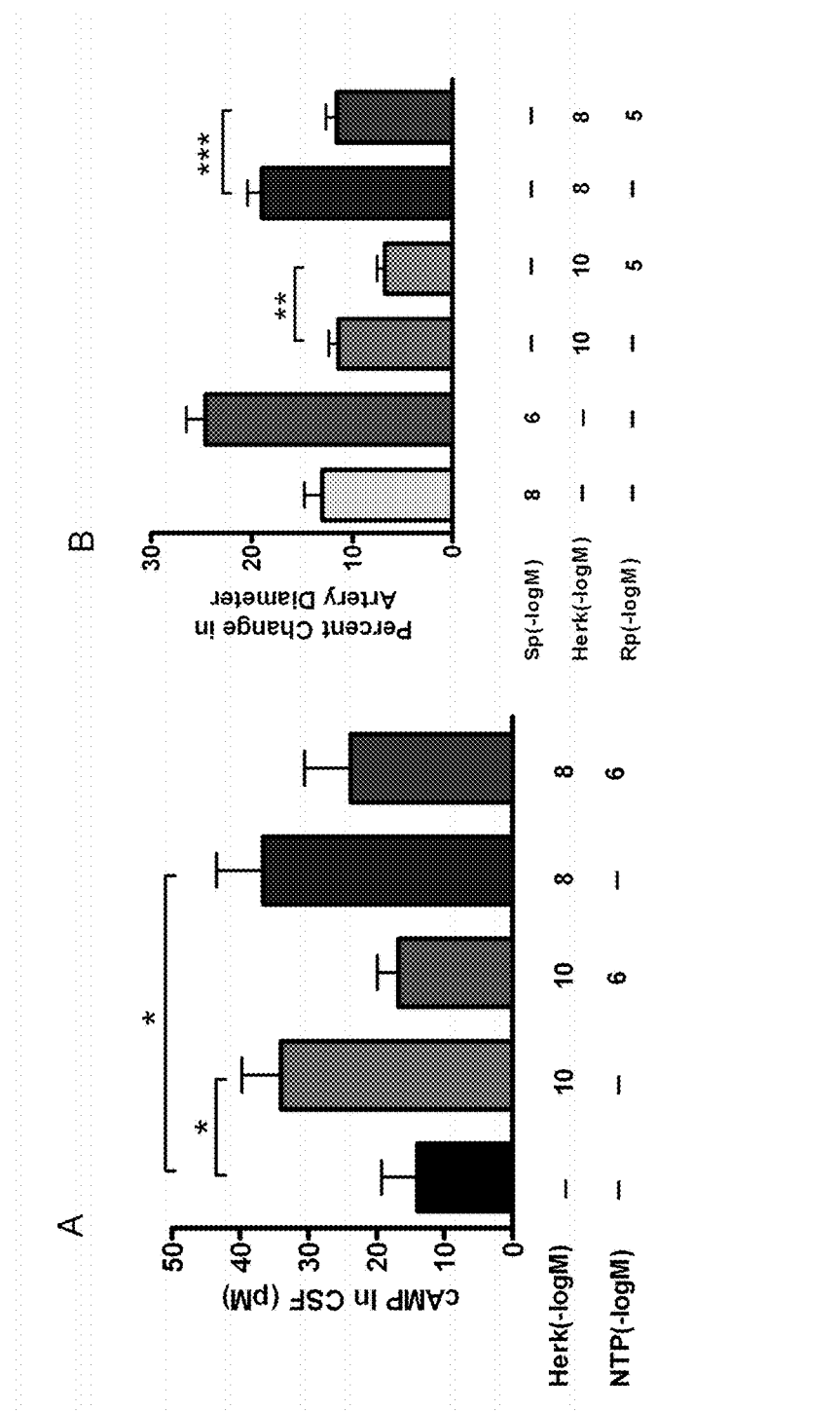
FIG. 39. Cerebrovasodilation effects of herkinorin is mediated via cAMP signaling.

Administration of herkinorin significantly increased cAMP levels in the CSF. The elevated cAMP levels were blocked by NTP, but not affected after β-FNA administration (FIG. 39A). Furthermore, the PKA antagonist Rp-cAMPS blunted herkinorin-mediated pial artery dilation. Co-administration of 10 μM Rp-cAMPS with 0.1 nM or 10 nM herkinorin attenuated the changes in pial artery diameters (FIG. 39B). The artery dilation induced by cAMP analog Sp-cAMPS is similar to that of Isoproterenol (Ps>0.05). These data suggest that cAMP/PKA pathway modulates the herkinorin-mediated cerebrovasodilation.

There are at least three findings in this Example. First, herkinorin is a potent pial artery dilator despite its classification as a non-opioid mu receptor agonist. Second, the herkinorin-induced pial artery dilation effects are modulated via kappa opioid receptors. No significant involvement of the mu opioid receptor is observed. Third, cAMP is demonstrated to be involved in the kappa agonist induced cerebral vascular dilatation previously. This study also confirms previous findings that herkinorin interacts with both mu and kappa opioid receptors and the binding site for this interaction overlaps with that of other traditional opioid receptor ligands.

Discussion

Herkinorin as a Non-Nitrogenous Opioid Receptor Agonist

Although herkinorin is an opioid receptor agonist, it does not contain nitrogen, an essential element for the traditional nitrogenous opioid ligand. Thus, herkinorin is the first non-opioid mu opioid receptor ligand. Herkinorin was discovered in 2005 when various analogues of the natural product Salvinorin A were synthesized to study the structure and the function of neoclerodane diterpenes. While salvinorin A is a selective kappa opioid agonist with no significant mu opioid receptor affinity, herkinorin acts on both mu and kappa receptors. Its affinity for the mu receptor is much stronger than that for the kappa receptor as demonstrated here and in other studies. Thus, unlike salvinorin A, herkinorin is categorized as a mu opioid receptor ligand. Its binding site overlaps well with the sites for other receptor ligands as demonstrated in the docking experiments.

Interestingly, the fact that herkinorin does not induce β-arrestin recruitment or promote receptor internalization suggests that herkinorin may not induce significant tolerance or dependence as traditional opioids do. A recent study indicates that herkinorin could produce a dose-dependent antinociceptive effect in a rat pain model, suggesting that herkinorin may be a promising starting point for developing novel analgesics without significant risk of dependence or tolerance.

The Effects on Brain Vessels and the Role of Receptors

In this Example, herkinorin exhibits similar pharmacological features for cerebral vasculature to salvinorin A as we demonstrated previously. Herkinorin seems to be a more potent artery dilator than salvinorin A because the concentration required to effectively dilate pial arteries (10%-16% changes compared to the baseline) is much lower for herkinorin (0.1 nM) compared to that of salvinorin A (10 nM). The cerebrovasodilation effect of herkinorin is blocked by NTP, but not β-FNA. Similar to our previous study, neither NTP nor β-FNA shows any effect on pial diameter by itself. Thus, the cerebral vascular dilatation effects of herkinorin are mediated through the kappa opioid receptor rather than the mu receptor.

The Role of cAMP

Cerebrovasodilation is mediated through several mechanisms, including cGMP, cAMP, and K+ channels.mIsoproterenol and cAMP increase the activities of calcium-dependent potassium channels in the cerebral vascular muscle, which is believed to induce vasodilatation. In this study, we observed that cerebrovasodilation is associated with the elevation of cAMP levels in the CSF after administration of herkinorin. Moreover, the cerebrovasodilation induced by herkinorin administration is abolished by the cAMP antagonist Rp-cAMPS. This observation is consistent with reports that administration of cAMP analog Sp-cAMPS elicits vasodilation, which can be blunted by Rp-cAMPS. Together, these findings indicate that cAMP plays an important role in the herkinorin induced cerebral vascular dilatation. P, it had been previously demonstrated the involvement of cGMP in salvinorin A-mediated vascular dilatation. It is highly likely that cGMP is also be involved in the dilatation effects of herkinorin.

Potential Implications

Because salvinorin A could dilate cerebral vasculature and preserve cerebral autoregulation from cerebral hypoxia/ischemia injury in a piglet model, it is highly likely that herkinorin has similar properties given that its cerebrovasodilative effects are modulated in a manner similar to salvinorin A. Thus, it can be an alternative non-opioid medication to be used during the perioperative period for patients who are at risk for cerebral vascular spasm or ischemia.

Example 8

Salvinorin a Treats Subarachnoid Hemorage

Figure 40:
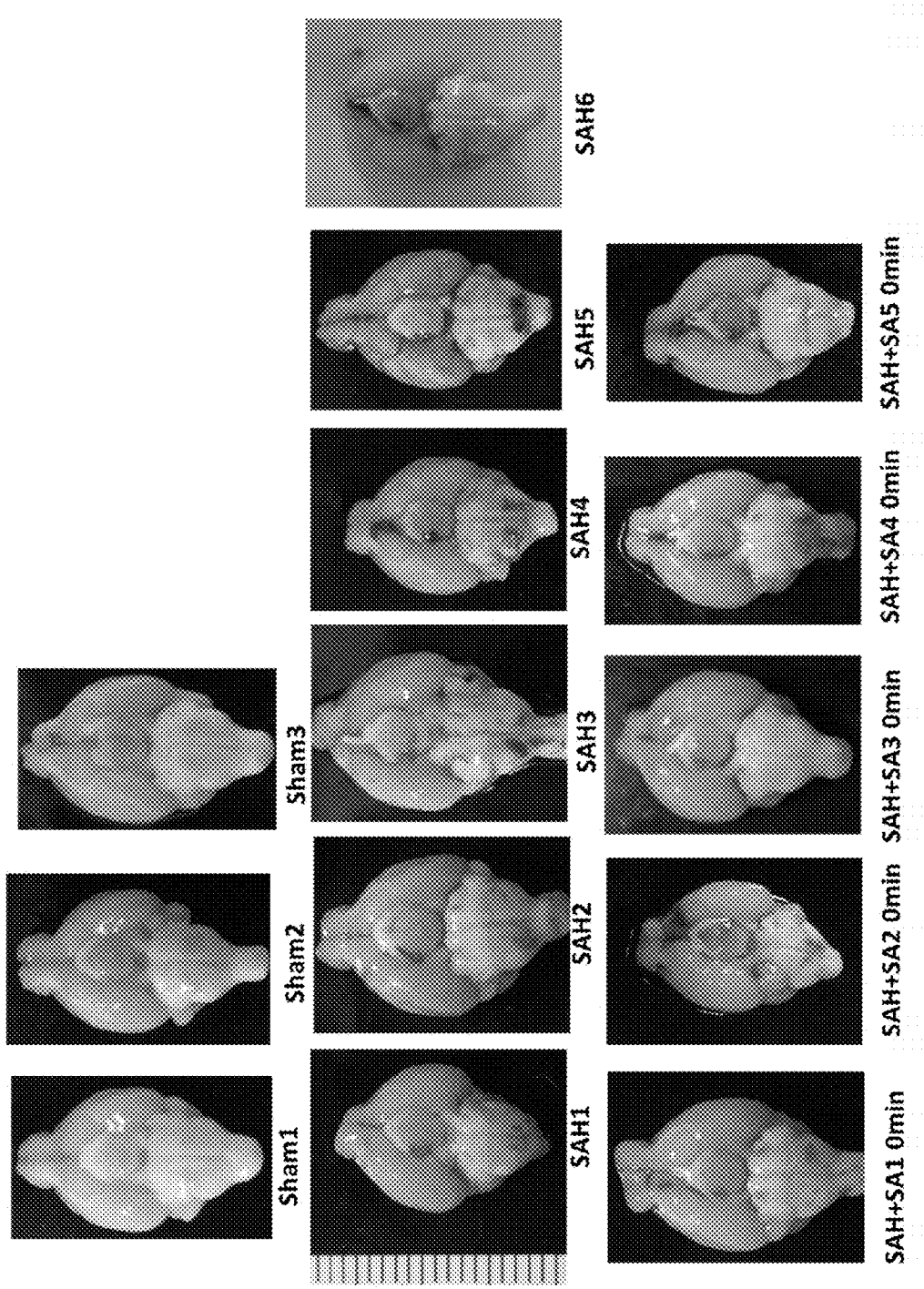
FIG. 40. Whole brain images (Ventral) after 24 hours for Sham, subarachnoid hemorrhage (SAH) and Salvanorin A (SA) treatment groups.
Figure 41:
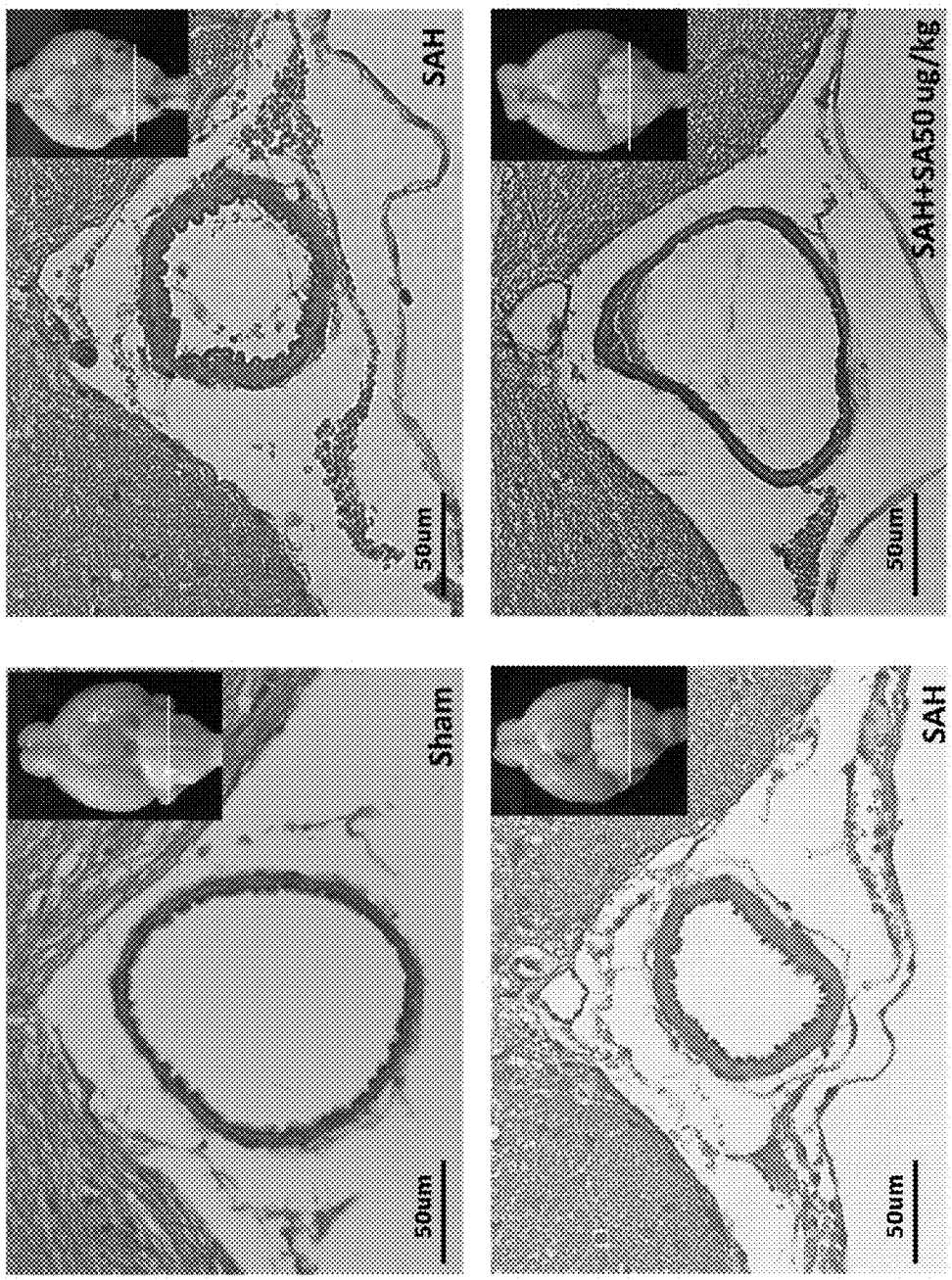
FIG. 41. H&E staining of basil artery of Sham, SAH and SA treatment groups.
Figure 42:
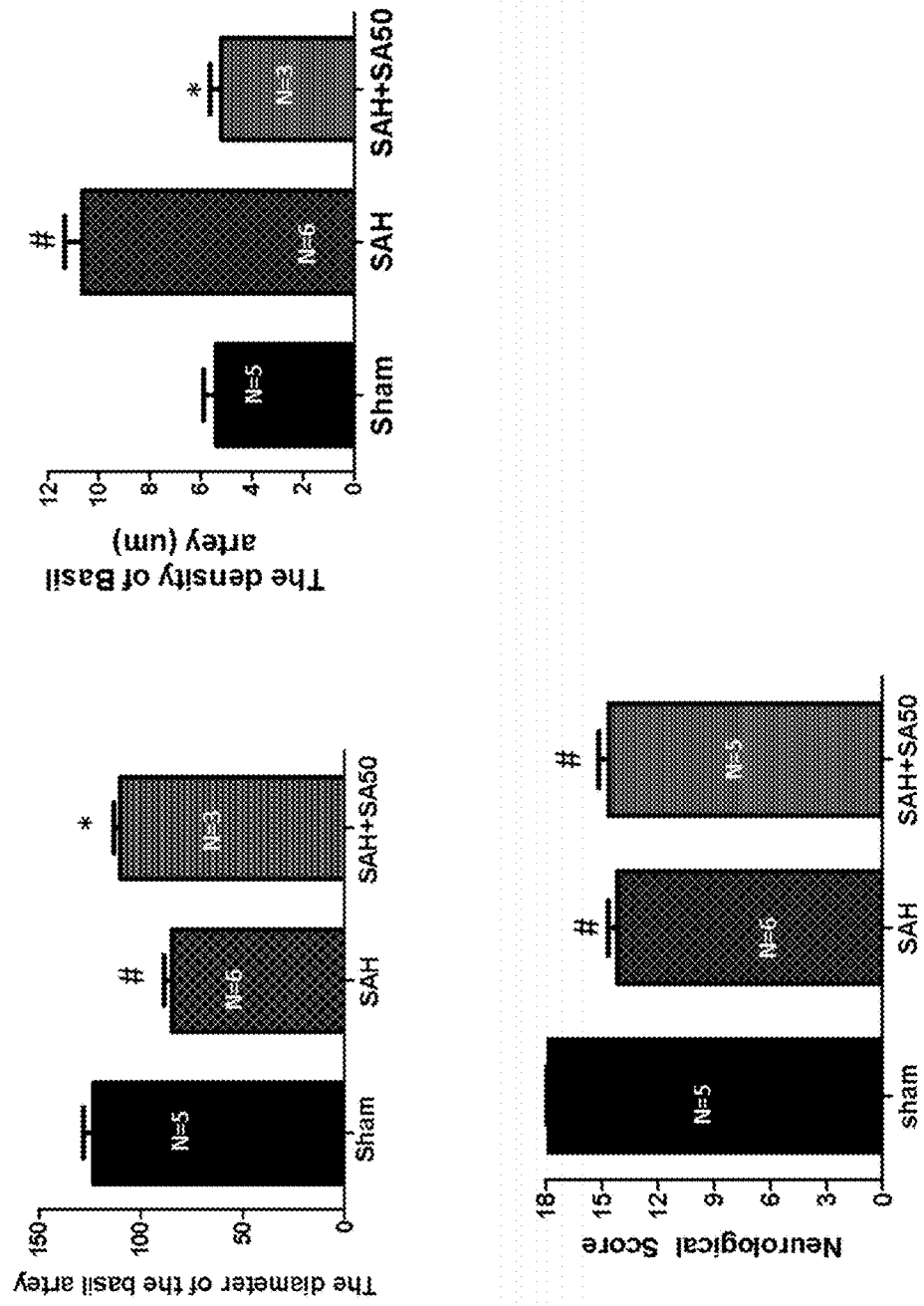
FIG. 42. Salvinorin A given after SAH (A) increased the diameter and (B) decreased the thickness of the wall of the basil artery significantly 24 hours after SAH. (C) Salvinorin A given after SAH has no significant effect on the neurological score #p<0.05 vs. Sham, *p<0.05 vs.SAH FIG. 43. Standard curve for Salvinorin A in methanol-acetone (4:1).

In this Example, three groups were used, i.e., sham (control), subarachnoid hemorrhage (SAH) and Salvanorin A (SA) treatment groups. Whole brain images (Ventral) were obtained 24 hours after SAH for the three groups, as shown in FIG. 40. In order to determine the diameters and thickness of the vessel wall in each group, brain stem sections with basilar arteries were stained with H&E in each group 24 hour after SAH (FIG. 41). The diameters of the vessels and the thickness of the vessel wall were measured using Image J after acquiring the image under microscope. Neurological tests were performed in a blinded manner and were assessed 24 hour after SAH. As shown in FIG. 42, Salvinorin A given 24 hours after SAH significantly (A) increased the diameter and (B) decreased the thickness of the wall of the basil artery significantly 24 hours after SAH, while (C) Salvinorin A given had no significant effect on the neurological score.

Example 9

Solubility of Salvinorin A

Salvinorin A is a very hydrophobic molecule and is insoluble in water. Salvinorin A is soluble in known to be soluble in organic solvents like ethanol, DMSO, and acetone. However, these solvent are not suitable for routine clinical use, especially for intravenous (IV) delivery. Since salvinorin A is useful clinically, for neurological disorders, there is a need to identify materials, preferably FDA approved materials, which can be used to formulate salvinorin A for clinical delivery. Physical and chemical properties of salvinorin are presented in Table 1 below.

TABLE 1

Physical and chemical properties of salvinorin A

| Property | Value | Comments |
|---|---|---|
| Molecular weight | 432.464 g/mol | Anhydrous |
| Molecular formula | C23H28O8 | Anhydrous |
| Crystal hydrate molecular formula | C23H28O8.⅓H2O | Trienhydrate crystal form |
| Melting point | 238-240° C. | Trienhydrate crystal form |
| Calculated LogP | 2.49 | ChemAxon/Marvin |
| pKa | None | Non-ionizable |
| Chiral centers | ? | 3 epimerizable |
| Optical rotation | .41 deg C. at 25° C. | c = 1 in CHCl3 |
| Water content | 1.4% (Karl Fischer) | Trienhydrate crystal form |

Lacking ionizable functional groups, salvinorin A cannot form soluble salts. Salvinorin A has eight hydrogen-bond acceptor sites, all oxygen atoms, and no hydrogen-bond donor groups. It would thus appear likely that its crystal lattice should comprise only weak non-bonded interactions between adjacent molecules and a resultant diminished lattice energy reflected in a low melting point. In fact, salvinorin A has a rather high melting point range reported as 238-240° C. An x-ray crystal structure of SA revealed that crystallization from aqueous organic solvents (acetone, methanol) yields SA as a stoichiometric hydrate with one molecule of water per three molecules of salvinorin A. Unfortunately, the x-ray structure did not resolve the positions of the water hydrogen atoms, so a detailed picture of the hydrogen-bonding linking salvinorin A molecules into the crystal lattice remains unclear. The existence of Salvinorin A as a high melting crystalline hydrate can be expected to influence its solubility behavior in organic and aqueous solvents Poor solubility will likely limit formulation approaches accessible for translation of the drug into a clinically applicable medicine.

Method

The solubility of salvinorin A in various solutions containing different types of cyclodextrin were tested. The following variants of cyclodextrin (Ashland) and water (as a negative control) were used.
1. 100% water;
2. 20% 2-Hydroxypropyl-β-cyclodextrin (HPBCD);
3. 20% 2-Hydroxypropyl-γ-cyclodextrin (HPGCD);
4. 20% α-cyclodextrin sulfated sodium salt; and
5. 20% β-cyclodextrin sulfated sodium salt.

For each compound, 20 g of that compound was dissolved in 100 mL water. Then, 0.3 mg salvinorin A was mixed into each solution. The solution was stirred overnight. Three duplicates of each sample were used. Samples were filtered with 0.2 μm PTFE filter (Waterman) before concentration determination. The solubility of salvinorin A was also tested in various other compounds.

Figure 43:
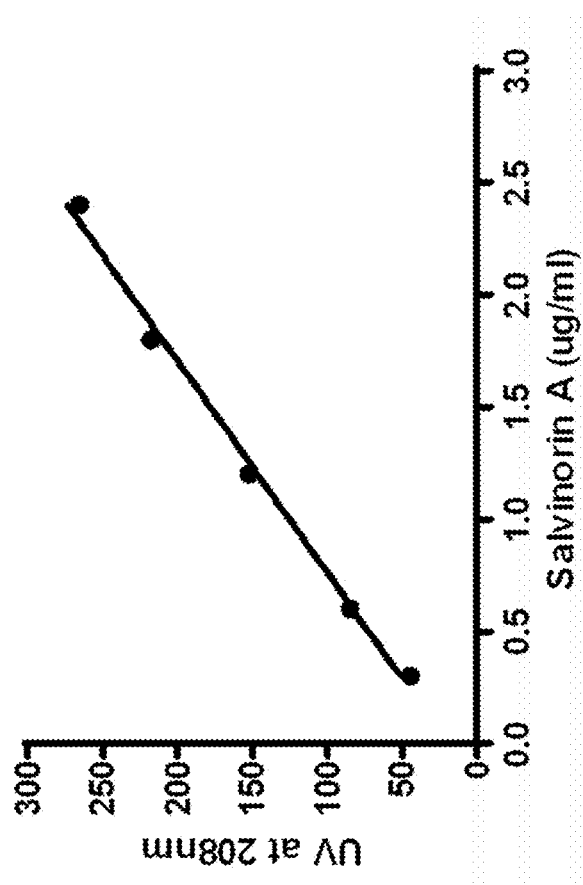

A standard curve with salvinorin A in Methanol-Acetone (4:1) was determined by chromatography using a C-18 HPLC column, using an elution speed of 1 mL/min water/acetonitrile (FIG. 43).

Results

Salvinorin A is only minimally soluble in water and either α-cyclodextrin sulfated sodium salt or β-cyclodextrin sulfated sodium salt. Of the tested cyclodextrins (Table 2), HPBCD demonstrated solubility of salvinorin A with a maximum concentration of more than 100 μg/mL. Thus, HPBCD can be used to formulate 50 μg/mL of salvinorin A, which is equivalent to the clinical dose for fentanyl. Interestingly, there is a significant solubility difference between HPBCD and HPGCD as indicated in Table 2, i.e., 122.5±0.6 μg/mL in 20% HPBCD vs. 52.6±0.9 μg/mL in 20% HPGCD. Salvinorin A solubility in other solvents is presented in Table 3.

TABLE 2

Solubility of Salvinorin A in various cyclodextrins

| Salvinorin A in | Concentration | |
|---|---|---|
| 100% water | 1.0 ± 0.1 ug/ml | N = 3 |
| 20% HPBCD | 122.5 ± 0.6 ug/ml | N = 3 |
| 20% HPGCD | 52.6 ± 0.9 ug/ml | N = 3 |
| 20% α-Cyclodextrin sulfated sodium salt | 1.0 ± 0.1 ug/ml | N = 3 |
| 20% β-Cyclodextrin sulfated sodium salt | 1.5 ± 0.1 ug/ml | N = 3 |

Data are presented as mean ± SD

TABLE 3

Salvinorin A solubility in other solvents

| Vehicle | Salvinorin A Solubility (μg/mL) |
|---|---|
| Water | <2 |
| Glyceryl monocaprylate | <2 |
| 2-Propanol | 22 |

TABLE 3-continued

Salvinorin A solubility in other solvents

| Vehicle | Salvinorin A Solubility (μg/mL) |
|---|---|
| 1,2-Propanediol | 59 |
| 2.5% Polysorbate 80 | <2 |
| 1.25% Polysorbate 80 and 2.5% Solutol HS15 | 25 |
| 5% Solutol HS15 | 26 |
| 10% Tetraglycol | <2 |
| 5% Vitamin E TPGS | 45 |
| N,N-dimethylacetamide | >5000 |
| N-methylpyrolidinone | >10000 |
| DMSO | >1000 |
| Ethanol | >1000 |
| 10% Bile salts | <2 |

Conclusion

Multiple acceptable solvents for salvinorin A were discovered, including some FDA materials approved for clinical usage. 20% HPBCD is a FDA approved material for IV drug delivery in clinical practice. For example, voriconazole (VFEND®, Pfizer) uses Sulfobutylether β-cyclodextrin for IV delivery.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating neurological injuries associated with cardiac arrest in a subject suffering from or having suffered cardiac arrest, the method comprising: administering to said subject a therapeutically effective amount of salvinorin A or a pharmaceutical composition thereof to induce vasodilation, wherein the neurological injuries are ischemic or reperfusion injuries to brain tissue and wherein the said administration is intranasal administration.

2. The method of claim 1, wherein the salvinorin A is administered during the cardiac arrest.

3. The method of claim 1, wherein the salvinorin A is administered while cardiopulmonary resuscitation (CPR) is being performed.

4. The method of claim 1, wherein the salvinorin A is administered after cardiopulmonary resuscitation (CPR) has been performed.

5. The method of claim 1, wherein the salvinorin A is administered to a subject undergoing coronary artery bypass surgery.

6. The method of claim 1, wherein the subject is a neonatal subject.

7. The method of claim 1, wherein the subject is a human.

8. A method of treating an ischemic stroke in a subject suffering from or having suffered the ischemic stroke, the method comprising: administering intranasally to said subject a therapeutically effective amount of salvinorin A or a pharmaceutical composition thereof to induce vasodilation.

9. The method of claim 8, wherein the salvinorin A is administered during or after the ischemic stroke.

10. The method of claim 8, wherein the subject is a neonatal subject.

11. The method of claim 8, wherein the subject is a human.

12. A method of treating a cerebral artery occlusion in a subject suffering from or having suffered a cerebral artery occlusion or cerebral hypoxia/ischemia, the method comprising: administering intranasally to said subject a therapeutically effective amount of salvinorin A or a pharmaceutical composition thereof to induce vasodilation.

13. The method of claim 12, wherein the salvinorin is administered while the subject is suffering or after the subject has suffered from the cerebral hypoxia/ischemia or cerebral artery occlusion.

14. The method of claim 12, wherein the subject is a neonatal subject.

15. The method of claim 12, wherein said subject is a human.

16. A method of treating a cerebral vasospasm in a subject with a subarachnoid hemorrhage, the method comprising: administering intranasally to said subject a therapeutically effective amount of salvinorin A or a pharmaceutical composition thereof to induce vasodilation.

17. The method of claim 16, wherein the subject is a neonatal subject.

18. The method of claim 16, wherein said subject is a human.

19. A method for producing cerebrovasodilation, in a subject, the method comprising administering intranasally to said subject a therapeutically effective amount of the pharmaceutical composition comprising aqueous salvinorin A and cyclodextrin, to induce vasodilation.

20. A method of treating neurological injuries associated with cardiac arrest in a subject suffering from or having suffered cardiac arrest, the method comprising: administering intranasally to said subject a therapeutically effective amount of the pharmaceutical composition comprising aqueous solution of salvinorin A and cyclodextrin to induce vasodilation, and wherein the neurological injuries are ischemic or reperfusion injuries to brain tissue.

21. A method of treating an ischemic stroke in a subject suffering from or having suffered the ischemic stroke, the method comprising: administering intranasally to said subject a therapeutically effective amount of the pharmaceutical composition comprising aqueous solution of salvinorin A and cyclodextrin to induce vasodilation.

22. A method of treating a cerebral artery occlusion in a subject suffering from or having suffered a cerebral artery occlusion or cerebral hypoxia/ischemia, the method comprising: administering intranasally to said subject a therapeutically effective amount of the pharmaceutical composition comprising aqueous salvinorin A and cyclodextrin, to induce vasodilation.

23. A method of treating cerebral vasospasm in a subject with a subarachnoid hemorrhage, the method comprising: administering intranasally to said subject a therapeutically effective amount of the pharmaceutical composition comprising aqueous solution of salvinorin A and cyclodextrin to induce vasodilation.

* * * * *